US010876159B2

(12) United States Patent
Taniguchi et al.

(10) Patent No.: US 10,876,159 B2
(45) Date of Patent: Dec. 29, 2020

(54) METHOD AND DEVICE FOR IDENTIFYING NUCLEOTIDE, AND METHOD AND DEVICE FOR DETERMINING NUCLEOTIDE SEQUENCE OF POLYNUCLEOTIDE

(71) Applicant: Quantum Biosystems Inc., Tokyo (JP)

(72) Inventors: Masateru Taniguchi, Osaka (JP);
Makusu Tsutsui, Osaka (JP);
Kazumichi Yokota, Osaka (JP); Tomoji Kawai, Osaka (JP)

(73) Assignee: QUANTUM BIOSYSTEMS INC., Osaka (JP)

( * ) Notice: Subject to any disclaimer, the term of this patent is extended or adjusted under 35 U.S.C. 154(b) by 0 days.

(21) Appl. No.: 16/234,908

(22) Filed: Dec. 28, 2018

(65) Prior Publication Data
US 2019/0367979 A1    Dec. 5, 2019

Related U.S. Application Data

(63) Continuation of application No. 14/883,494, filed on Oct. 14, 2015, now Pat. No. 10,202,644, which is a continuation of application No. 13/992,328, filed as application No. PCT/JP2011/054631 on Mar. 1, 2011, now Pat. No. 9,194,838.
(Continued)

(51) Int. Cl.
*G01N 27/327* (2006.01)
*C12Q 1/6874* (2018.01)
*C12Q 1/6869* (2018.01)

(52) U.S. Cl.
CPC ........ *C12Q 1/6874* (2013.01); *C12Q 1/6869* (2013.01); *G01N 27/3278* (2013.01)

(58) Field of Classification Search
CPC . C12Q 1/6874; C12Q 1/6869; G01N 27/3278
See application file for complete search history.

(56) References Cited

U.S. PATENT DOCUMENTS

| 5,092,972 A | 3/1992 | Ghowsi |
| 5,122,248 A | 6/1992 | Karger et al. |

(Continued)

FOREIGN PATENT DOCUMENTS

| CN | 1828849 A | 9/2006 |
| CN | 101046458 A | 10/2007 |

(Continued)

OTHER PUBLICATIONS

Co-pending U.S. Appl. No. 16/266,363, filed Feb. 4, 2019.
(Continued)

*Primary Examiner* — J. Christopher Ball
(74) *Attorney, Agent, or Firm* — Wilson Sonsini Goodrich & Rosati

(57) ABSTRACT

The present invention provides technology that uses current measurements to identify nucleotides and determine a nucleotide sequence in polynucleotides. The present invention calculates a modal value of a tunnel current that arises when a nucleotide or polynucleotide for analysis passes through between electrodes, and then employs the calculated modal value. The present invention accordingly enables direct rapid implementation to identify nucleotides and to determine a nucleotide sequence in a polynucleotide without marking.

21 Claims, 21 Drawing Sheets

Related U.S. Application Data

(60) Provisional application No. 61/310,215, filed on Mar. 3, 2010.

(56) References Cited

U.S. PATENT DOCUMENTS

| | | |
|---|---|---|
| 5,151,164 A | 9/1992 | Blanchard et al. |
| 5,262,031 A | 11/1993 | Lux et al. |
| 5,329,236 A | 7/1994 | Gemma et al. |
| 5,593,838 A | 1/1997 | Zanzucchi et al. |
| 5,906,723 A | 5/1999 | Mathies et al. |
| 6,159,353 A | 12/2000 | West et al. |
| 6,447,663 B1 | 9/2002 | Lee et al. |
| 6,491,805 B1 | 12/2002 | Gordon et al. |
| 6,613,513 B1 | 9/2003 | Parce et al. |
| 6,905,586 B2 | 6/2005 | Lee et al. |
| 7,033,476 B2 | 4/2006 | Lee et al. |
| 7,468,271 B2 | 12/2008 | Golovchenko et al. |
| 7,892,414 B1 | 2/2011 | Sumner |
| 7,918,979 B2 | 4/2011 | Han et al. |
| 8,105,471 B1 | 1/2012 | Han et al. |
| 8,236,595 B2 | 8/2012 | Agarwal et al. |
| 8,333,934 B2 | 12/2012 | Cao et al. |
| 8,652,779 B2 | 2/2014 | Turner et al. |
| 9,194,838 B2 | 11/2015 | Taniguchi et al. |
| 9,506,894 B2 | 11/2016 | Kawai et al. |
| 9,535,033 B2 | 1/2017 | Kawai et al. |
| 9,644,236 B2 | 5/2017 | Kawai et al. |
| 10,202,644 B2 | 2/2019 | Taniguchi et al. |
| 10,261,066 B2 | 4/2019 | Ikeda et al. |
| 10,413,903 B2 | 9/2019 | Taniguchi |
| 10,438,811 B1 | 10/2019 | Ikeda |
| 10,466,228 B2 | 11/2019 | Ikeda et al. |
| 2001/0046681 A1 | 11/2001 | Senapathy |
| 2002/0046953 A1 | 4/2002 | Lee et al. |
| 2002/0081744 A1 | 6/2002 | Chan et al. |
| 2002/0168671 A1 | 11/2002 | Burns et al. |
| 2002/0168810 A1 | 11/2002 | Jackson |
| 2003/0052006 A1 | 3/2003 | Noca et al. |
| 2003/0075445 A1 | 4/2003 | Woudenberg et al. |
| 2003/0085719 A1 | 5/2003 | Yoon et al. |
| 2003/0089606 A1 | 5/2003 | Parce et al. |
| 2003/0104428 A1 | 6/2003 | Branton et al. |
| 2003/0141189 A1 | 7/2003 | Lee et al. |
| 2003/0207326 A1 | 11/2003 | Su et al. |
| 2004/0124084 A1 | 7/2004 | Lee et al. |
| 2004/0144658 A1 | 7/2004 | Flory |
| 2004/0161708 A1 | 8/2004 | Nagase et al. |
| 2005/0048513 A1 | 3/2005 | Harwit et al. |
| 2005/0051768 A1 | 3/2005 | Kim et al. |
| 2005/0061669 A1 | 3/2005 | Woudenberg et al. |
| 2005/0084865 A1 | 4/2005 | Yu et al. |
| 2005/0112860 A1* | 5/2005 | Park ................. B82Y 10/00 438/597 |
| 2005/0127035 A1 | 6/2005 | Ling et al. |
| 2005/0136419 A1 | 6/2005 | Lee |
| 2005/0202444 A1 | 9/2005 | Zhu |
| 2005/0202446 A1 | 9/2005 | Yang et al. |
| 2005/0227239 A1 | 10/2005 | Joyce |
| 2006/0011480 A1 | 1/2006 | Sano et al. |
| 2006/0057585 A1 | 3/2006 | McAllister |
| 2006/0071209 A1 | 4/2006 | Flory et al. |
| 2006/0154399 A1 | 7/2006 | Sauer et al. |
| 2006/0154400 A1 | 7/2006 | Choi et al. |
| 2006/0210995 A1 | 9/2006 | Joyce |
| 2006/0275911 A1 | 12/2006 | Wang et al. |
| 2007/0029911 A1 | 2/2007 | Hudspeth et al. |
| 2007/0042366 A1 | 2/2007 | Ling |
| 2007/0048745 A1 | 3/2007 | Joyce et al. |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 | 5/2008 | Sauer et al. |
| 2008/0171316 A1 | 7/2008 | Golovchenko et al. |
| 2008/0202931 A1 | 8/2008 | Petsev et al. |
| 2008/0215252 A1 | 9/2008 | Kawai et al. |
| 2008/0248561 A1 | 10/2008 | Golovchenko et al. |
| 2009/0023146 A1 | 1/2009 | Harnack et al. |
| 2009/0155917 A1 | 6/2009 | Umezawa et al. |
| 2009/0215156 A1 | 8/2009 | Chung et al. |
| 2009/0229854 A1 | 9/2009 | Fredenberg et al. |
| 2009/0242429 A1 | 10/2009 | Sitdikov et al. |
| 2009/0283412 A1 | 11/2009 | Sansinena et al. |
| 2009/0286936 A1 | 11/2009 | Ogata et al. |
| 2009/0305273 A1 | 12/2009 | Cao et al. |
| 2010/0025249 A1 | 2/2010 | Polonsky et al. |
| 2010/0066348 A1 | 3/2010 | Merz et al. |
| 2010/0084276 A1 | 4/2010 | Lindsay et al. |
| 2010/0184062 A1 | 7/2010 | Steinmueller-Nethl et al. |
| 2010/0188109 A1 | 7/2010 | Edel et al. |
| 2010/0243449 A1 | 9/2010 | Oliver |
| 2010/0267158 A1 | 10/2010 | Chou et al. |
| 2010/0292101 A1 | 11/2010 | So et al. |
| 2010/0331194 A1 | 12/2010 | Turner et al. |
| 2011/0056845 A1 | 3/2011 | Stellacci et al. |
| 2011/0171634 A1 | 7/2011 | Xiao et al. |
| 2011/0179852 A1 | 7/2011 | Polonsky et al. |
| 2011/0181150 A1 | 7/2011 | Mahameed et al. |
| 2011/0236984 A1 | 9/2011 | Sun et al. |
| 2011/0250464 A1 | 10/2011 | Wilson et al. |
| 2011/0287956 A1 | 11/2011 | Iqbal et al. |
| 2012/0041727 A1 | 2/2012 | Mishra et al. |
| 2012/0097539 A1 | 4/2012 | Qian et al. |
| 2012/0132886 A1 | 5/2012 | Peng et al. |
| 2012/0184047 A1 | 7/2012 | Jonsson et al. |
| 2012/0193237 A1 | 8/2012 | Afzali-Ardakani et al. |
| 2012/0199485 A1 | 8/2012 | Sauer et al. |
| 2012/0254715 A1 | 10/2012 | Schwartz et al. |
| 2012/0298511 A1 | 11/2012 | Yamamoto |
| 2012/0322055 A1 | 12/2012 | Royyuru |
| 2013/0001082 A1 | 1/2013 | Afzali-Ardakani et al. |
| 2013/0092547 A1 | 4/2013 | Li et al. |
| 2013/0157271 A1 | 6/2013 | Coursey et al. |
| 2013/0186758 A1 | 7/2013 | Saha et al. |
| 2013/0240359 A1 | 9/2013 | Turner et al. |
| 2013/0264207 A1 | 10/2013 | Ju et al. |
| 2013/0334047 A1 | 12/2013 | Jeong et al. |
| 2014/0000105 A1 | 1/2014 | Bielick et al. |
| 2014/0008225 A1 | 1/2014 | Jeon et al. |
| 2014/0031995 A1 | 1/2014 | Kawai et al. |
| 2014/0055150 A1 | 2/2014 | Kawai et al. |
| 2014/0103945 A1 | 4/2014 | Eid et al. |
| 2014/0183040 A1 | 7/2014 | Kawai et al. |
| 2014/0202857 A1 | 7/2014 | Valbusa et al. |
| 2014/0273186 A1 | 9/2014 | Oxenrider |
| 2014/0300339 A1 | 10/2014 | Taniguchi et al. |
| 2014/0302675 A1 | 10/2014 | Astier et al. |
| 2014/0364324 A1 | 12/2014 | Turner et al. |
| 2014/0374695 A1 | 12/2014 | Astier et al. |
| 2015/0107996 A1 | 4/2015 | Chen |
| 2015/0111759 A1 | 4/2015 | Ju et al. |
| 2015/0132756 A1 | 5/2015 | Peter et al. |
| 2015/0219593 A1 | 8/2015 | Kawai et al. |
| 2015/0310228 A1 | 10/2015 | Benz et al. |
| 2015/0323490 A1 | 11/2015 | Luan et al. |
| 2016/0048690 A1 | 2/2016 | Tanishima et al. |
| 2016/0049327 A1 | 2/2016 | Singh et al. |
| 2016/0245789 A1 | 8/2016 | Ikeda et al. |
| 2016/0245790 A1 | 8/2016 | Kawai et al. |
| 2016/0320364 A1 | 11/2016 | Ikeda et al. |
| 2016/0377591 A1 | 12/2016 | Kawai et al. |
| 2017/0131237 A1 | 5/2017 | Ikeda |
| 2017/0144158 A1 | 5/2017 | Taniguchi |
| 2017/0146510 A1 | 5/2017 | Ikeda et al. |
| 2017/0146511 A1 | 5/2017 | Taniguchi et al. |
| 2017/0306396 A1 | 10/2017 | Kawai et al. |
| 2018/0023132 A1 | 1/2018 | Kawai et al. |
| 2019/0071720 A1 | 3/2019 | Nordman et al. |

FOREIGN PATENT DOCUMENTS

| | | |
|---|---|---|
| CN | 101920932 A | 12/2010 |
| CN | 102180440 A | 9/2011 |
| CN | 102753708 A | 10/2012 |

(56) References Cited

FOREIGN PATENT DOCUMENTS

| | | |
|---|---|---|
| CN | 102914395 A | 2/2013 |
| CN | 103203256 A | 7/2013 |
| CN | 103502795 A | 1/2014 |
| EP | 1419112 A1 | 5/2004 |
| EP | 2573554 A1 | 3/2013 |
| EP | 3315461 A1 | 5/2018 |
| JP | 62-194673 A | 8/1987 |
| JP | S6437640 A | 2/1989 |
| JP | 04-302151 A | 10/1992 |
| JP | H04302151 A | 10/1992 |
| JP | H0774337 A | 3/1995 |
| JP | H10283230 A | 10/1998 |
| JP | 2003507026 A | 2/2003 |
| JP | 2003090815 A | 3/2003 |
| JP | 2003332555 A | 11/2003 |
| JP | 2003533676 A | 11/2003 |
| JP | 2004233356 A | 8/2004 |
| JP | 2004247203 A | 9/2004 |
| JP | 2004303162 A | 10/2004 |
| JP | 2005501234 A | 1/2005 |
| JP | 2005257687 A | 9/2005 |
| JP | 2006078491 A | 3/2006 |
| JP | 2006526777 A | 11/2006 |
| JP | 2007272212 A | 10/2007 |
| JP | 2008032529 A | 2/2008 |
| JP | 2008146538 A | 6/2008 |
| JP | 4128573 B2 | 7/2008 |
| JP | 2008186975 A | 8/2008 |
| JP | 2008536124 A | 9/2008 |
| JP | 4289938 B2 | 7/2009 |
| JP | 2009527817 A | 7/2009 |
| JP | 2009210272 A | 9/2009 |
| JP | 2009272432 A | 11/2009 |
| JP | 2010510476 A | 4/2010 |
| JP | 2010513853 A | 4/2010 |
| JP | 2010227735 A | 10/2010 |
| JP | 2011500025 A | 1/2011 |
| JP | 2011054631 A | 3/2011 |
| JP | 2011516050 A | 5/2011 |
| JP | 4719906 B2 | 7/2011 |
| JP | 2011163934 A | 8/2011 |
| JP | 2011211905 A | 10/2011 |
| JP | 2012110258 A | 6/2012 |
| JP | 2012118709 A | 6/2012 |
| JP | 2013036865 A | 2/2013 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014074599 A | 4/2014 |
| JP | 2014173936 A | 9/2014 |
| JP | 2015059824 A | 3/2015 |
| JP | 2015077652 A | 4/2015 |
| KR | 1020140031559 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | WO-0113088 A1 | 2/2001 |
| WO | WO-0181896 A1 | 11/2001 |
| WO | WO-0181908 A1 | 11/2001 |
| WO | WO-03018484 A1 | 3/2003 |
| WO | WO-03042396 A2 | 5/2003 |
| WO | WO-03106693 A2 | 12/2003 |
| WO | WO-2007013370 A1 | 2/2007 |
| WO | WO-2008071982 A2 | 6/2008 |
| WO | WO-2008071982 A3 | 7/2008 |
| WO | WO-2008079169 A2 | 7/2008 |
| WO | WO-2009045472 A1 | 4/2009 |
| WO | WO-2009093019 A2 | 7/2009 |
| WO | WO-2009120642 A1 | 10/2009 |
| WO | WO-2009149362 A2 | 12/2009 |
| WO | WO-2010111605 A2 | 9/2010 |
| WO | WO-2010116595 A1 | 10/2010 |
| WO | WO-2010111605 A3 | 11/2010 |
| WO | WO-2011082419 A2 | 7/2011 |
| WO | WO-2011097171 A1 | 8/2011 |
| WO | WO-2011108540 A1 | 9/2011 |
| WO | WO-2012009578 A2 | 1/2012 |
| WO | WO-2012009578 A3 | 4/2012 |
| WO | WO-2012164679 A1 | 12/2012 |
| WO | WO-2012170560 A2 | 12/2012 |
| WO | WO-2013016486 A1 | 1/2013 |
| WO | WO-2013066456 A2 | 5/2013 |
| WO | WO-2013074546 A1 | 5/2013 |
| WO | WO-2013076943 A1 | 5/2013 |
| WO | WO-2013066456 A3 | 7/2013 |
| WO | WO-2013100949 A1 | 7/2013 |
| WO | WO-2013115185 A1 | 8/2013 |
| WO | WO-2013116509 A1 | 8/2013 |
| WO | WO-2013147208 A1 | 10/2013 |
| WO | WO-2014027580 A1 | 2/2014 |
| WO | WO-2014084931 A1 | 6/2014 |
| WO | WO-2015028885 A2 | 3/2015 |
| WO | WO-2015028886 A2 | 3/2015 |
| WO | WO-2015042200 A1 | 3/2015 |
| WO | WO-2015028885 A3 | 4/2015 |
| WO | WO-2015057870 A1 | 4/2015 |
| WO | WO-2015028886 A3 | 5/2015 |
| WO | WO-2015111760 A1 | 7/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016010975 A2 | 1/2016 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

Office Action dated Jun. 26, 2017 for U.S. Appl. No. 14/883,494.
Office action dated Oct. 6, 2016 for U.S. Appl. No. 14/883,494.
U.S. Appl. No. 14/883,494 Notice of Allowance dated Jan. 4, 2019.
U.S. Appl. No. 14/883,494 Notice of Allowance dated Oct. 10, 2018.
U.S. Appl. No. 14/883,494 Notice of Allowance dated Dec. 21, 2018.
U.S. Appl. No. 14/883,494 Notice of Allowance dated Nov. 19, 2018.
U.S. Appl. No. 14/883,494 Notice of Allowance dated Dec. 27, 2018.
U.S. Appl. No. 14/883,494 Office Action dated Mar. 2, 2018.
Anima et al. Fabrications of insulator-protected nanometer-sized electrode gaps. Journal of Applied Physics 115:114310 (2014). 6 pages. doi: 10.1063/1.4869135.
Armbrust et al. Clearing the clouds away from the true potential and obstacles posed by this computing capability. Communications of the ACM 53(4):50-58 (Apr. 2010).
Axopatch 2008 Patch Clamp: Theory and Operation, Axon Instruments, Inc., Mar. 1999.
Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.
Chen, et al., A novel nanofabrication technique for the array of Nanogap electrodes, Japanese Journal of Applied Physics, Japan Society of Applied physics, JP, 2006, 45(6):5531-5534.
Chen, et al., Probing Single DNA Molecule Transport Using Fabricated Nanopores, Nano Letters, 2004, 4(11):2293-2298.
Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.
Co-pending U.S. Appl. No. 16/156,755, filed Oct. 10, 2018.

(56) References Cited

OTHER PUBLICATIONS

Co-pending U.S. Appl. No. 16/169,756, filed Oct. 24, 2018.
Co-pending U.S. Appl. No. 16/178,924, filed Nov. 2, 2018.
El-Ali, et al., Simulation and experimental validation of a SU-8 based PCR themorcycler chp with integrated heaters and temperature sensor, Sensors and Actuators A, 110, 2004, pp. 3-10.
European search report and opinion dated Apr. 8, 2016 for EP Application No. 13879507.5.
Feng et al. "Nanopore-based Fourth-generation DNA Sequencing Technology" Genomics, Proteomics & Bioinformatics. 2015; 13(1):4-16, p. 5, col2, para 3.
Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.
Furuhashi et al. Denaturation of DNAs in a nanofluidic channel by micro-heating method. The 74th Annual Meeting of the Japan Society of Applied Physics Lecture Papers p. 12-295 (Aug. 2013).
Furuhashi et al. Denature of double-stranded DNAs by a micro-heating method. Proceedings of the 60th Spring Science Lecture Meeting of the Japan Society of Applied Physics, p. 12-356, (Mar. 2013).
Garcia-Lekue et al. Plane-wave-based electron tunneling through Au nanojunctions: Numerical calculations. Physical Review B 82:035410 (2010). 9 pages.
Gierhart, et al. Nanopore with transverse nanoelectrodes for electrical characterization and sequencing of DNA. Sens Actuators B Chem. Jun. 16, 2008;132(2):593-600.
Gonzalez, et al. Mass transport effect of mesoscopic domains in the amperometric response of an electroactive species: Modeling for its applications in biomolecule detection. Sensors and Actuators B: Chemical 144.2 (2010): 349-353.
Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.
He, et al. Controlling DNA translocation through gate modulation of nanopore wall surface charges. ACS Nano. Jul. 26, 2011;5(7):5509-18. doi: 10.1021/nn201883b. Epub Jun. 17, 2011.
He, et al. Gate manipulation of DNA capture into nanopores. ACS Nano. Oct. 25, 2011;5(10):8391-7. doi: 10.1021/nn203186c. Epub Sep. 26, 2011.
He, et al. Thermophoretic manipulation of DNA translocation through nanopores. ACS Nano. Jan. 22, 2013;7(1):538-46. doi: 10.1021/nn304914j. Epub Dec. 10, 2012.
Healy et al. Fabrication and characterization of nanopores with insulated transverse nanoelectrodes for DNA sensing in salt solution. Electrophoresis 33(23) (Dec. 2012). doi: 10.1002/elps.201200350. 15 pages.
International search report and written opinion dated May 19, 2015 for PCT/JP2015/054796.
International search report and written opinion dated Jun. 24, 2015 for PCT/JP2015/052601.
International search report and written opinion dated Aug. 11, 2015 for PCT/JP2015/063403.
International search report and written opinion dated Aug. 18, 2015 for PCT/JP2015/063963.
International search report and written opinion dated Aug. 18, 2015 for PCT/JP2015/063964.
International search report and written opinion dated Aug. 18, 2015 for PCT/JP2015/063965.
International Search Report and Written Opinion dated Dec. 6, 2016 for International Application No. PCT/JP2016/004531.
Ivanov, et al. DNA tunneling detector embedded in a nanopore. Nano Lett. Jan. 12, 2011;11(1):279-85. doi: 10.1021/nl103873a. Epub Dec. 6, 2010.
Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.
Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.
Nam, et al. Ionic field effect transistors with sub-10 nm multiple nanopores. Nano Lett. May 2009;9(5):2044-8. doi: 10.1021/nl900309s.
Notice of allowance dated Jul. 17, 2015 for U.S. Appl. No. 13/992,328.
Notice of allowance dated Jul. 21, 2016 for U.S. Appl. No. 13/975,610.
Notice of allowance dated Sep. 15, 2016 for U.S. Appl. No. 14/421,809.
Notice of allowance dated Oct. 8, 2015 for U.S. Appl. No. 13/992,328.
Notice of Allowance dated Dec. 6, 2016 for U.S. Appl. No. 15/061,871.
Office action dated Feb. 5, 2016 for U.S. Appl. No. 14/112,189.
Office action dated Feb. 19, 2016 for U.S. Appl. No. 13/975,610.
Office action dated Apr. 17, 2015 for U.S. Appl. No. 13/992,328.
Office action dated May 25, 2016 for U.S. Appl. No. 14/421,809.
Office action dated Jun. 23, 2016 for U.S. Appl. No. 14/111,352.
Office action dated Aug. 1, 2016 for U.S. Appl. No. 14/112,189.
Office action dated Aug. 26, 2016 for U.S. Appl. No. 14/687,856.
Office action dated Sep. 9, 2016 for U.S. Appl. No. 15/061,871.
Office Action dated Jan. 27, 2017 for U.S. Appl. No. 14/111,352.
Ohshiro, et al. Single-molecule electrical random resequencing of DNA and RNA. Scientific Reports 2, Article No. 501 (Jul. 10, 2012) doi:10.1038/srep00501.
Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.
Qiu, et al. Detecting ssDNA at single-nucleotide resolution by sub-2-nanometer pore in monoatomic graphene: A molecular dynamics study. Applied Physics Letters 100.8 (2012): 083106. 4 pages.
Rothberg, et al. An integrated semiconductor device enabling non-optical genome sequencing. Nature. 475 (2011): 348-352.
Schreiber et al. "Error rates for nanopore discrimination among cytosine, methylcytosine, and hydroxymethylcytosine along individual DNA strands" PNAS, 2013; 11 0(47): 18910-18915, p. 18910, col. 2, para 3.
Smith, et al. Electrophoretic distributions of human peripheral blood mononuclear white cells from normal subjects and from patients with acute lymphocytic leukemia. Proc Natl Acad Sci U S A. Jul. 1976;73(7):2388-91.
Tsutsui et al. Electrical Detection of Single-Methylcytosines in a DNA Oligomer. J Am Chem Soc 133(23): 9124-9128 (May 11, 2011). DOI: 10.1021/ja203839e.
Suga et al. Influence of electrode size on resistance switching effect in nanogap junctions, Applied Physics Letter, 2010, 97(7):73118, 4 pages. Epub Aug. 20, 2010.
Troisi, et al. Molecular signatures in the transport properties of molecular wire junctions: what makes a junction "molecular"? Small. Feb. 2006;2(2):172-81.
Tsutsui, et al., Formation and self-breaking mechanism of stable atom-sized junctions, NANO Letters, 2008, 8(1):345-349.
Tsutsui et al. Supplementary Information for Identifying Single Nucleotides by Tunneling Current. Nature Nanotechnology 5:286-290 (Mar. 21, 2010). doi: 10.1038/NNANO.2010.42.
Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.
Tsutsui, et al. Transverse electric field dragging of DNA in a nanochannel. Sci Rep. 2012;2:394. doi: 10.1038/srep00394. Epub May 3, 2012. 7 pages.
Venkatesan, et al. Nanopore sensors for nucleic acid analysis. Nat Nanotechnol. Sep. 18, 2011;6(10):615-24. doi: 10.1038/nnano.2011.129.
Woolley, et al. Capillary electrophoresis chips with integrated electrochemical detection. Analytical Chemistry 70.4 (1998): 684-688.

(56) References Cited

OTHER PUBLICATIONS

Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.
Bagci, et al. Recognizing nucelotides by cross-tunneling currents for DNA sequencing. Physical Review E, vol. 84, Issue No. 1, Article No. 011917 (internal pp. 1-4) (2011).
Brown, et al. Nucleotide-Surface Interactions in DNA-Modified Au-Nanoparticle Conjugates: Sequence Effects on Reactivity and Hybridization. J. Phys. Chem. C, 2008, 112 (20), pp. 7517-7521.
Chang, et al. Tunnelling readout of hydrogen-bonding-based recognition. Nature Nantechnology, vol. 4, May 2009, pp. 297-301.
Clarke, et al. Continuous base identification for single-molecule nanopore DNA sequencing. Nat Nanotechnol. Apr. 2009;4(4):265-70. doi: 10.1038/nnano.2009.12. Epub Feb. 22, 2009.
Co-pending U.S. Appl. No. 14/687,856, filed Apr. 15, 2015.
Dekker, et al. Solid-state nanopores. Nature Nanotechnology, vol. 2, Apr. 2007, pp. 209-215.
Fischbein, et al. Sub-10 nm Device Fabrication in a Transmission Electron Microscope. American Chemical Society, Nano Letters, 2007, vol. 7, No. 5, pp. 1329-1337.
Fologea, et al. Detecting Single Stranded DNA with a Solid State Nanopore. American Chemical Society, Nano Letters, 2005, vol. 5, No. 10, pp. 1905-1909.
Furuhashi, et al. High speed DNA denaturation using microheating devices. Appl. Phys. Lett., Jul. 11, 2013, 103, pp. 023112.
He, et al. Identification of DNA Basepairing via Tunnel-Current Decay. American Chemical Society, Nano Letters, 2007, vol. 7, No. 12, pp. 3854-3858.
Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010.
International Preliminary Report on Patentability dated Jun. 25, 2013 for PCT Application No. JP2013/059645.
International search report and written opinion dated Jan. 26, 2015 for PCT Application No. US2014/060742.
International Search Report and Written Opinion dated Feb. 17, 2015 for PCT Application No. IB2014/002143.
International Search Report and Written Opinion dated Jun. 25, 2013 for PCT Application No. JP2013/059645.
International search report and written opinion dated Oct. 29, 2013 for PCT Application No. JP2013/071059.
International search report and written opinion dated Dec. 19, 2014 for PCT Application No. US2014/056173.
International Search Report and Written Opinion dated Feb. 24, 2015 for PCT Application No. IB2014/002128.
Kaji, et al. Separation of long DNA molecules by quartz nanopillar chips under a direct current electric field. Anal. Chem., Jan. 1, 2004, 76(1): pp. 15-22.
Keyser, et al. Direct force measurements on DNA in a solid-state nanopore. Nature Physics, vol. 2, Jul. 2006, pp. 473-477.
Lagerqvist, et al. "Fast DNA Sequencing via Transverse Electronic Transport", American Chemical Society, Nano Letters, 2006, vol. 6, No. 4, pp. 779-782.
Lagerqvist, et al. Influence of the Environment and Probes on Rapid DNA Sequencing via Transverse Electronic Transport. Biophysical Journel, vol. 93, Oct. 2007, pp. 2384-2390.
Li, et al. Ion-beam sculpting at nanometer length scales. Nature, vol. 412, Jul. 2001, pp. 166-169.
Liang, et al. Nanogap Detector Inside nanofluidic Channel for Fast Real-Time Label-Free DNA Analysis. American Chemical Society, Nano Letters 2008, vol. 8, No. 5, pp. 1472-1476.
Maleki, et al. A nanofluidic channel with embedded transverse nanoelectrodes. Nanotechnology, 20, (2009) 105302, pp. 1-6.
Mastrangelo, et al. The potential and challenges of nanopore sequencing. Nature Biotechnology. 26 (2008): 1146-1153.
Nadasan, et al. Design and fabrication of the microchannels for microfluidics applications. U.P.B. Sci. Bull., Series C, 2009, 71(4): pp. 125-134.
Office action dated Sep. 1, 2015 for U.S. Appl. No. 14/112,189.

Oshiro, et al. Detection of post-translational modifications in single peptides using electron tunnelling currents. Nature Nanotechnology, vol. 9, pp. 835-840 (e-pub. Sep. 14, 2014).
Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.
Pedone, et al. Data Analysis of Translocation Events in Nanopore Experiments. American Chemical Society, Anal. Chem. 2009, 81, pp. 9689.
Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
Ruitenbeek, et al. Adjustable nanofabricated atomic size contacts. Rev. Sci. Instrum. 67, 108 (1996).
Simmons, et al. Generalized Formula for the Electric tunnele Effect between Similar Electrodes Separated by a Thin Insulating Film. J. Appl. Phys. 34, 1793 (1963).
Stijin Van Dorp, et al. Origin of the electrophoretic force on DNA in solid-state nanopores. Nature Physics, vol. 5, May 2009, pp. 347-351.
Stoddart, et al. Single-nucleotide discrimination in immobilized DNA oligonucleotides with a biological nanopore. PNAS, May 12, 2009, vol. 106, No. 19, pp. 7702-7707.
Storm, et al. Fabrication of solid-state nanopores with single-nanometere precision. Nature Materials, vol. 2, Aug. 2003, pp. 537-540.
Taniguchi, et al. Denryu de Ichi Enki Bunshi o Shikibetsu suru. Chemistry, 2011, vol. 66, No. 8, pp. 42-46.
Taniguchi, et al. Development of Single-Molecule Bio-Nanodevices for Medical Applications. The Imaging Society of Japan, Feb. 10, 2013, vol. 52, No. 1, pp. 51-60.
Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.
Trepagnier, et al. Controlling DNA Capture and Progagation through Artificial Nanopores. American Chemical Society, Nano Letters, 2007, vol. 7, No. 9, pp. 2824-2830.
Tsutsui, et al. Fabrication of 0.5 nm electrode gaps using self-breaking technique. Applied Physics Letters 93, 163115 (2008); DOI: 10.1063/1.3006063.
Tsutsui, et al. Formation and self-breaking mechanism of stable atom-sized junctions. Nano Lett. Jan. 2008;8(1):345-9. Epub Dec. 21, 2007.
Tsutsui, et al. Identifying single nucleotides by tunnelling current. Nature Nanotechnology, Letters, Published Online: Mar. 21, 2010; DOI: 10.1038/NNANO.2010.42, pp. 1-5.
Tsutsui, et al. Transverse Field Effects on DNA-Sized Particle Dynamics. American Chemical Society, Nano Letters, 2009, vol. 9, No. 4, pp. 1659-1662.
Wang, et al. Mechanism of electron conduction in self-assembled alkanethiol monolayer devices. Phys. Rev. B 68, 035416—Published Jul. 17, 2003.
Yen, et al. Gate effects on DNA translocation through silicon dioxide nanopore. Rev Sci Instrum. Mar. 2012;83(3):034301. doi: 10.1063/1.3692746.
Zhou, et al. Microfabrication of a mechanically controllable break junction in silicon. Appl. Phys. Lett. 67, 1160 (1995).
Zwolak, et al. Colloquium: Physical approaches to DNA sequencing and detection. Reviews of Modern Physics, vol. 80, Jan.-Mar. 2008, pp. 141-165.
Zwolak, et al. Electronic Signature of DNA Nucleotides via Transverse Transport. American Chemical Society, Nano Letters, 2005, vol. 5, No. 3, pp. 421-424.
Ohshiro et al. Tunnel-Current based Single-Molecule Identification of DNA/RNA oligmer by using Nano-MCBJ. 2012 12th IEEE International Conference on Nanotechnology (IEEE-NANO), Birmingham, United Kingdom, (Aug. 20-23, 2012). 2 pages
Tang et al. Sub-10-nm nanogap fabrication by silicidation. 2013 13th IEEE International Conference on Nanotechnology (IEEE-NANO 2013). (Aug. 5-8, 2013). 4 pages. DOI: 10.1109/NANO.2013.6720811.

(56) References Cited

OTHER PUBLICATIONS

Taniguchi et al. Fabrication of the gating nanopore device. Applied Physics Letters 95:123701 (2009). 4 pages. DOI: https://doi.org/10.1063/1.3236769.

Si et al. Effect of nanopore size on poly(dT)30 translocation through silicon nitride membrane. Science China Technological Sciences, vol., 56, No. 10, pp. 2398-2402 (Oct. 2013). doi: 10.1007/s11431-013-5330-2. Published online Aug. 21, 2013.

* cited by examiner

FIG.10
DEOXYTHYMIDINE 5'-
MONOPHOSPHATE
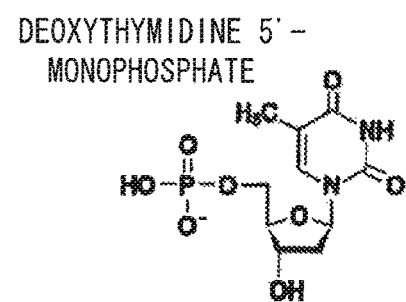
ADENOSINE 5'-
MONOPHOSPHATE
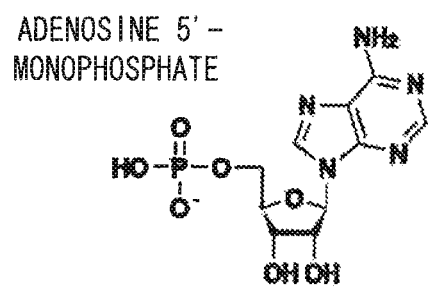
GUANOSINE 5'-
MONOPHOSPHATE
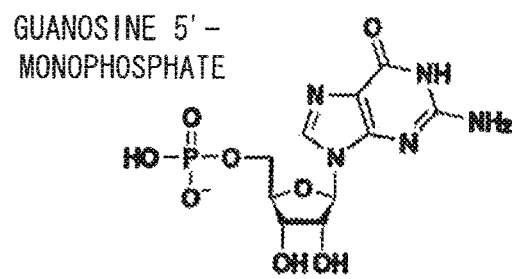
CYTIDINE 5'-
MONOPHOSPHATE
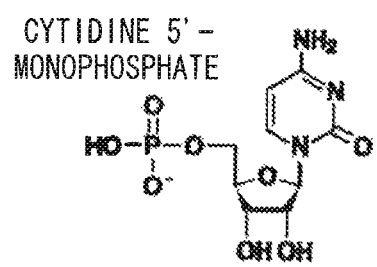

FIG.12
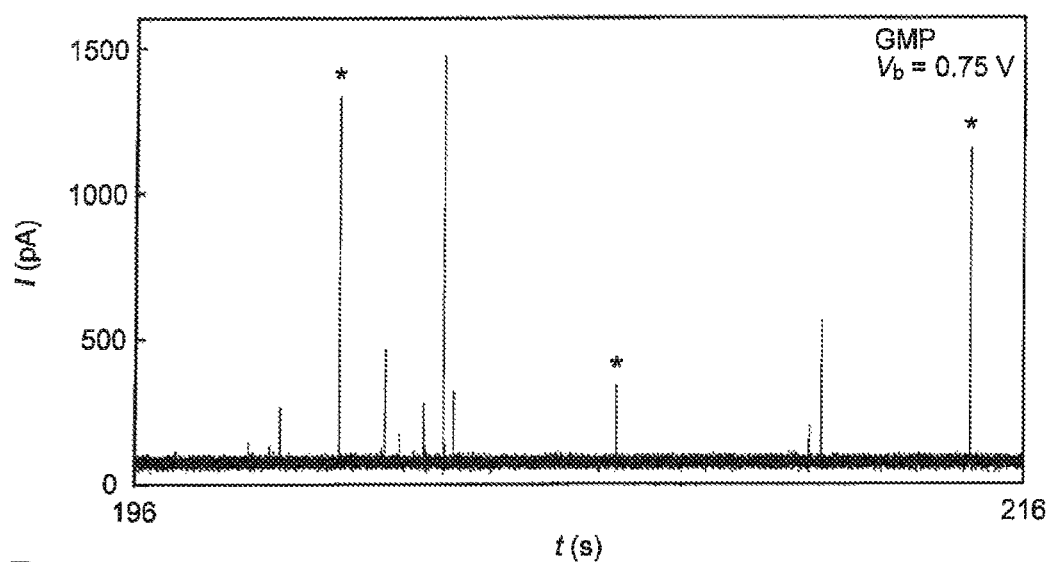
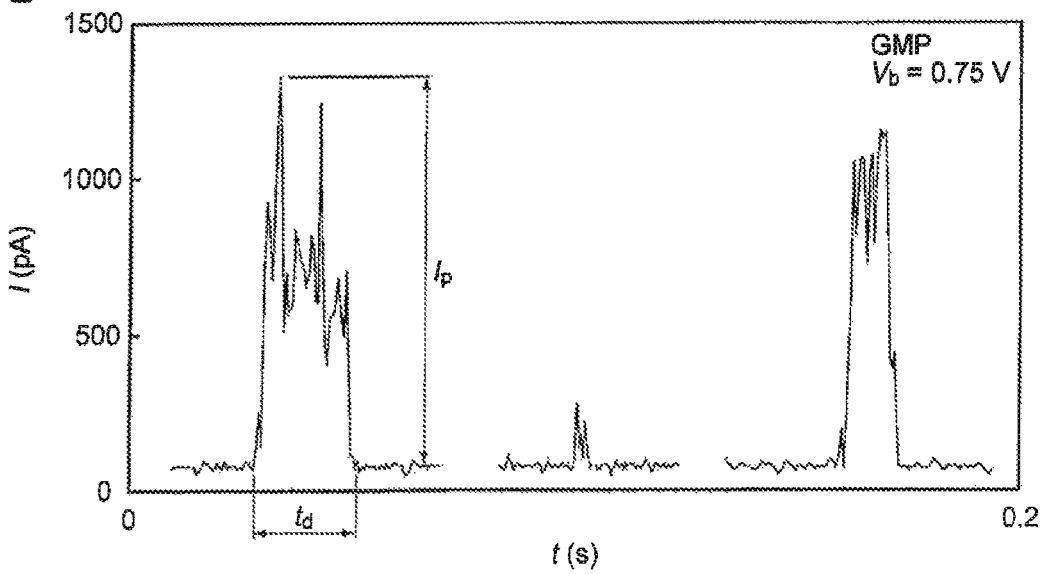

METHOD AND DEVICE FOR IDENTIFYING NUCLEOTIDE, AND METHOD AND DEVICE FOR DETERMINING NUCLEOTIDE SEQUENCE OF POLYNUCLEOTIDE

CROSS-REFERENCE

This application is a Continuation of U.S. patent application Ser. No. 14/883,494, filed Oct. 14, 2015, which is a Continuation of U.S. patent application Ser. No. 13/992,328, filed Oct. 16, 2013, now U.S. Pat. No. 9,194,838, which is a National Stage Entry of International Patent Application No. PCT/JP2011/054631, filed on Mar. 1, 2011, which claims the benefit of U.S. Provisional Patent Application No. 61/310,215, filed on Mar. 3, 2010, each of which is incorporated herein by reference in its entirety.

TECHNICAL FIELD

The present invention relates to a method and a device that identify a nucleotide by analyzing the nucleotide using current measurements. The present invention, moreover, relates to a method and a device that determine the nucleotide sequence of a polynucleotide using current measurements.

BACKGROUND ART

Technology to analyze nucleotide base sequences of DNA is not simply limited to the academic research field, but is applied in fields ranging from medicine to drug discovery and criminal forensics, and there is increasing interest in developments in this technology.

Conventional DNA sequencers that have been developed hitherto employ optical measuring techniques to identify fluorescent markers added to nucleotides, rather than directly identifying the nucleotides themselves. In order to attach a marker to a nucleotide, it is necessary to use PCR to chemically modify the nucleotide. This process not only requires a large number of reagents, but is also very time consuming. Serious funding and time are, therefore, required in order to perform DNA sequencing.

Against this backdrop, over the past several decades there has been striking progress in DNA sequencing technology based on single molecules as a step towards individual genome sequencing. One recent example of an outstanding achievement brought about by this progress is a detector employing nanoscale pores (referred to below as nanopores) of chemically designed α-hemolysin (see Non-Patent Documents 1 to 5).

This detector enables sequencing to be performed on a single DNA molecule by detecting temporary ion current blocking that occurs when an oligomer of a single strand of DNA passes through an embedded biological nanopore in cyclodextrin (see Non-Patent Documents 6, 7). Such strong and solid state nanopores capable of being structured are attracting attention, and play a role as platforms for researching the dynamics of single biomolecules passing through pores (see Non-Patent Documents 1, 2, 8 to 11). However, there are issues in that DNA sequencing based on ion currents employing the above detector is (1) limited in pore size selection, and is (2) an unstable system, such that there is no real prospect of application of sequencers employing biological nanopores. Research into DNA sequencing with a resolution of one molecule based on an ion current is still ongoing (see Non-Patent Documents 3, 4).

A theory of sequencing based on transverse electron transport has been proposed as an alternative to ion current based DNA sequencing. As illustrated in FIG. 21, this theory is based on a principle of detecting transverse conductivity distinct to each nucleotide when a nucleotide passes through a nanoscale space between a pair of electrodes (this conductivity is related to differences in gaps between the HOMO and the LUMO of each nucleotide). Specifically, during passage of single DNA through a nanopore, a tunnel current occurs through each nucleotide between a pair of electrodes provided at the nanopore edges with a nanoscale inter-electrode distance (referred to below as the "nanoelectrode pair"). It is thought that by measuring the current value of the tunnel current, direct reading of the nucleotide sequence based on the current value is possible without marking.

It is anticipated that were such transverse electron transport based sequencing to be performed, it would be possible to directly read the nucleotide sequence of a single DNA molecule at an extremely high sequencing speed in excess of 400 kilobases per hour (see Non-Patent Documents 5, 12, 13). Based on such theoretical anticipations, a number of groups have developed systems in order to demonstrate these predictions by embedding nanoelectrode pairs in fluid channels with sizes in micrometers or nanometers (see Non-Patent Documents 16 to 19).

Non-Patent Document 1: J. Li, D. Stein, C. McMullan, D. Branton, M. J. Aziz, J. A. Golovchenko, Nature 412, 166 (2001)

Non-Patent Document 2: A. J. Storm, J. H. Chen, X. S. Ling, H. W. Zandbergen, C. Dekker, Nature Mat. 2, 537 (2003)

Non-Patent Document 3: C. Dekker, Nat. Nanotechnol. 2, 209 (2007)

Non-Patent Document 4: D. Branton, D. W. Deamer, A. Marziali, H. Bayley, S. A. Benner, T. Butler, M. Di Ventra, S. Garaj, A. Hibbs, X. Huang, S. B. Jovanovich, P. S. Krstic, S. Lindsay, X. S. Ling, C. H. Mastrangelo, A. Meller, J. S. Oliver, Y V Pershin, J. M. Ramsey, R. Riehn, G. V. Soni, V. Tabard-Cossa, M. Wanunu, M. Wiggin, J. A. Schloss, Nat. Biotech. 26, 1146 (2008)

Non-Patent Document 5: M. Zwolak, M. Di Ventra, Rev. Mod. Phys. 80, 141 (2008)

Non-Patent Document 6: J. Clarke, H.-C. Wu, L. Jayasinghe, A. Patel, S. Reid, H. Bayley, Nat. Nanotechnol. 4, 265 (2009)

Non-Patent Document 7: D. Stoddart, A. J. Heron, E. Mikhailova, G. Maglia, H. Bayley, Proc. Natl. Acad. Sci. USA 106, 7702 (2009)

Non-Patent Document 8: D. Fologea, M. Gershow, B. Ledden, D. S. McNabb, J. A. Golovchenko, Li J., Nano Lett. 5, 1905 (2005)

Non-Patent Document 9: U. F. Keyser, B. N. Koeleman, S. V. Dorp, D. Krapf, R. M. M. Smeets, S. G. Lemay, N. H. Dekker, C. Dekker, Nat. Phys. 2, 473 (2006)

Non-Patent Document 10: E. H. Trepagnier, A. Radenovic, D. Sivak, P. Geissler, J. Liphardt, Nano Lett. 7, 2824 (2007)

Non-Patent Document 11: S. van Dorp, U. F. Keyser, N. H. Dekker, C. Dekker, S. G. Lemay, Nat. Phys. 5, 347 (2009)

Non-Patent Document 12: M. Zwolak, M. Di Ventra, Nano Lett. 5, 421 (2005)

Non-Patent Document 13: J. Lagerqvist, M. Zwolak, M. Di Ventra, Byophys. J. 93, 2384 (2007)

Non-Patent Document 14: J. He, L. Lin, P. Zhang, S. Lindsay, Nano Lett. 7, 3854 (2007)

Non-Patent Document 15: S. Chane, J. He, A. Kibel, M. Lee, 0. Sankey, P. Zhang, S. Lindssay, Nat. Nanotechnol. 4, 297 (2009)

Non-Patent Document 16: M. D. Fischbein, M. Drndic, Nano Lett. 7, 1329 (2007)

Non-Patent Document 17: X. Liang, S. Y. Chou, Nano Lett. 8, 1472 (2008)

Non-Patent Document 18: T. Maleki, S. Mohammadi, B. Ziaie, Nanotechnol. 20, 105302 (2009)

Non-Patent Document 19: M. Tsutsui, M. Taniguchi, T. Kawai, Nano Lett. 9, 1659 (2009)

SUMMARY

Technical Problem

However, as described above, although systems have been developed in order to demonstrate the principles of sequencing based on transverse electron transport, even when the same nucleotides are employed, fluctuation in the values of the tunnel current occurs at each measurement, such that it is not possible to identify the nucleotide with this value as an indicator. In addition to the inability to identify nucleotides, it has not been possible to determine the nucleotide sequence of polynucleotides configured from plural nucleotides.

In consideration of the above circumstances, an object of the present invention is to identify a nucleotide, and to determine the nucleotide sequence of polynucleotides, using current measurements.

Solution to Problem

The present inventors have discovered that values obtained by statistical analysis of maximum current values of pulses in tunnel current that change with each measurement are values that are specific to each nucleotide. They have then discovered that these values can be employed as indicators to identify nucleotides, leading to the completion of the present invention. There has been absolutely no attention given to such statistical analysis in conventional technology.

Namely, a method of identifying a nucleotide of the present invention includes: a process of passing a nucleotide between electrodes plural times; a process of detecting pulses of a tunnel current arising between the electrodes as the nucleotide passes through; a process of calculating a modal value of the maximum current value of each pulse; and a process of comparing the calculated modal value against a reference value.

A device that identifies a nucleotide of the present invention includes: an electrode pair with an inter-electrode distance through which a nucleotide is able to pass; an application means that applies a voltage between the electrodes; a detection means that detects pulses of a tunnel current arising between the electrodes; a calculation means that calculates a modal value of the maximum current value of each pulse; and a comparison means that compares the calculated modal value against a reference value.

A method of determining the nucleotide sequence of a polynucleotide of the present invention includes: a process of passing a polynucleotide between electrodes; a process of measuring current values of a tunnel current arising between the electrodes as the polynucleotide passes through; a process of calculating a modal value of the measured current values; a process of normalizing the modal value of the current values by dividing the modal value of the current values by a modal value of a standard nucleotide; and a process of comparing the normalized modal value against a reference value. The modal value of the standard nucleotide is acquired by passing the standard nucleotide between the electrodes plural times, detecting pulses of a tunnel current arising between the electrodes as the standard nucleotide passes through, and calculating a modal value of the maximum current value of each pulse.

A device that determines the nucleotide sequence of a polynucleotide of the present invention includes: an electrode pair with an inter-electrode distance through which a polynucleotide is able to pass; an application means that applies a voltage between the electrodes; a measurement means that measures current values of a tunnel current arising between the electrodes; a calculation means that calculates a modal value of the measured current values; a normalizing means that normalizes the modal value of the current values by dividing the modal value of the current values by a modal value of a standard nucleotide; and a comparison means that compares the normalized modal value against a reference value. The modal value of the standard nucleotide is acquired by passing the standard nucleotide between the electrodes plural times, detecting pulses of a tunnel current arising between the electrodes as the standard nucleotide passes through, and calculating a modal value of the maximum current value of each pulse.

Advantageous Effects of Invention

The present invention enables a nucleotide to be identified directly and rapidly without marking. The present invention also enables the nucleotide sequence of a polynucleotide to be determined directly and rapidly without marking.

BRIEF DESCRIPTION OF DRAWINGS

FIG. 10 is a diagram illustrating molecular structure of nucleotides that are employed in a present Example.

FIG. 12 shows graphs illustrating curves (referred to below as "I–t curves") expressing relationships between tunnel current (I) and time (t) obtained when guanosine monophosphate (GMP) is employed as the nucleotide.

DESCRIPTION OF EMBODIMENTS

Figure 1:
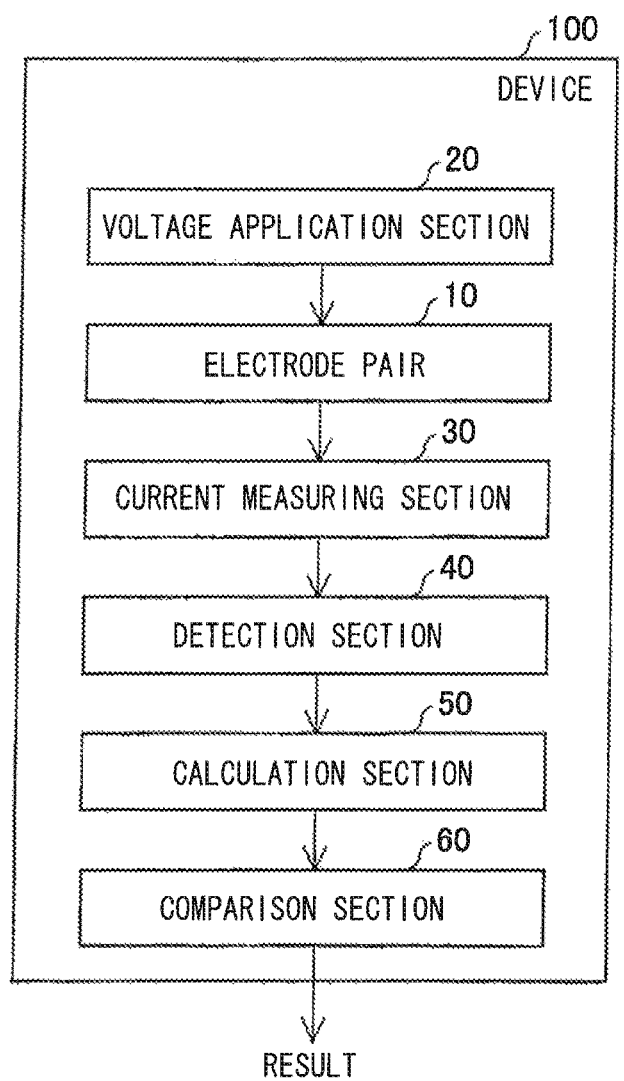
FIG. 1 is a function block diagram schematically illustrating an example of a device of the present invention.

The present invention provides a technique for identifying a single nucleotide, and a technique for employing this technique to determine the nucleotide sequence of a polynucleotide. Explanation follows regarding an exemplary embodiment of these techniques, however the present invention is not limited thereto.

1. Nucleotide Identification Method

The present invention provides a method of nucleotide identification. The nucleotide identification method includes: a process of passing a nucleotide between electrodes plural times; a process of detecting pulses of a tunnel current arising between the electrodes as the nucleotide passes through; a process of calculating a modal value of the maximum current value of each pulse; and a process of comparing the calculated modal value against a reference value.

Rather than identifying a nucleotide to which a marker has been attached, the present invention enables the nucleotide to be directly identified based on electrical characteristics (the modal value of the maximum current value) of the nucleotide. Identification of the nucleotide can accordingly be performed quickly and at low cost.

In conventional sequencing, there is a requirement for PCR and a chemical reaction to attach a marker to a nucleotide, such that chemically stable DNA in a polynucleotide is targeted. Since such chemical reactions are not necessary in the present invention, not only deoxyribonucleic acid in DNA, but also ribonucleic acid in chemically unstable RNA can be the target for identification. Sequencing targeting not only DNA but also RNA can accordingly be achieved by applying the present invention in sequencing.

In order to implement the present exemplary embodiment a tunnel current needs to be generated between the electrodes when a nucleotide passes through. The distance between the electrodes is important for generating such a tunnel current. When the distance between the electrodes is excessively longer than the molecular diameter of the nucleotide, tunnel current does not readily flow between the electrodes, or two or more nucleotides enter between the electrodes at the same time. However the nucleotide no longer enters between the electrodes in the opposite case when the distance between the electrodes is excessively shorter than the molecular diameter of each of the nucleotide.

It becomes difficult to detect pulses caused by tunnel current across a single molecule of the nucleotide when the distance between the electrodes is excessively longer or excessively shorter than the molecular diameter of the nucleotide. Moreover, even if the whole of a molecule does not enter between the electrodes, a tunnel current flows as long as a portion of the nucleotide is between the electrodes. The distance between the electrodes is hence preferably made slightly shorter than, or the same as, or slightly longer than the molecular diameter of the nucleotide. For example, the inter-electrode distance is a length that is 0.5 times to 2 times the molecular diameter of the nucleotides, with the inter-electrode distance preferably set at a length of 1 times to 1.5 times thereof, and more preferably set at a length of 1 times to 1.2 times.

Since the molecular diameter of the nucleotides is known to a person of skill in the art, appropriate selection of the optimum distance between the electrodes can be made by a person of skill in the art by reading the present specification. For example, since the molecular diameter of nucleotides in a monophosphate state is about 1 nm, in order to flow a tunnel current through such a nucleotide the distance between the electrodes is, for example, set at 0.5 nm to 2 nm, preferably at 1 nm to 1.5 nm and more preferably at 1 nm to 1.2 nm.

When electrodes are too large, even when the inter-electrode distance is configured as described above, 2 or more nucleotide molecules may be trapped between the electrodes. For example, when the length of the electrodes in the nucleotide passing direction or the length of the electrodes in a direction orthogonal to a plane formed by the direction between the electrodes and the nucleotide passing direction is excessively longer than the nucleotide molecular diameter, 2 or more nucleotide molecules may be trapped between the electrodes even when the inter-electrode distance is configured as described above. When 2 or more nucleotide molecules are trapped between the electrodes, a tunnel current flows through the 2 molecules such that it becomes difficult to measure the tunnel current through a single molecule. Accordingly, the size of the electrodes is preferably set at a level that is slightly shorter than the nucleotide molecular diameter, the same as the nucleotide molecular diameter, or slightly longer than the nucleotide molecular diameter.

The above electrode pairs can be easily fabricated using a known nanofabricated mechanically-controllable break junction method. A nanofabricated mechanically-controllable break junction method is an excellent method capable of controlling of the inter-electrode distance with excellent mechanical stability at resolution at the picometer level or finer. Fabrication methods for electrode pairs employing nanofabricated mechanically-controllable break junction methods are described for example in J. M. van Ruitenbeek, A. Alvarez, I. Pineyro, C. Grahmann, P. Joyez, M. H. Devoret, D. Esteve, C. Urbina, Rev. Sci. Instrum. 67, 108 (1996) and M. Tsutsui, K. Shoji, M. Taniguchi, T. Kawai, Nano Lett. 8, 345 (2008). An appropriate metal such as gold may be employed as the electrode material.

For example, the electrode pair may be fabricated using the process set out below.

Firstly, known electron beam lithography and lift-off technology is used to pattern form nanoscale gold junctions on a polyimide coated flexible metal substrate employing an electron beam lithography device (JEOL Ltd., catalogue number: JSM6500F). Next, polyimide beneath the junctions is removed by etching based on a known etching process (for example a reactive ion etching process) employing a reactive ion etching device (Samco Inc., catalogue number: 10NR).

A nanoscale gold bridge structure with a 3-point bent structure is then fabricated by bending the substrate. Here, precise bending of the substrate is performed employing a piezoelectric actuator (CEDRAT, catalogue number: APA150M), enabling the inter-electrode distance of the electrode pair to be controlled at resolution at the picometer level or finer.

Next, a portion of the bridge is broken by pulling the fabricated bridge. The bridge is pulled further, and the size of the gap (inter-electrode distance) occurring due to the break is set to the length (about 1 nm) of the target nucleotide molecule. When this is performed, the inter-electrode distance of the electrode pair may be accurately controlled by regulating the bridge pulling employing self-breaking technology developed in the research department of the inventors of the present invention (see for example M. Tsutsui, K. Shoji, M. Taniguchi, T. Kawai, Nano Lett. 8, 345 (2008) and M. Tsutsui, M. Taniguchi, T. Kawai, Appl. Phys. Lett. 93, 163115 (2008)).

Specifically, a DC bias voltage ($V_b$) of 0.1V is applied to the bridge employing series resistance of 10 kΩ at a programmed junction stretching speed, pulling the gold nanojunction, and breaking the bridge by a resistance feedback method (see M. Tsutsui, K. Shoji, M. Taniguchi, T. Kawai, Nano Lett. 8, 345 (2008), and M. Tsutsui, M. Taniguchi, T. Kawai, Appl. Phys. Lett. 93, 163115 (2008)) employing a data acquisition board (National Instruments Corporation, catalogue number: NI PCIe-6321). Next, the bridge is pulled further and the size of the gap (inter-electrode distance) occurring due to the break is set to the length of the target nucleotide molecule. The electrode pair is thereby formed.

By employing the technology described above, the nano-electrode pair can be fabricated with good reproducibility with the inter-electrode distance after the contact between single atoms has been made to self-break distributed in a narrow range of 0.6 nm±0.05 nm.

The nucleotides for identification by the present invention are not particularly limited, and may be appropriate ribonucleotides or appropriate deoxynucleotides. Ribonucleotides are not particularly limited, and may include for example: adenosine monophosphate (AMP), adenosine diphosphate (ADP), adenosine triphosphate (ATP), guanosine monophosphate (GMP), guanosine diphosphate (GDP), guanosine triphosphate (GTP), cytidine monophosphate (CMP), cytidine diphosphate (CDP), cytidine triphosphate (CTP), uridine monophosphate (UMP), uridine diphosphate (UDP), and uridine triphosphate (UTP). Deoxyribonucleotides are not particularly limited, and may include for example: deoxyadenosine monophosphate (dAMP), adenosine deoxydiphosphate (dADP), deoxyadenosine triphosphate (dATP), deoxyguanosine monophosphate (dGMP), deoxyguanosine diphosphate (dGDP), deoxyguanosine triphosphate (dGTP), deoxycytidine monophosphate (dCMP), deoxycytidine diphosphate (dCDP), deoxycytidine triphosphate (dCTP), deoxyuridine monophosphate (dUMP), deoxyuridine diphosphate (dUDP), deoxyuridine triphosphate (dUTP), deoxythymidine monophosphate (dTMP), deoxythymidine diphosphate (dTDP), and deoxythymidine triphosphate (dTTP).

Further explanation follows regarding each process.

In the "process of passing a nucleotide between electrodes" of the present invention, for example the electrode pair described above may be held in a solution in which a nucleotide has been dissolved. By thus holding the electrode pair in the solution, the nucleotide can be passed between the electrodes plural times employing the spontaneous movement of the nucleotide in the solution.

There is no particular limitation to the solvent in which the nucleotide is dissolved, however for example ultrapure water may be employed. Ultrapure water can, for example, be produced employing a Milli-Q Integral 3 (device name) made by EMD Millipore Corporation (Milli-Q Integral 3/5/10/15 (catalogue number)). Water produced using this device is referred to as Mili-Q water in the present specification. The concentration of the nucleotide in the solution is not particularly limited, however is for example 5 μM.

Then, by holding the electrode pair in the solution in which the nucleotide is dissolved and applying a voltage between the electrodes, a nucleotide becomes trapped between the electrodes as the nucleotide passes. A tunnel current arises between the electrodes during the interval in which the nucleotide is trapped between the electrodes (in the interval during which the nucleotide is present between the electrodes). The nucleotide trapped between the electrodes then spontaneously moves away from the electrodes after a specific period of time has elapsed. The tunnel current arising between the electrodes then disappears due to the nucleotide moving away from the electrodes. A pulse in tunnel current accordingly arises due to the nucleotide being trapped between the electrodes, and then moving away from between the electrodes. Note that since the period of time during which he nucleotide is trapped between the electrodes is extremely short, the phrase "nucleotide passes between the electrodes" and the phrase "the nucleotide is trapped between the electrodes and then moves away from the electrodes" mean the same in the present specification.

There is no particular limitation to the method for applying voltage between the electrodes, and for example a known power supply device may be connected to the electrodes, and a voltage applied between the electrodes (for example a bias voltage). The voltage applied is not particularly limited, however may for example be from 0.25V to 0.75V.

In the "process of detecting pulses of a tunnel current arising between the electrodes as the nucleotide passes through" of the present invention, for example a voltage may be applied in this manner between the electrodes held in the solution in which the nucleotide is dissolved, and the current value of the tunnel current arising between the electrodes may be measured for a specific duration. For example, the current value of the tunnel current may be measured for example for 50 minutes.

In the present specification, a "tunnel current pulse caused by the nucleotide" refers to a tunnel current signal from the tunnel current rising above a base level until the tunnel current once again returns to the base level during measurement of the tunnel current for the specific duration (see B in FIG. 12, described later). The increase in the tunnel current indicates that the nucleotide is trapped between the electrodes, and the return of the tunnel current to the base level indicates that the trapped nucleotide has moved away from between the electrodes. In the present specification, "base level" refers to an average noise value. "Noise" refers to a tunnel current signal observed when a nucleotide is not trapped between the electrodes. For example, noise can be obtained by measuring the current value of tunnel current arising when a voltage is applied between the electrodes that are being held in a solution in which no nucleotide has been dissolved.

The measurement of the current value of the tunnel current arising between the electrodes may be measured employing a known ammeter. The tunnel current signal may moreover be first amplified employing for example a current amplifier. Since employing a current amplifier enables amplification of weak tunnel current values, it is possible to measure the tunnel current with high sensitivity. An example of a current amplifier is commercially available variable gain high speed current amplifier (Catalogue Number: DHPCA-100, manufactured by FEMTO Messtechnik GmbH).

Note that, as explained in an exemplary embodiment described later, the inventors of the present invention read an amplified current signal with a frequency in excess of 1 kHz after amplifying a picoampere level current using a homemade logarithmic amplifier. The thus amplified current signal may be recorded on a computer at for example a 2 kHz sampling rate using a 24-bit resolution DAQ card (National Instruments Corporation, catalogue number: NI USB-9234).

The tunnel current pulse can accordingly be detected by measuring the current value of the tunnel current flowing between the electrodes for the specific duration, and serially determining whether or not the current value of the tunnel current exceeds a base level. Specifically, according to the determination referred to above, by identifying the time when the tunnel current exceeds the base level and by identifying the time when the tunnel current returns once again to the base level, the signal in the period between these two times can be detected as a tunnel current pulse caused by the nucleotide. Employing a graph expressing a relationship between the measured current value of the tunnel current and the tunnel current measurement duration (for example a curve graph) enables such determination to be easily performed by visual inspection.

There are various heights of peak present in the pulses caused by the thus detected nucleotides. These peaks appear due to changes in the distance between the electrodes and the nucleotide according to the movement of the nucleotide between the electrodes. Namely, since tunnel current readily arises when the distance between the nucleotide and the electrodes is short, the current value of the tunnel current increases. However, since tunnel current does not readily arise when the distance between the nucleotide and the electrodes is long, the current value of the tunnel current decreases. There are accordingly changes in the distance between the electrodes and the nucleotide and increases and decreases in the current values of the tunnel current caused by movement of the reference nucleotide between the electrodes, and hence plural various peaks appear in the pulse of the tunnel current.

In the "process of calculating a modal value of the maximum current value of each pulse" of the present invention, the "maximum current value of each pulse" may be derived by subtracting the base level from the highest peak current value in each thus detected pulse. A modal value may be calculated by performing statistical analysis on the derived maximum current value.

For example, each pulse may be categorized based on maximum current value, and the modal value may be calculated based on the number and maximum current values of the pulses belonging to each categorized group.

"Categorizing each pulse based on maximum current value" may for example involve categorizing pulses that have the same maximum current value, or substantially the same maximum current value, into the same group, or may involve categorizing pulses belonging to a range of maximum current values of a given width into the same group. Note that "pulses that have substantially the same maximum current value" refers to pulses with a maximum current value differing by several % from a particular maximum current value. For example, "pulses that have substantially the same maximum current value" refers to pulses with a maximum current value of between 90% and 110% of a particular maximum current value.

More specifically, the modal value may be calculated as explained below. Firstly, a histogram is generated that expresses a relationship between the maximum current value of each pulse and the number of pulses corresponding to the maximum current values. The generated histogram is fitted to a specific function.

The modal value may then be calculated by deriving a peak value of the fitted function. The function employed in fitting may be a Gaussian function or a Poisson function, and is preferably a Gaussian function. Employing a Gaussian function has the advantage of enabling the data processing speed to be made faster.

In the present process, the number of samples (pulses) employed in the statistical analysis in order to calculate the modal value is not particularly limited, and is for example between 500 and 1000 individual samples. Employing a number in this region for statistical analysis enables calculation of a statistically meaningful modal value. Since such modal values are distinct values to each nucleotide, these modal values may be employed as indicators for nucleotide identification.

Figure 16:
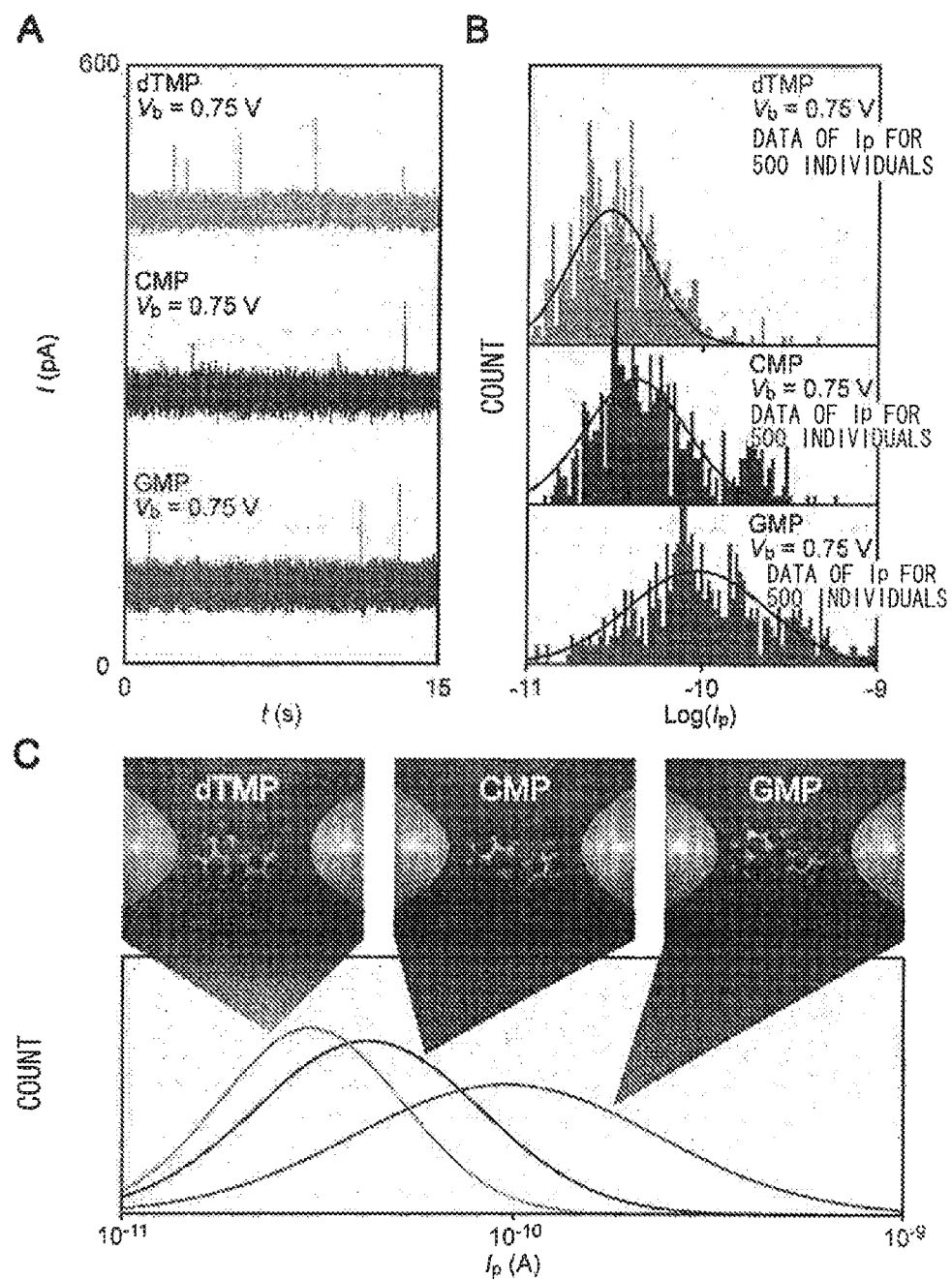
FIG. 16 is a diagram explaining statistical identification of a single nucleotide.

In the exemplary embodiment described later, and as illustrated in B and C of FIG. 16, the inventors of the present invention demonstrate that the modal values for GMP, dTMP and CMP are respectively 96 pA, 30 pA and 42 pA (note that these modal values were calculated under conditions of an inter-electrode distance of 1 nm, a bias voltage of 0.75V and with the number of samples for statistical analysis set at (500)). Moreover, as illustrated in A and B of FIG. 17, the modal values of dCMP, dGMP, dAMP, dTMP, CMP, GMP, AMP and UMP were respectively demonstrated to be 60 pS, 87 pS, 67 pS, 39 pS, 64 pS, 123 pS, 92 pS, and 50 pS (note that that these modal values were calculated under conditions of an inter-electrode distance of 0.8 nm, a bias voltage of 0.4V and with the number of samples for statistical analysis set at (1000)). Since the modal values are distinct values for each nucleotide, these modal values may accordingly be employed as indicators for nucleotide identification.

In the "process of comparing the calculated modal value against a reference value" of the present invention, the modal values calculated in the above process may be compared against a reference value relating to a known nucleotide (referred to below as "reference nucleotide").

Note that the tunnel current is heavily influenced by the inter-electrode distance, the concentration of the nucleotide or the polynucleotide in the solution, the shape of the fabricated electrodes, voltage, and the number of samples for statistical analysis, and so the modal values calculated from the tunnel current are also heavily influenced thereby. For example, as in the exemplary embodiment described later, and as illustrated in A to C of FIG. 14, when modal values for GMP are calculated under conditions that are similar with the exception of the bias voltage, the respective modal values differ between bias voltages of 0.25V, 0.50V, and 0.75V.

The tunnel current measurement values accordingly have a distribution from the modal value of the identified nucleotide, and the modal values calculated from these measurement values also have a distribution from the identified nucleotide. The distribution from the modal values of the identified nucleotide may be expressed by the full width at half maximum of the function employed to calculate the modal values. Accordingly, the modal value calculated at the "process of calculating a modal value" described above is included in a range of the full width at half maximum centered on the modal value of the identified nucleotide.

The reference value for comparison with the modal value may accordingly be a modal value of the reference nucleotide, or may be a value in a range of x±y when x is modal value of the reference nucleotide and y is the half width half maximum of the function employed to calculate the modal value of the reference nucleotide. Moreover, since the modal value is influenced by various conditions as described above, the modal value of the reference nucleotide is preferably determined under similar conditions as the conditions under which the modal value of the nucleotide to which the present invention is being applied is determined.

When, in the result of the comparison between the modal value and the reference value, the modal value is included in the reference value, the nucleotide on which the present invention is being applied may be determined to be the reference nucleotide. Conversely, when the modal value is not included in the reference value, the nucleotide on which the present invention is being applied may be determined not to be the reference nucleotide. This determination enables identification of the nucleotide on which the present invention is being applied.

Figure 17:
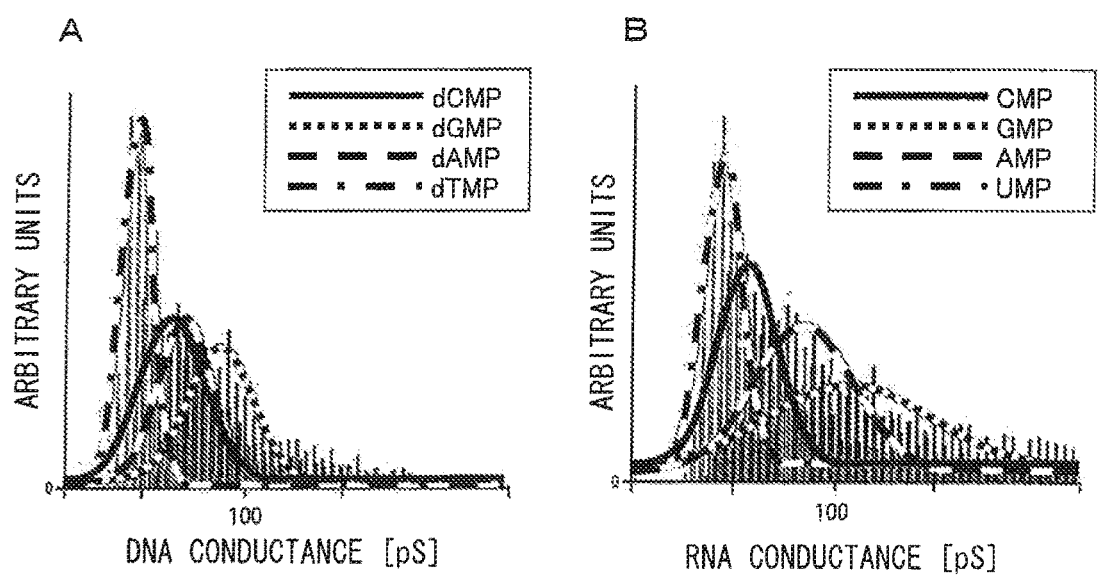
FIG. 17 is a diagram illustrating histograms of conductance of the nucleotides configuring DNA or RNA.

For example, as illustrated in FIG. 17, when the reference nucleotide is dGMP, x is 87 pS, and y is 22 pS. When the reference nucleotide is dAMP, x is 67 pS, and y is 17 pS. When the reference nucleotide is dCMP, x is 60 pS, and y is 22 pS. When the reference nucleotide is dTMP, x is 39 pS, and y is 11 pS. When the reference nucleotide is GMP, x is 123 pS, and y is 53 pS. When the reference nucleotide is AMP, x is 92 pS, and y is 32 pS. When the reference nucleotide is CMP, x is 64 pS, and y is 20 pS. When the reference nucleotide is UMP, x is 50 pS, and y is 13 pS.

When the modal value is included in a range of 87 pS±22 pS, the nucleotide may be determined to be dGMP. When the modal value is not included in the range of 87 pS±22 pS, the nucleotide may be determined not to be dGMP.

When the modal value is included in a range of 67 pS±17 pS, the nucleotide may be determined to be dAMP. When the modal value is not included in the range of 67 pS±17 pS, the nucleotide may be determined not to be dAMP.

When the modal value is included in a range of 60 pS±22 pS, the nucleotide may be determined to be dCMP. When the modal value is not included in the range of 60 pS±22 pS, the nucleotide may be determined not to be dCMP.

When the modal value is included in a range of 39 pS±11 pS, the nucleotide may be determined to be dTMP. When the modal value is not included in the range of 39 pS±11 pS, the nucleotide may be determined not to be dTMP.

When the modal value is included in a range of 123 pS±53 pS, the nucleotide may be determined to be GMP. When the modal value is not included in the range of 123 pS±53 pS, the nucleotide may be determined not to be GMP.

When the modal value is included in a range of 92 pS±32 pS, the nucleotide may be determined to be AMP. When the modal value is not included in the range of 92 pS±32 pS, the nucleotide may be determined not to be AMP.

When the modal value is included in a range of 64 pS±20 pS, the nucleotide may be determined to be CMP. When the modal value is not included in the range of 64 pS±20 pS, the nucleotide may be determined not to be CMP.

When the modal value is included in a range of 50 pS±13 pS, the nucleotide may be determined to be UMP. When the modal value is not included in the range of 50 pS±13 pS, the nucleotide may be determined not to be UMP.

Moreover, in the "process of comparing the calculated modal value against a reference value", the modal value may be compared against a single reference value, or the modal value may be compared against plural different reference values.

When the modal value is compared plural different reference values, the modal value may be compared against the reference values 1 by 1 such that "the modal value is compared against a first reference value, and when the modal value is not included in the first reference value, the modal value is compared against a second reference value". The modal value may also be compared against the plural different reference values in parallel, such that "the modal value is compared against the plural different reference values at the same time".

As described above, since the tunnel current is heavily influenced by various conditions, the modal values calculated from the tunnel current are also heavily influenced thereby. More accurate nucleotide identification can be realized by keeping such influences to a minimum. In order to keep such influences to a minimum, the modal value may be divided by a standard nucleotide modal value. Namely, in the method of the present invention may include a process of normalizing the modal value by dividing the modal value by a standard nucleotide modal value. Moreover, in the "process of comparing the calculated modal value against a reference value", the normalized modal value may be compared against a reference value that has been normalized by the standard nucleotide modal value (the normalized reference value may also be referred to as the reference value).

When, in the result of the comparison between the normalized modal value and the normalized reference value, the normalized modal value is included in the normalized reference value, the nucleotide on which the present invention is being applied may be determined to be the reference nucleotide. Conversely, when the normalized modal value is not included in the normalized reference value, the nucleotide on which the present invention is being applied may be determined not to be the reference nucleotide. This determination enables identification of the nucleotide on which the present invention is being applied.

The standard nucleotide is not particularly limited, and an appropriate nucleotide may be employed, however the standard nucleotide is preferably of the same type as the nucleotide on which the present invention is being applied. Namely, when the nucleotide on which the present invention is being applied is a deoxyribonucleotide, the standard nucleotide is preferably a deoxyribonucleotide (for example dGMP). Moreover, when the nucleotide on which the present invention is being applied is a ribonucleotide, the standard nucleotide is preferably a ribonucleotide (for example GMP).

For example, as illustrated in FIG. 17, when dGMP is employed as the standard nucleotide and dGMP is employed as the reference nucleotide, the normalized reference value is 1±0.25. When dGMP is employed as the standard nucleotide and dAMP is employed as the reference nucleotide, the normalized reference value is 0.77±0.20. When dGMP is employed as the standard nucleotide and dCMP is employed as the reference nucleotide, the normalized reference value is 0.69±0.25. When dGMP is employed as the standard nucleotide and dTMP is employed as the reference nucleotide, the normalized reference value is 0.45±0.12. When GMP is employed as the standard nucleotide and GMP is employed as the reference nucleotide, the normalized reference value is 1±0.44. When GMP is employed as the standard nucleotide and AMP is employed as the reference nucleotide, the normalized reference value is 0.75±0.27. When GMP is employed as the standard nucleotide and CMP is employed as the reference nucleotide, the normalized reference value is 0.52±0.16. When GMP is employed as the standard nucleotide and UMP is employed as the reference nucleotide, the normalized reference value is 0.41±0.10.

2. Nucleotide Identification Device

The present invention provides a nucleotide identification device. Since this is a device that performs the nucleotide identification method according to the present invention, the explanation for each process of the method described above may be referred to in the explanation of the respective members, with repeating portions being omitted.

Explanation follows regarding an exemplary embodiment the nucleotide identification device according to the present invention with reference to FIG. 1. FIG. 1 is a functional block diagram schematically illustrating an example of a nucleotide identification device (device 100) according to the present invention. The device 100 includes: an electrode pair 10 with an inter-electrode distance through which a polynucleotide is able to pass; an application means (voltage application section 20) that applies a voltage between the electrodes; a measurement means (current measuring section 30) that measures current values of a tunnel current arising between the electrodes; detecting means (detection section 40) that detects pulses in the measured tunnel current; a calculation means (calculation section 50) that calculates a modal value of the maximum current value of each of the pulses; and a comparison means (comparison section 60) that compares the calculated modal value against a reference value.

The relationship between each of the members is explained below.

The electrode pair 10 is electrically connected to the voltage application section 20 such that the voltage application section 20 is able to apply a voltage. The electrode pair 10 is moreover electrically connected to the current measuring section 30. When tunnel current arises between the electrodes due to application of a voltage by the voltage application section 20, the tunnel current is input into the current measuring section 30.

The current measuring section 30 is electrically connected to the detection section 40. When the current measuring section 30 has measured the current value of the tunnel current, the current measuring section 30 is capable of outputting data regarding this current value to the detection section 40. The detection section 40 is electrically connected to the calculation section 50. When the detection section 40 has detected each pulse, the detection section 40 is capable of outputting data regarding the pulse to the calculation section 50. The calculation section 50 calculates a modal value of the maximum current values based on the pulse data. The calculation section 50 is electrically connected to the comparison section 60. When the calculation section 50 has calculated the modal value, the calculation section 50 is capable of outputting data regarding the modal value to the comparison section 60.

The electrode pair 10 may employ electrodes configured from an appropriate metal, for example gold. A known power source device may be employed in the voltage application section 20. A known ammeter may be employed in the current measuring section 30. The detection section 40, the calculation section 50, and the comparison section 60 may for example preferably employ a computation device such as a known conventional computer.

The calculation section 50 may be provided with a first storage section (such as a known memory) stored with function data for statistical pulse analysis. The function data may include a single function, or may include plural different functions.

The comparison section 60 may be provided with a second storage section (such as a known memory) stored with reference value data for comparing against the modal value, and known nucleotide (reference nucleotide) data associated with the reference value(s). The reference value data may include a single reference value, or may include plural different reference values.

The device 100 may be further provided with an output section (not illustrated in the drawings) that outputs determination results from the comparison section 60. Providing the output section enables the user of the device 100 to easily check the determination results. There is no particular limitation to the output section, and a known display device is suggested as an example.

The device 100 may further include an input section (not illustrated in the drawings) for input of various conditions (for example functions, reference nucleotides) by the user.

Explanation follows regarding an example of operation of the device 100, with reference to FIG. 1.

Firstly, the device 100 holds the electrode pair 10 in a sample (for example a solution in which a nucleotide for analysis has been dissolved) (not illustrated in the drawings). Next, the device 100 applies a voltage to the electrode pair 10 with the voltage application section 20. This voltage application causes a tunnel current to be generated between the electrode pair 10 and input to the current measuring section 30. On input of the tunnel current to the current measuring section 30, the current measuring section 30 measures the current value of the tunnel current, and outputs data regarding this current value to the detection section 40. The detection section 40 detects a pulse in tunnel current based on the current value on input of this data into the detection section 40. For example, the detection section 40 establishes a point in time when the current value of the tunnel current has exceeded a base level, and establishes a point in time when the current value of the tunnel current has once again returned to the base level, and detects the signal of the tunnel current between these 2 points in time as a pulse.

The detection section 40 outputs data regarding each detected pulse to the calculation section 50. The calculation section 50 derives a maximum current value of each pulse based on the data regarding each pulse, and determines the modal value of the maximum current values. For example, the calculation section 50 derives the maximum current value of each pulse by deducting the base level from the current value of the highest peak of each detected pulse. The calculation section 50 moreover calculates modal value by performing statistical analysis on each derived maximum current value. The calculation section for example categorizes each pulse based on maximum current value, and calculates the modal value based on the number and maximum current values of the pulses belonging to each categorized group.

More specifically, the calculation section 50 generates a histogram expressing a relationship between the maximum current value of each pulse and the number of pulses corresponding to the maximum current values. Next, the generated histogram is fitted to a function stored in the first storage section, and a peak value of the fitted function is derived in order to calculate the modal value. In such cases, the calculation section 50 may select a function according to input by the user.

Lastly, the calculation section 50 outputs the calculated modal value data to the comparison section 60. The comparison section 60 identifies a nucleotide based on the modal value data. For example, the comparison section 60 compares the modal value data against the reference value stored in the second storage section. On verification by the comparison section 60 that the modal value is included in the reference value, the comparison section 60 determines that the nucleotide under analysis is the reference nucleotide associated with that reference value.

Conversely, when the comparison section 60 verifies that the modal value is not included in the reference value, the comparison section 60 determines that the nucleotide under analysis is not a reference nucleotide associated with that reference value.

Note that when the device 100 is provided with the output section (when the comparison section 60 is connected to the output section), the data regarding determination result of the comparison section 60 is input to the output section. The output section outputs the determination result, enabling the user of the device 100 to easily check the determination result.

When plural reference values are stored in the second storage section, the device 100 may perform the following operation in addition to the operation described above. The comparison section 60 verifies whether or not another reference value different to the reference value already compared against is stored in the second storage section. When the comparison section 60 verifies that another reference values is stored in the second storage section, the comparison section 60 compares the modal value against the other reference value, and verifies whether or not the modal value is included in the other reference value.

When the comparison section 60 verifies that the modal value is included in the other reference value, the comparison section 60 determines that the nucleotide under analysis is the reference nucleotide associated with that other reference value.

However, when the comparison section 60 verifies that another reference value is not stored in the second storage section (namely when the modal value is not included in any of the reference values stored in the second storage section), the comparison section 60 determines that the nucleotide under analysis is not any of the reference nucleotides associated with the reference values stored in the second storage section.

When plural different reference values are employed in this manner, the comparison section 60 may compare the modal value against the reference values 1 by 1 such that "the modal value is compared against a first reference value, and when the modal value is not included in the first reference value, the modal value is compared against a second reference value". The comparison section 60 may also compare the modal value against the plural different reference values in parallel, such that "the modal value is compared against the plural different reference values at the same time".

Configuration may be made such that the comparison section 60 normalizes the modal value by dividing the modal value input from the calculation section 50 by a standard nucleotide modal value. In such cases, the comparison section 60 compares the normalized modal value against a normalized reference value. The normalized reference value may be obtained by the comparison section 60 dividing the reference value stored in the second storage section by a standard nucleotide modal value, or the normalized reference value may be stored in advance in the second storage section. The comparison section 60 may select a reference nucleotide according to input by the user.

Figure 2:
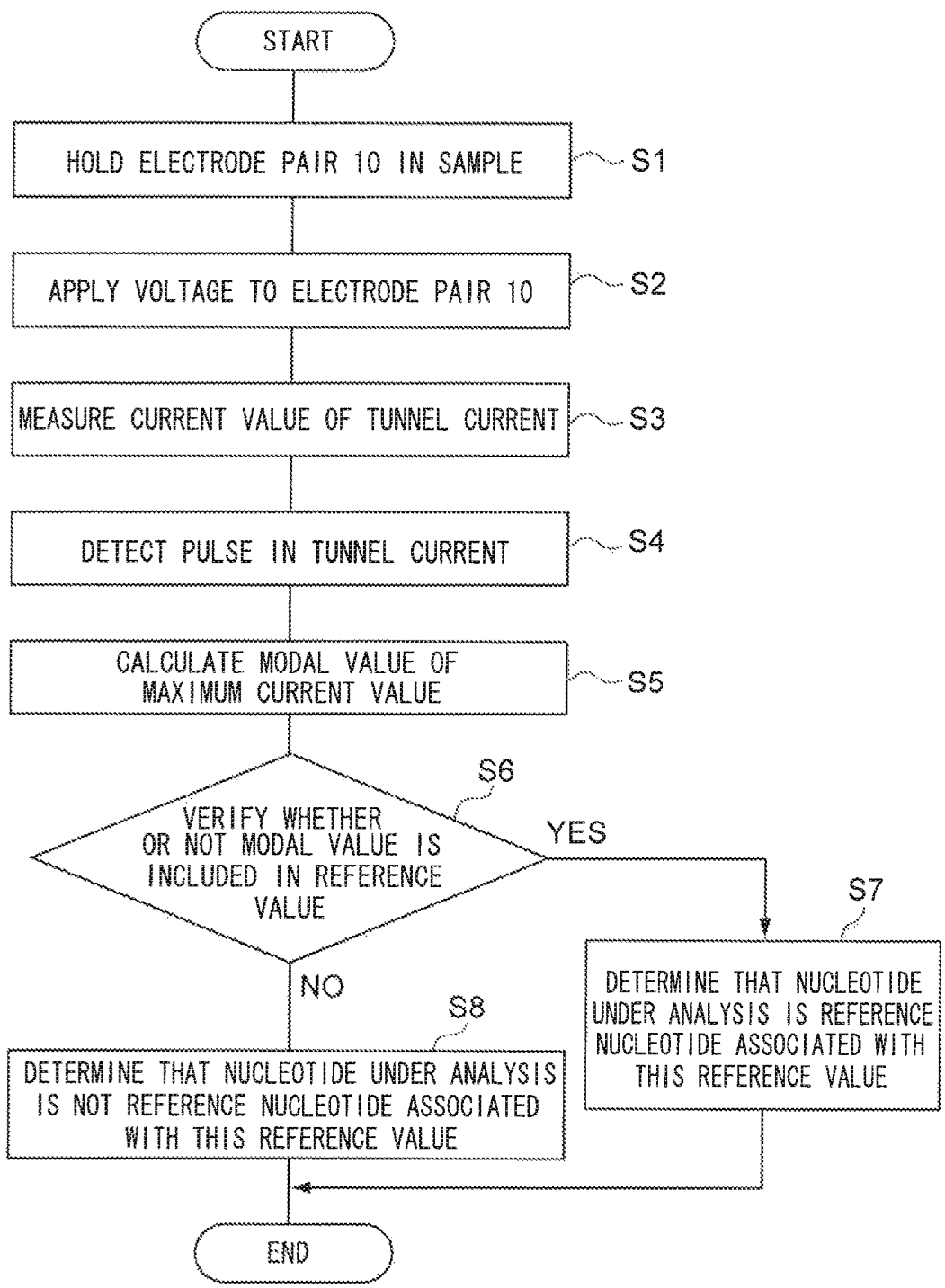
FIG. 2 is a flow chart illustrating an example of a flow of processing according to a device of the present invention.

Explanation follows regarding an example of flow of a nucleotide identification operation of the device 100 with reference to the flow chart illustrated in FIG. 2. In this flow, nucleotide identification is performed employing a single reference value.

At Step 1 (hereafter "step" is denoted by "S"), the device 100 holds the electrode pair 10 in a sample.

At S2, the voltage application section 20 applies a voltage to the electrode pair 10.

At S3, the current measuring section 30 measures the current value of the tunnel current generated in the processing of S2.

At S4, the detection section 40 detects a pulse of the tunnel current based on the current value measured in the processing of S3.

At S5, the calculation section 50 calculates the modal value of the maximum current value based on the data regarding each pulse detected in the processing of S4.

At S6, the comparison section 60 compares the modal value calculated in the processing of S5 against the reference value, and verifies whether or not the modal value is included in the reference value.

At S6, when verified by the comparison section 60 that the modal value is included in the reference value (when YES) processing transitions to S7. However, when verified at S6 by the comparison section 60 that the modal value is not included in the reference value (when NO), processing transitions to S8.

At S7, the comparison section 60 determines that the nucleotide under analysis is the reference nucleotide associated with that reference value. Processing is then ended.

At S8, the comparison section 60 determines that the nucleotide under analysis is not the reference nucleotide associated with that reference value. Processing is then ended.

Moreover, when the comparison section 60 normalizes the modal value, a step (S5') is present between S5 and S6, at which the comparison section 60 normalizes the modal value calculated in the processing of S5 with the standard nucleotide modal value. In such cases, at S6, the comparison section 60 compares the modal value normalized in the processing of S5' against the normalized reference value, and verifies whether or not the normalized modal value is included in the normalized reference value. The processing of S7 and S8 is then performed.

Note that when the device 100 is further provided with the output section, the flow described above may further include a step of an output section displaying the processing result of S7 after S7, and a step of the output section displaying the processing result of S8 after S8.

Figure 3:
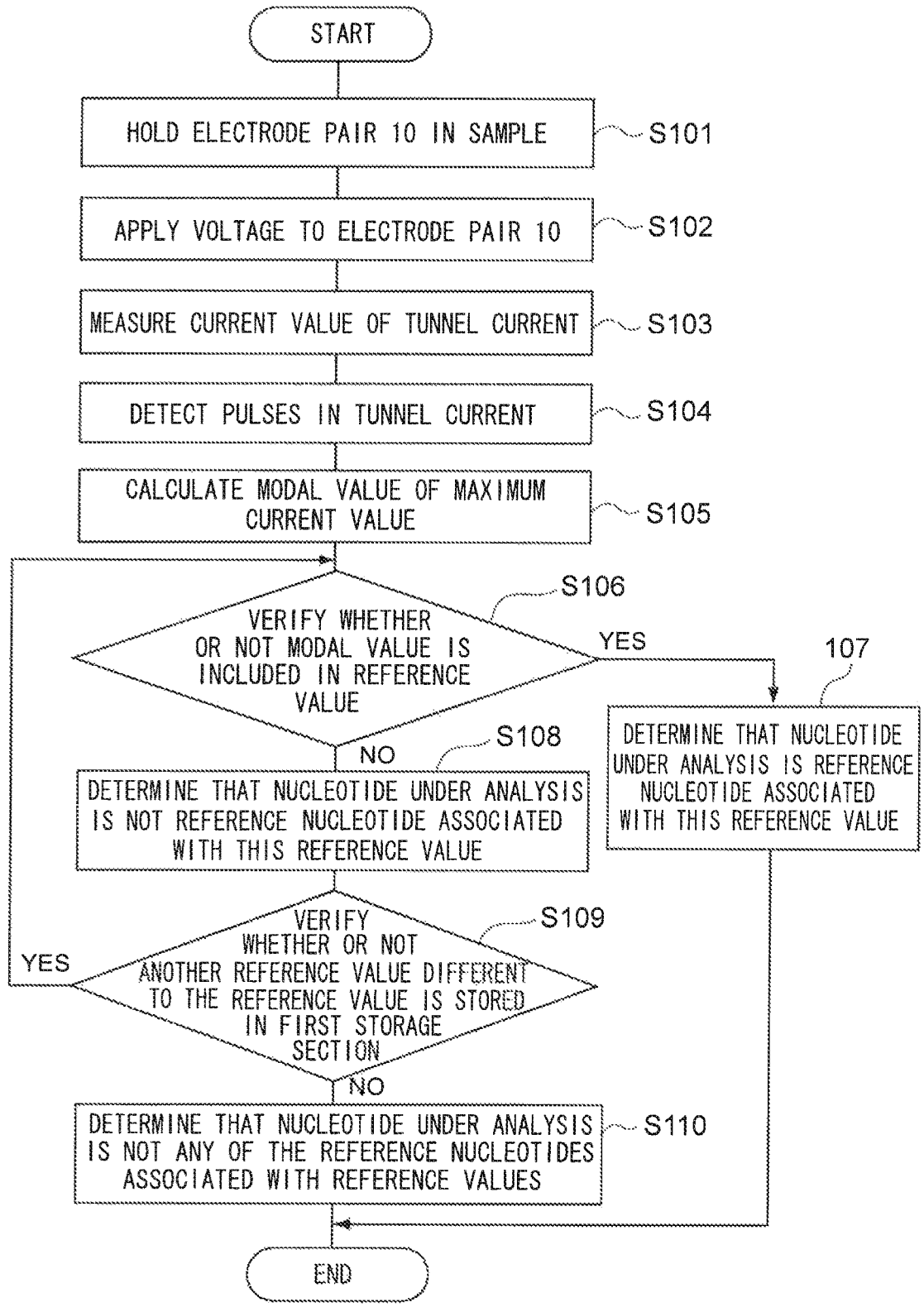
FIG. 3 is a flow chart illustrating an example of another example of a flow of processing according to a device of the present invention.

Explanation follows regarding another example of flow of nucleotide identification operation by the device 100, with reference to FIG. 3. In the following flow, nucleotide identification is performed employing plural different reference values.

At S101, the device 100 holds the electrode pair 10 in a sample.

At S102, the voltage application section 20 applies a voltage to the electrode pair 10.

At S103, the current measuring section 30 measures the current value of the tunnel current generated in the processing of S102.

At S104, the detection section 40 detects a pulse of the tunnel current based on the current value measured in the processing of S103.

At S105, the calculation section 50 calculates the modal value of the maximum current value based on the data regarding each pulse detected in the processing of S104.

At S106, the comparison section 60 compares the modal value calculated in the processing of S105 against the reference value, and verifies whether or not the modal value is included in the reference value.

At S106, when verified by the comparison section 60 that the modal value is included in the reference value (when YES) processing transitions to S107. However, when verified by the comparison section 60 at step S106 that the modal value is not included in the reference value (when NO), processing transitions to S108.

At S107, the comparison section 60 determines that the nucleotide under analysis is the reference nucleotide associated with that reference value. Processing is then ended.

At S108, the comparison section 60 determines that the nucleotide under analysis is not the reference nucleotide associated with that reference value, and processing transitions to S109.

At S109, the comparison section 60 verifies whether or not another reference value different to the above reference value is stored in the second storage section.

When at S109 the comparison section 60 verifies that there is another reference value stored in the second storage section (when YES), processing returns to S106. Here, similarly to in the processing in S106, the comparison section 60 compares the modal value against the other reference value and verifies whether or not the modal value is included in the other reference value. However when at S109 the comparison section 60 verifies that there are no other reference values stored in the second storage section (namely when the modal value is not included in any of the reference values stored in the second storage section), processing transitions to S110.

At S110, the comparison section 60 determines that the nucleotide under analysis is not any of the reference nucleotides associated with the reference values stored in the second storage section. Processing is then ended.

Note that when the device 100 is further provided with the output section, the flow described above may further include a step of displaying on the output section the processing result of S107 after S107, and a step of displaying on the output section the processing result of S110 after S110.

At S106, the modal value may be compared against a single reference value (namely, the modal value may be compared against the reference values 1 by 1), or the modal value may be compared against plural different reference values at the same time (in parallel).

Moreover, when the comparison section 60 normalizes the modal value, a step (S105') is present between S105 and S106, at which the comparison section 60 normalizes the modal value calculated in the processing of S105 with the standard nucleotide modal value. In such cases, at S106, the comparison section 60 compares the modal value normalized in the processing of S105' against the normalized reference value (or another normalized reference value), and verifies whether or not the normalized modal value is included in the normalized reference value (or the other normalized reference value). Moreover, at S109 the comparison section 60 verifies whether or not another normalized reference value different to the normalized reference value is stored in the second storage section.

When at S109 the comparison section 60 verifies that there is another normalized reference value stored in the second storage section (when YES), processing returns to S106. Here, similarly to in the processing at S106, the comparison section 60 compares the normalized modal value against the other normalized reference value and verifies whether or not the normalized modal value is included in the other normalized reference value. However when at S109 the comparison section 60 verifies that there are no other normalized reference values stored in the second storage section (namely when the normalized modal value is not included in any of the normalized reference values stored in the second storage section), processing transitions to S110.

3. Polynucleotide Nucleotide Sequence Determination Method

The present invention provides a method of determining the nucleotide sequence of a polynucleotide. The method of determining the nucleotide sequence of a polynucleotide includes: a process of passing the polynucleotide between electrodes; a process of measuring current values of a tunnel current arising between the electrodes as the polynucleotide passes through; a process of calculating a modal value of the measured current values; a process of normalizing the modal value of the current values by dividing the modal value of the current value by a modal value of a standard nucleotide; and a process of comparing the normalized modal value against a reference value.

As described above, since the tunnel current is heavily influenced by various conditions, it is difficult to identify the nucleotides configuring a polynucleotide by employing the modal value of the current value of the tunnel current calculated at the "process of calculating a modal value". However, due to dividing the modal value of the current value of the tunnel current by the modal value of the reference nucleotide at the "process of normalizing the modal value", these influences can be kept to a minimum. It is accordingly possible to identify the nucleotides of a polynucleotide at the "process of comparing the normalized modal value against a reference value".

Note that when only a single type of nucleotide is identified, the polynucleotide on which the present invention is being applied may be determined to be a polynucleotide configured by the same nucleotides. Namely, the nucleotide sequence of the polynucleotide to which the present invention is being applied may be determined to be configured by the identified single type of nucleotide.

However, when plural types of nucleotide are identified, the polynucleotide on which the present invention is being applied may be determined to be configured by different nucleotides. In such cases, in order to determine the nucleotide sequence of the polynucleotide on which the present invention is being applied, there is a need to establish the order of the nucleotides. To perform such establishment, the present invention further includes a process of detecting pulses of a tunnel current; a process of normalizing the current values of the pulses by dividing the current values by the modal value of the standard nucleotide; and a process of comparing the normalized current values against the reference value.

The present invention accordingly identifies the nucleotides configuring a polynucleotide, and realizes determination of the nucleotide sequence of the polynucleotide by establishing the order of the nucleotides configuring the polynucleotide as required.

When employed within the present specification, the term "polynucleotide" is used interchangeably with the terms "oligonucleotide" and "gene", and is used to refer to a nucleotide polymer. Note that when used in the present specification, the term "oligonucleotides" is used to mean 2 to several tens of individual, and more specifically, 2 to 50 individual nucleotides. "Polynucleotides" is used to mean several tens of individual or more, and more specifically, more than 50 individual nucleotides.

Polynucleotides may be configured by deoxyribonucleotides (DNA), or may be configured by ribonucleotides (RNA).

In the present specification, the term "nucleotide sequence" is used interchangeably with "base sequence", and refers to the sequence of deoxyribonucleotides or ribonucleotides.

Note that the method of determining the nucleotide sequence of a polynucleotide resembles the method of identifying a nucleotide described above, and explanation of the method of identifying a nucleotide may be cited as appropriate.

In order to implement the present exemplary embodiment of the present invention, there is a need to cause a tunnel current through a single molecule of a nucleotide configuring a polynucleotide as the polynucleotide passes through. The inter-electrode distance and the size of the electrodes (for example the length of the electrodes in the nucleotide passing direction, and the length of the electrode in a direction orthogonal to a plane formed by the direction between the electrodes and the nucleotide passing direction) are important in causing the tunnel current. Specifically, the inter-electrode distance and the size of the electrodes are preferably set at a level that is slightly shorter that the nucleotide molecular diameter, the same as the nucleotide molecular diameter, or greater than the nucleotide molecular diameter. The electrode pair described in the nucleotide identification method above may be employed for such an electrode pair.

In order to cause the tunnel current between the electrodes through a single molecule of a nucleotide configuring a polynucleotide, the polynucleotide being passed between the electrodes is preferably in linear single stranded form. When the polynucleotide is in double stranded form, a conventional known method such as applying heat to the polynucleotide may be employed to convert the polynucleotide into linear single stranded form. Note that sometimes, due to intramolecular interactions, nucleotides of a single stranded polynucleotide bond with each other and the single strand folds up with double strands forming at portions of the single strand. Non-linear single stranded polynucleotides may be made linear by a conventional known method such as applying heat to the single stranded polynucleotide.

Further explanation follows regarding each process.

The "process of passing a polynucleotide between electrodes" of the present invention is not particularly limited, and may be performed by similar operation to the "process of passing a nucleotide between electrodes a plurality of times" of the nucleotide identification method described above. Specifically, the electrode pair may be held in a solution in which the polynucleotide has been dissolved. By thus holding the electrode pair in the solution, the polynucleotide can be passed between the electrodes by employing the spontaneous movement of the polynucleotide in the solution. There is no particular limitation to the solution in which the polynucleotide is dissolved, however for example the ultrapure water described above may be employed. The concentration of the polynucleotide in the solution is not particularly limited, however is for example 5 µM.

Due to holding the electrode pair in the solution in which the polynucleotide has been dissolved and applying a voltage between the electrodes, a tunnel current caused by the nucleotides configuring the polynucleotide arises between the electrodes due to the polynucleotide passing through. Explanation follows regarding the mechanism by which the tunnel current arises.

As the polynucleotide enters between the electrodes, firstly a first nucleotide configuring the polynucleotide is trapped between the electrodes. A tunnel current caused by the first nucleotide arises between the electrodes when the first nucleotide is trapped between the electrodes.

Accompanying the movement of the polynucleotide between the electrodes, the first nucleotide moves between the electrodes and a second nucleotide enters between the electrodes. As the nucleotide that is trapped between the electrodes changes from the first nucleotide to the second nucleotide, a portion of the first nucleotide and a portion of the second nucleotide are trapped between the electrodes. Here, tunnel current arises between the electrodes caused by portions of both the first nucleotide and the second nucleotide, or either one of the first nucleotide and the second nucleotide.

Next, the first nucleotide has completely passed between the electrodes, and the entire second nucleotide is trapped between the electrodes. When the entire second nucleotide is trapped between the electrodes, tunnel current arises between the electrodes caused by the second nucleotide.

Finally, when the polynucleotide has passed between the electrodes (when the last nucleotide configuring the polynucleotide moves away from between the electrodes), the tunnel current arising between the electrodes disappears.

Accordingly, when the polynucleotide enters and moves between the electrodes, the nucleotides configuring the polynucleotide are trapped between the electrodes in order, and tunnel current caused by these nucleotides arises between the electrodes. When the polynucleotide moves away from between the electrodes, the tunnel current disappears. Namely, tunnel current pulses caused by the polynucleotide arise when the polynucleotide passes through between the electrodes.

In the present specification, similarly to the "tunnel current pulse caused by the nucleotide" described above, the "tunnel current pulse caused by the polynucleotide" refers to a tunnel current signal from the tunnel current rising above a base level until the tunnel current once again returns to the base level during measurement of the tunnel current for the specific duration. The increase in the tunnel current indicates that the first nucleotide configuring the polynucleotide is trapped between the electrodes, and the return of the tunnel current to the base level indicates that the trapped last nucleotide has moved away from between the electrodes.

"Base level" refers to an average noise value. "Noise" refers to a tunnel current signal observed when a nucleotide is not trapped between the electrodes. For example, noise can be obtained by measuring the current value of tunnel current arising when a voltage is applied between the electrodes that are being held in a solution in which no polynucleotide has been dissolved.

In the "a process of measuring current values of a tunnel current arising between the electrodes as the polynucleotide passes through" of the present invention, a voltage may be applied between the electrodes that are being held in the solution in which the polynucleotide has been dissolved and the current value of the tunnel current arising between the electrodes may be measured for the specific duration. Reference may be made to the above explanation regarding the nucleotide identification method for the method of applying voltage between the electrodes and the method of measuring the current value of the tunnel current arising between the electrodes.

In the "process of calculating a modal value of the measured current values" of the present invention, the modal value may be calculated by performing statistical analysis on the measured current value.

For example, the current values may be categorized based on value, and the modal value may be calculated based on the number and current values belonging to each categorized group. "Categorizing current values based on value" may for example involve categorizing the same, or substantially the same, current values into the same group, or may involve categorizing current values belonging to a uniform range into the same group. Note that "substantially the same current values" refers to current values differing by several % from a particular current value. For example, "substantially the same current values" refers to current values of between 90% and 110% of a particular current value.

More specifically, the modal value may be calculated as follows. Firstly, a histogram is generated that expresses a relationship between the number and current values belonging to each categorized group. The generated histogram is fitted to a specific function.

The modal value may then be calculated by deriving a peak value of the fitted function. The fitted function may be a Gaussian function or a Poisson function, and is preferably a Gaussian function.

The histogram may be generated so as to include noise current values, or may be generated so as not to include noise current values. When the histogram is generated including noise current values, generally plural peaks are observed, as illustrated on the left hand side in A to C of FIG. 18. The smallest value peak corresponds to the modal value of the noise current values, and peaks with greater values than this peak correspond to the modal value of the current values caused by the nucleotides configuring the polynucleotide. Accordingly, when plural peaks are observed, the modal value corresponding to the peaks is calculated by respectively deriving plural peak values.

In order to derive plural peak values, the generated histogram is fitted to a Gaussian function with its peak set at the center.

When the modal value of the noise current values is calculated, the modal value of the noise current values is preferably subtracted from the modal value of the current values caused by the nucleotides configuring the polynucleotide.

Note that when 2 peaks appear in a histogram generated including noise current values, one of the peaks corresponds to the modal value of the noise current values, and the other of the peaks corresponds to the modal value of the current values caused by the nucleotides configuring the polynucleotide. Namely, in such cases, the nucleotides configuring the polynucleotide can be determined to be configured by a single type of nucleotide. When 3 or more peaks appear in a histogram generated including noise current values, the nucleotides configuring the polynucleotide can be determined to be configured by plural types of nucleotide.

A histogram in which noise current values are not included is generated as follows. Firstly, a threshold value indicating noise is set. The threshold value is for example a maximum current value of tunnel current measured employing a solution in which no polynucleotide is dissolved. Next, the threshold value may be subtracted from the measured current value of the tunnel current. The histogram is generated employing the values obtained as a result. When 1 peak appears in a histogram that does not include noise current values, the nucleotides configuring the polynucleotide may be determined to be configured by a single type of nucleotide. When 2 or more peaks appear in a histogram that does not include noise current values, the nucleotides configuring the polynucleotide may be determined to be configured by plural types of nucleotide.

Determination can accordingly be made as to whether the nucleotides configuring a polynucleotide are configured by a single type of nucleotide, or configured by plural types of nucleotides, based on the number of peaks (the number of calculated modal values) in the histogram.

In the "process of normalizing the modal value of the current values by dividing the modal value of the current value by a modal value of a standard nucleotide" of the present invention, the modal value of the current values may be normalized by the standard nucleotide, however the point in time at which normalization is performed is not particularly limited. Namely, the current values of the pulses may be normalized at the "process of normalizing" after calculating the modal value at the "process of calculating", or the current values may be normalized at the "process of normalizing" after measuring the current value of the tunnel current at the "process of measuring current values of a tunnel current arising between the electrodes as the polynucleotide passes through", and the modal value of the normalized current values may be calculated at the "process of calculating".

The standard nucleotide is not particularly limited, and an appropriate nucleotide may be employed. When the polynucleotide is DNA, the standard nucleotide is preferably a deoxyribonucleotide (for example dGMP), and when the polynucleotide is RNA, the standard nucleotide is preferably a ribonucleotide (for example GMP).

The modal value of the standard nucleotide may be calculated by a similar method to the method used to calculate the modal value explained in the nucleotide identification method. Namely, the modal value of the standard nucleotide is obtained by passing the standard nucleotide between the electrodes plural times, detecting pulses of the tunnel current arising between the electrodes as the standard nucleotide passes through, and calculating a modal value of the maximum current value of each pulse.

Moreover, the modal value of the standard nucleotide employed is preferably obtained under similar conditions to the conditions employed for the polynucleotide under analysis (for example, electrode conditions (inter-electrode distance, electrode shape), solution concentration conditions). Note that "the same solution concentration conditions for the polynucleotide and the standard nucleotide" refers to the concentration of the polynucleotide in the solution and the concentration of the standard nucleotide in the solution being the same.

In the "a process of comparing the normalized modal value against a reference value" of the present invention, the modal value that has been normalized as described above may be compared against the reference value. The reference value employed in comparison is for example the reference value explained in the nucleotide identification method above (a reference value normalized with the standard nucleotide).

When, in the result of the comparison between the normalized modal value and the reference value, the normalized modal value is included in the reference value, the nucleotide with this modal value may be determined to be the reference nucleotide. Conversely, when the normalized modal value is not included in the reference value, the nucleotide with this modal value may be determined not to be the reference nucleotide. This determination accordingly enables identification of the nucleotides configuring the polynucleotide.

When only a single type of nucleotide is identified, the nucleotide sequence of the polynucleotide on which the present invention is being applied may be determined to be configured by the single type of nucleotide that has been identified.

However, when plural types of nucleotide are identified, the nucleotide sequence of the polynucleotide on which the present invention is being applied may be determined to be configured by plural types of nucleotide. In such cases, in order to determine the order of the plural types of nucleotide, and to determine the nucleotide sequence, a process of detecting pulses of a tunnel current, a process of detecting pulses of a tunnel current, a process of normalizing the current values of the pulses by dividing the current values by the modal value of the standard nucleotide and a process of comparing the normalized current values against the reference value are further performed.

The "process of detecting pulses of a tunnel current" of the present invention includes serially determining whether or not the current value of the tunnel current measured at the "process of measuring current values of a tunnel current arising between the electrodes as the polynucleotide passes through" exceeds the base level. When a point in time at which the tunnel current exceeds the base level is established, and when a point in time at which the tunnel current once again returns to the base level is established based on this determination, the signal between these 2 points in time can be detected as a tunnel current pulse. Employing a graph (for example a curve graph) expressing a relationship between the measured current value of the tunnel current caused by the polynucleotide and the tunnel current measurement duration enables easy performance of such determination by visual inspection.

Figure 18:
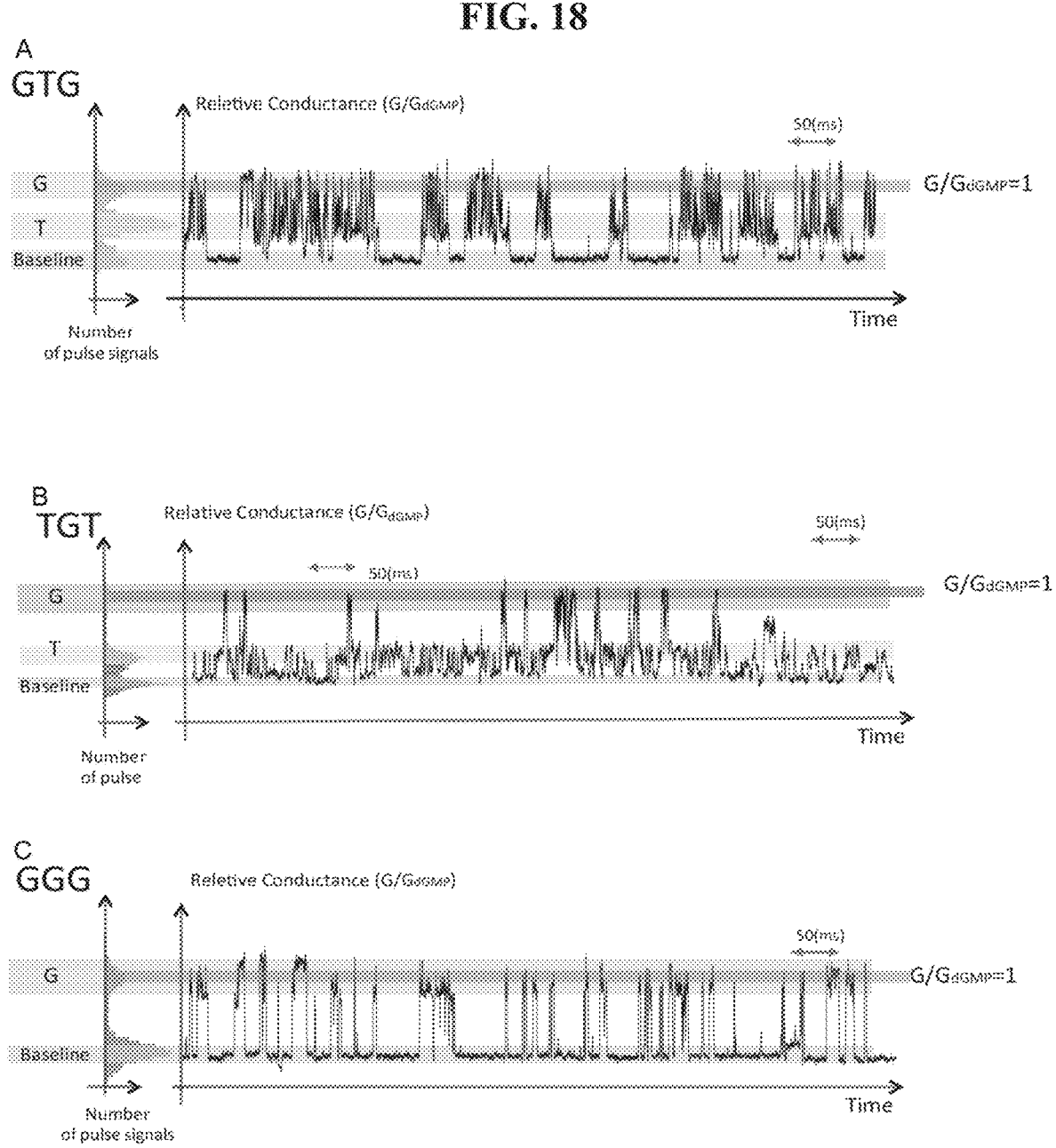
FIG. 18 is a diagram illustrating measurement results of tunnel current employing DNA.
Figure 19:
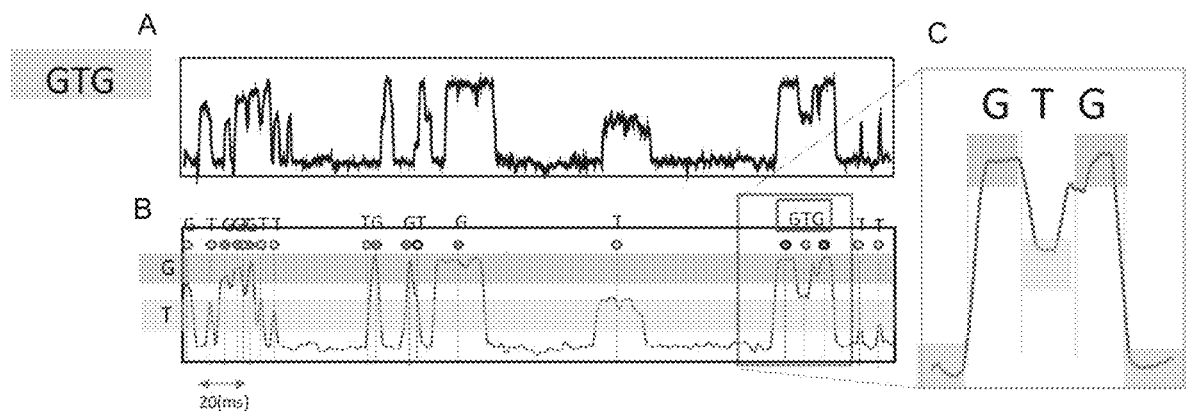
FIG. 19 is a diagram illustrating an enlarged portion of FIG. 18.

However as illustrated in FIG. 18 and FIG. 19, in actual tunnel current measurement, false pulses that do not correspond to tunnel current pulses caused by the polynucleotide are also measured. There is accordingly a need to establish which of the pulses detected by the above method are tunnel current pulses caused by the polynucleotide. Establishing the pulses can be performed based on the duration for which the polynucleotide remains between the electrodes.

The duration for which the polynucleotide remains between the electrodes can be calculated from the duration for which a single nucleotide molecule remains between the electrodes. The duration for which a single nucleotide molecule remains between the electrodes is the nucleotide pulse continuation duration, as explained in the nucleotide identification method. The nucleotide pulse continuation durations ("td" in B of FIG. 12, described later) are not necessarily uniform. However, the inventors of the present invention have discovered that a specific value appears for the nucleotide pulse continuation duration by performing statistical analysis on nucleotide pulse continuation durations. Specifically, producing a histogram of nucleotide pulse continuation durations and fitting this histogram to a function enables calculation of a modal value of nucleotide pulse continuation duration.

Note that since the polynucleotide passes between the electrodes by spontaneous movement, it may be assumed that the speed with which the polynucleotide passes between the electrodes is uniform. Similar conditions (for example the inter-electrode distance) are employed for calculating the modal value to the conditions employed in determining the nucleotide sequence of the polynucleotide, and by applying these assumptions, the duration for which a polynucleotide configured by n nucleotides remains between the electrodes (the duration of a tunnel current pulse caused by the polynucleotide) will be n times the modal value of the nucleotide pulse continuation duration.

Note that the nucleotide employed in calculating the duration for which the polynucleotide remains between the electrodes is preferably of the same type as the nucleotide configuring the polynucleotide under analysis. For example, when the polynucleotide is DNA, the nucleotide employed is preferably a deoxyribonucleotide, and when the polynucleotide is RNA, the nucleotide employed is preferably a ribonucleotide.

In other words, the continuation duration of a tunnel current pulse caused by the polynucleotide corresponds to the number of nucleotides configuring the polynucleotide. When the number of nucleotides configuring the polynucleotide is n, the width of the pulse can be divided into n equal parts. Moreover, each division of the divided pulse respectively corresponds to each of the nucleotides configuring the polynucleotide.

When the polynucleotide is configured from plural types of nucleotide, there is at least 1 pair present in which the adjacent nucleotides are different to each other. Since the measured current value of the tunnel current also differs when the nucleotides are different to each other, the current values exhibited for the corresponding adjacent divisions also differ when adjacent nucleotides are different to each other. For example, as illustrated at C in FIG. 19, when the nucleotide sequence of a polynucleotide is configured by GTG, the current value exhibited for the G first division becomes lower at the T second division then returns to the original current value for the G third division. As illustrated at C in FIG. 20, when the nucleotide sequence of the polynucleotide is configured by TGT, the current value exhibited for the T first division increases for the G second division, then returns to the original current value for the third T division.

The tunnel current pulse caused by a polynucleotide configured from plural types of nucleotide accordingly exhibits a step shaped signal.

The detected pulse can accordingly be established to be a tunnel current pulse caused by the polynucleotide under analysis by employing 2 conditions of (1) continuing for n times or more the modal value of the nucleotide pulse continuation duration, and (2) a step shaped signal is exhibited.

At the "process of normalizing the current values of the pulses by dividing the current values by the modal value of the standard nucleotide" of the present invention, the current values of the pulses may be normalized by the modal value of the standard nucleotide, however the point in time at which normalization is performed is not particularly limited. Namely, the current values of the pulses may be normalized at the "process of normalizing" after detecting the pulse at the "process of detecting pulses", or the current values may be normalized at the "process of normalizing" after measuring the current value of the tunnel current at the "process of measuring current values of a tunnel current arising between the electrodes as the polynucleotide passes through", and the pulse may be detected from the normalized current values at the "process of detecting pulses".

The standard nucleotide is not particularly limited, and is the standard nucleotide employed at the "process of normalizing the modal value of the current values by dividing the modal value of the current value by a modal value of a standard nucleotide" described above.

At the "process of comparing the normalized modal value against a reference value" of the present invention, the normalized current values may be compared against the reference value as described above. The reference value employed in the comparison is for example the reference value employed at the "process of comparing the normalized current values against the reference value" described above.

As described above, each division of the tunnel current pulse caused by the polynucleotide that is divided into number of nucleotides configuring the polynucleotide respectively corresponds to each nucleotide configuring the polynucleotide. Note that since a tunnel current pulse caused by a polynucleotide configured from plural types of nucleotide exhibits a step shaped signal, as illustrated at C in FIG. 19 and at D in FIG. 20, the normalized current values at a single segment of the pulse may sometimes be included in plural reference values. However, when the normalized current values are included in plural reference values, the reference value of the nucleotide corresponding to this segment may be taken as the reference value in which the normalized current value is included for the longest duration.

Accordingly, at the "process of comparing the normalized current values against the reference value", the normalized current value of the pulse at a single segment is preferably established as the reference value in which it is included for the longest duration. The nucleotide at this segment can accordingly be identified.

Specifically, the duration for which the normalized current value of a pulse of a single segment is included in each reference value is measured. The longest duration is determined by comparing the respective measured durations against each other. Establishing the reference value for the determined duration enables the nucleotide of this segment to be identified as the nucleotide corresponding to this reference value.

The order of the nucleotides of the polynucleotide can accordingly be determined by identifying the nucleotides for each segment.

At the "process of comparing the normalized current values against the reference value", a threshold value may be set for "a duration for which the normalized current value of the pulse is included in the reference value". Setting this threshold value enables the current value to be regarded as not being included in a reference value if not included in the reference value for the threshold value or longer. The threshold value may be set as appropriate by a person skilled in the art. By employing such a threshold value, sometimes it is not possible to establish a reference value in which the normalized current value of a single segment of the pulse is included. In such cases, the nucleotide for that segment can be determined as unknown.

4. Polynucleotide Nucleotide Sequence Determination Device

First Exemplary Embodiment

The present invention provides a device that determines the nucleotide sequence of a polynucleotide. Since the device performs the method of determining the nucleotide sequence of a polynucleotide of the present invention, the explanation for each process of the method described above may be referred to in the explanation of the respective members.

Figure 4:
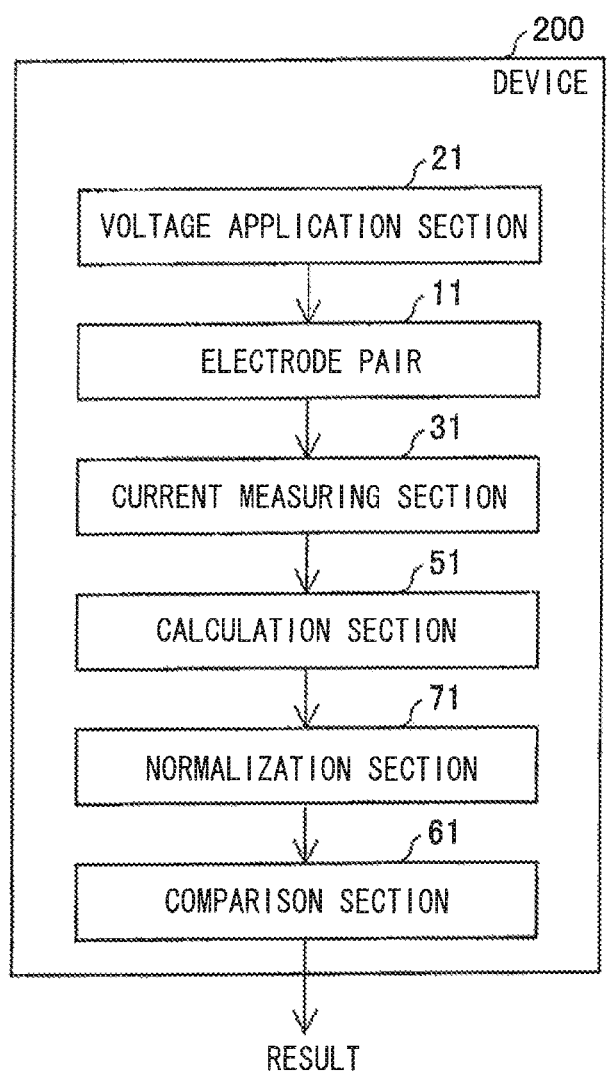
FIG. 4 is a function block diagram schematically illustrating an example of another device of the present invention.

Explanation follows regarding the polynucleotide nucleotide sequence determination device of the present invention, with reference to FIG. 4. FIG. 4 is a functional block diagram schematically illustrating an example of the device (device 200) of the present exemplary embodiment. The device 200 includes: an electrode pair 11 with an inter-electrode distance through which a polynucleotide is able to pass; an application means (voltage application section 21) that applies a voltage between the electrodes; a measurement means (current measuring section 31) that measures current values of a tunnel current arising between the electrodes; a calculation means (calculation section 51) that calculates a modal value of the maximum current value of each of the pulses; a normalizing means (normalization section 71) that normalizes the modal value of the current values by dividing the modal value of the current values by a modal value of a standard nucleotide; and a comparison means (comparison section 61) that compares the normalized modal value against a reference value.

The relationship between each of the members is explained below.

The electrode pair 11 is electrically connected to the voltage application section 21 such that the voltage application section 21 is able to apply a voltage. The electrode pair 11 is moreover electrically connected to the current measuring section 31. When tunnel current arises between the electrodes due to application of a voltage by the voltage application section 21, the tunnel current is input into the current measuring section 31.

The current measuring section 31 is electrically connected to the calculation section 51. When the current measuring section 31 has measured the current value of the tunnel current, the current measuring section 31 is capable of outputting data regarding this current value to the calculation section 51. The calculation section 51 is electrically connected to the normalization section 71. When the calculation section 51 has calculated the modal value, the calculation section 51 is capable of outputting this data regarding this modal value to the normalization section 71. The normalization section 71 is electrically connected to the comparison section 61. When the normalization section 71 has normalized the modal value, the normalization section 71 is capable of outputting the normalized modal value to the comparison section 61.

The electrode pair 11 may employ the electrode pair 10 described above. The voltage application section 21 may employ the voltage application section 20 described above. The current measuring section 31 may employ the current measuring section 30 described above. The calculation section 51, the normalization section 71 and the comparison section 61 may for example appropriately employ a computing device such as a known conventional computer.

The calculation section 51 may be provided with a third storage section (for example a known memory) stored with function data for statistical current value analysis. The function data may include a single function, or may include plural different functions.

The normalization section 71 may be provided with a fourth storage section (for example a known memory) stored with standard nucleotide data for normalizing modal values. The standard nucleotide data may include a single standard nucleotide, or may include plural different standard nucleotides.

The comparison section 61 may be provided with a fifth storage section (such as a known memory) stored with reference value data for comparing against the modal value, and known nucleotide (reference nucleotide) data associated with the reference value(s). The reference value data may include a single reference value, or may include plural different reference values.

The device 200 may be further provided with an output section (not illustrated in the drawings) that outputs determination results from the comparison section 61. Providing the output section enables the user of the device 200 to easily check the determination results. There is no particular limitation to the output section, and a known display device is suggested as an example.

The device 200 may be further provided with an input section (not illustrated in the drawings) for input of various conditions (for example function, standard nucleotide, continuation duration of a pulse of a nucleotide, number of nucleotides configuring a polynucleotide subject to analysis) by a user.

Explanation follows regarding an example of operation of the device 200, with reference to FIG. 4.

Firstly, the device 200 holds the electrode pair 11 in a sample (for example a solution in which a polynucleotide for analysis has been dissolved) (not illustrated in the drawings). Next, the device 200 applies a voltage to the electrode pair 11 with the voltage application section 21. This voltage application causes a tunnel current to be generated between the electrode pair 11 and input to the current measuring section 31. On input of the tunnel current to the current measuring section 31, the current measuring section 31 measures the current value of the tunnel current, and outputs data regarding this current value to the calculation section 51. When the data regarding the current value has been input to the calculation section 51, the calculation section 51 calculates the modal value of the current value. The calculation section 51 for example calculates the modal value by performing statistical analysis on the current values. The calculation section 51 for example categorizes the current values based on their values, and calculates the modal value based on the number and current values belonging to each categorized group.

More specifically, the calculation section 51 generates a histogram expressing a relationship between number belonging to, and current values, for each categorized group. Next, the generated histogram is fitted to a function stored in the third storage section, and a peak value of the fitted function is derived in order to calculate the modal value. In such cases, the calculation section 51 may select a function according to input by the user.

The calculation section 51 then outputs data regarding the calculated modal value to the normalization section 71. The normalization section 71 normalizes modal value of the current values by dividing the input modal value by the modal value of a standard nucleotide stored in the fourth storage section. Here, the normalization section 71 may select the standard nucleotide modal value according to input by the user. Next, the normalization section 71 outputs data regarding the normalized modal value to the comparison section 61.

The comparison section 61 identifies the nucleotides configuring the polynucleotide based on the normalized modal value data. For example, the comparison section 61 compares the normalized modal value against the reference value stored in the fifth storage section. When the comparison section 61 verifies that the normalized modal value is included in the reference value, the comparison section 61 determines that the nucleotide of the normalized modal value is the reference nucleotide associated with that reference value. Conversely, when the comparison section 61 verifies that the normalized modal value is not included in the reference value, the comparison section 61 determines that the nucleotide of the normalized modal value is not the reference nucleotide associated with this reference value.

When, as a result of this determination, the comparison section 61 only identifies a single type of nucleotide, the comparison section 61 determines that the polynucleotide to which the present invention is being applied is configured by the same nucleotide. The comparison section 61 moreover determines that the nucleotide sequence of the polynucleotide is configured by the identified single type of nucleotide.

However, when the comparison section 61 has identified plural types of nucleotide, the comparison section 61 determines that the polynucleotide to which the present invention is being applied is configured by different types of nucleotide. In such cases, the comparison section 61 determines that it is not possible to determine the nucleotide sequence of the polynucleotide.

Note that when the device 200 is provided with the output section (when the comparison section 61 is connected to the output section), the data regarding the determination of the comparison section 61 is input to the output section. The output section outputs the determination data, enabling the user of the device 200 to easily check the determination of the comparison section 61.

When plural reference values are stored in the fifth storage section, the device 200 may perform the following operation in addition to the operation described above. The comparison section 61 verifies whether or not another reference value different to the reference value that has already been compared against is stored in the fifth storage section. When the comparison section 61 verifies that another reference value is stored in the fifth storage section, the comparison section 61 compares the modal value against the other reference value, and verifies whether or not the modal value is included in the other reference value.

When the comparison section 61 verifies that the modal value is included in the other reference value, the comparison section 61 determines that the nucleotide under analysis is the reference nucleotide associated with the other reference value.

However when the comparison section 61 verifies that another reference value is not stored in the fifth storage section (namely when the modal value is not included in any of the reference values stored in the fifth storage section), the comparison section 61 determines that the nucleotide under analysis is not any of the reference nucleotides associated with the reference values stored in the fifth storage section.

When plural different reference values are employed in this manner, the comparison section 61 may compare the modal value against the reference values 1 by 1 such that "the modal value is compared against a first reference value, and when the modal value is not included in the first reference value, the modal value is compared against a second reference value". The comparison section 61 may also compare the modal value against the plural different reference values in parallel, such that "the modal value is compared against the plural different reference values at the same time".

Figure 5:
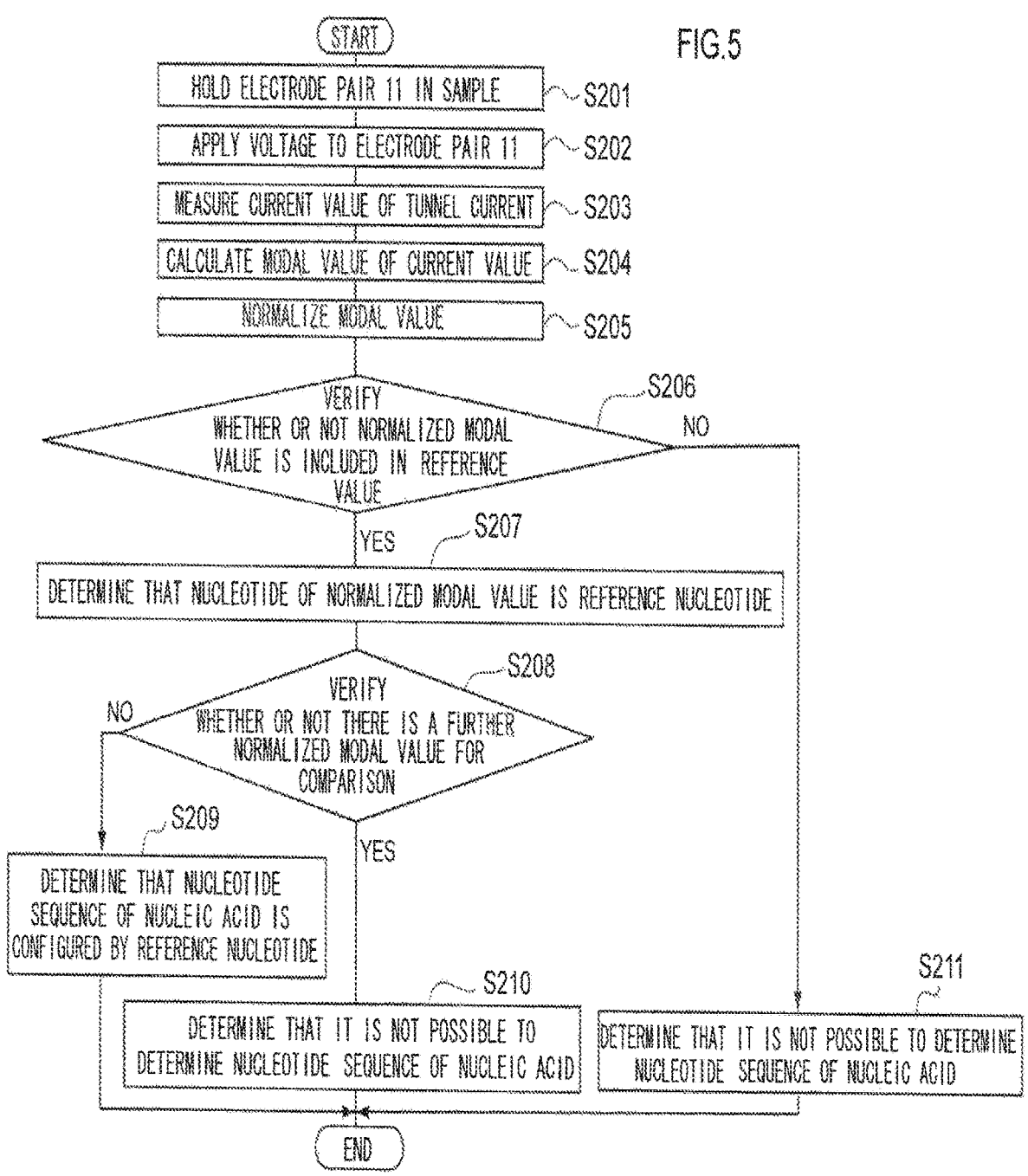
FIG. 5 is a flow chart illustrating an example of a flow of processing according to another device of the present invention.

Explanation follows regarding an example of flow of a polynucleotide nucleotide sequence determination operation of the device 200 with reference to the flow chart illustrated in FIG. 5. In this flow, polynucleotide nucleotide sequence determination is performed employing a single reference value.

At S201, the device 200 holds the electrode pair 11 in a sample.

At S202, the voltage application section 21 applies a voltage to the electrode pair 11.

At S203, the current measuring section 31 measures the current value of the tunnel current generated in the processing of S202.

At S204, the calculation section 51 calculates the modal value of the current value measured in the processing of S203.

At S205, the normalization section 71 normalizes the modal value calculated in the processing of S204.

At S206, the comparison section 61 compares the modal value normalized in the processing of S205 against the reference value, and verifies whether or not the normalized modal value is included in the reference value.

At S206, when verified by the comparison section 61 that the modal value is included in the reference value (when YES) processing transitions to S207. However, when verified by the comparison section 61 at S206 that the modal value is not included in the reference value (when NO), processing transitions to S211.

At S207, the comparison section 61 determines that the nucleotide of the normalized modal value is the reference nucleotide associated with this reference value.

At S208, the comparison section 61 verifies whether or not there is a further normalized modal value for comparison. When at S208 the comparison section 61 verifies that there are no further normalized modal values for comparison (when NO), processing transitions to S209. However, when at S208 the comparison section 61 verifies that there is a further normalized modal value for comparison (when YES), processing transitions to S210.

At S209, the comparison section 61 determines that the polynucleotide to which the present invention is being applied is configured by a single type of nucleotide, and determines that the nucleotide sequence of the polynucleotide is configured by the reference nucleotide identified in the processing of S207. Processing is then ended.

At S210, the comparison section 61 determines that the polynucleotide to which the present invention is being applied is configured by plural types of nucleotide, and determines that it is not possible to determine the nucleotide sequence of the polynucleotide. Processing is then ended.

At S211, the comparison section 61 determines that the polynucleotide to which the present invention is being applied is configured by an unknown nucleotide, and determines that it is not possible to determine the nucleotide sequence of the polynucleotide. Processing is then ended.

Note that when the device 200 is further provided with an output section, the flow described above may further include a step of the output section displaying the processing result of S209 after S209, a step of the output section displaying the processing result of S210 after S210, and a step of the output section displaying the processing result of S211 after S211.

Figure 6:
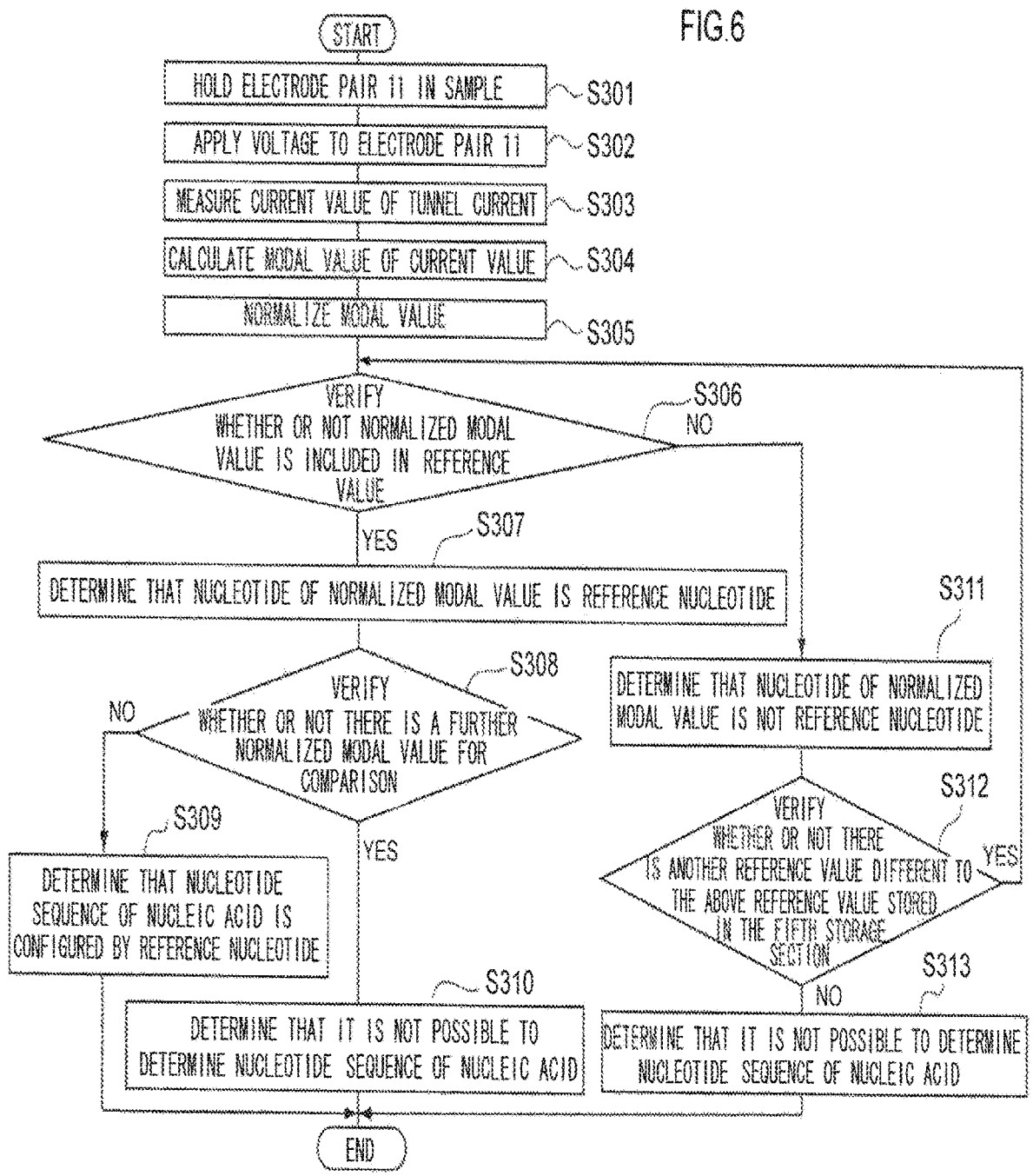
FIG. 6 is a flow chart illustrating another example of a flow of processing according to another device of the present invention.

Explanation follows regarding another example of flow of nucleotide identification operation by the device 200, with reference to the flow chart illustrated in FIG. 6. In the following flow, nucleotide identification is performed employing plural different reference values.

At S301, the device 200 holds the electrode pair 11 in a sample.

At S302, the voltage application section 21 applies a voltage to the electrode pair 11.

At S303, the current measuring section 31 measures the current value of the tunnel current generated in the processing of S302.

At S304, the calculation section 51 calculates the modal value of the current value measured in the processing of S303.

At S305, the normalization section 71 normalizes the modal value calculated in the processing of S304.

At S306, the comparison section 61 compares the modal value normalized in the processing of S305 against the reference value, and verifies whether or not the normalized modal value is included in the reference value.

At S306, when verified by the comparison section 61 that the modal value is included in the reference value (when YES) processing transitions to S307. However, when verified by the comparison section 61 at S306 that the modal value is not included in the reference value (when NO), processing transitions to S311.

At S307, the comparison section 61 determines that the nucleotide of the normalized modal value is the reference nucleotide associated with this reference value.

At S308, the comparison section 61 verifies whether or not further normalized modal values for comparison are present. When at S308 the comparison section 61 verifies that there are no further normalized modal values for comparison (when NO), processing transitions to S309. However, when at S308 the comparison section 61 verifies that there are further normalized modal values for comparison (when YES), processing transitions to S310.

At S309, the comparison section 61 determines that the polynucleotide to which the present invention is being applied is configured by a single type of nucleotide, and determines that the nucleotide sequence of the polynucleotide is configured by the reference nucleotide identified in the processing of S307. Processing is then ended.

At S310, the comparison section 61 determines that the polynucleotide to which the present invention is being applied is configured by plural types of nucleotide, and determines that it is not possible to determine the nucleotide sequence of the polynucleotide. Processing is then ended.

At S311, the comparison section 61 determines that the nucleotide of the normalized modal value is not the nucleotide associated with this reference value, and processing transitions to S312.

At S312, the comparison section 61 verifies whether or not there is another reference value different to the above reference value stored in the fifth storage section. When at S312 the comparison section 61 verifies that there is another reference value stored in the fifth storage section (when YES), processing returns to S306. Here, similarly to in the processing at S306, the comparison section 61 compares the modal value against the other reference value and verifies whether or not the modal value is included in the other reference value. However when at S312 the comparison section 61 verifies that there are no other reference values stored in the fifth storage section (namely when the modal value is not included in any of the reference values stored in the fifth storage section), processing transitions to S313.

At S313, the comparison section 61 determines that the nucleotide of the normalized modal value is not any of the reference nucleotides associated with the reference values stored in the fifth storage section, and determines that it is not possible to determine the nucleotide sequence of the polynucleotide. Processing is then ended.

Note that when the device 200 is further provided with an output section, the flow described above may further include a step of the output section displaying the processing result of S309 after S309, a step of the output section displaying the processing result of S310 after S310, and a step of the output section displaying the processing result of S313 after S313.

At S306, the modal value may be compared against a single reference value (namely, the modal value may be compared against the reference values 1 by 1), or the modal value may be compared against plural different reference values at the same time (in parallel).

Second Exemplary Embodiment

Figure 7:
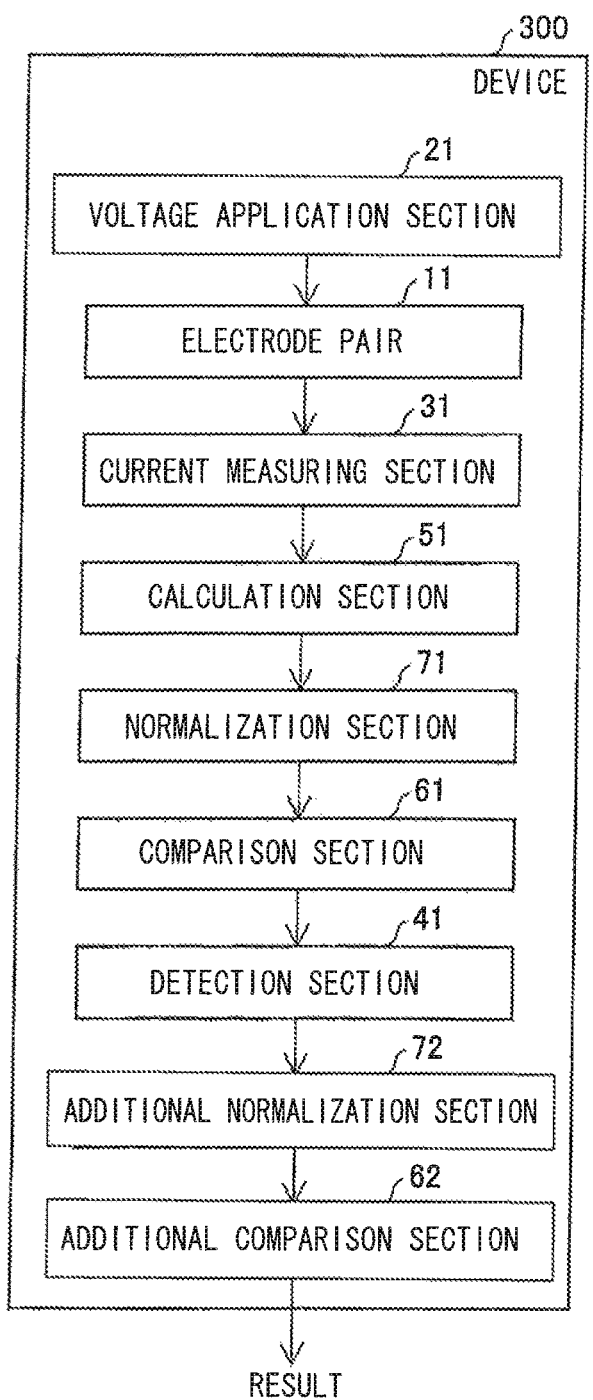
FIG. 7 is a function block diagram schematically illustrating an example of yet another device of the present invention.

Explanation follows regarding the polynucleotide nucleotide sequence determination device of the present invention, with reference to FIG. 7. FIG. 7 is a function block diagram schematically illustrating an example of the device (device 300) of the present exemplary embodiment. The device 300 is the device 200 of the first exemplary embodiment, further including: a detection means (detection section 41) that detects pulses of a tunnel current; a normalization means (additional normalization section 72) that normalizes the current values by dividing the current values of the pulses by the modal value of the standard nucleotide; and a comparison means (comparison section 62) that compares the normalized current values against the reference value. Explanation is given regarding the device 300 below, however explanation is omitted for portions repeated from the device 100.

In the device 300, the comparison section 61 is electrically connected to the detection section 41. Accordingly, when plural types of nucleotides are identified by the comparison section 61, the comparison section 61 instructs the detection section 41 to detect tunnel current pulses. The detection section 41 is electrically connected to the additional normalization section 72, and when the detection section 41 detects a pulse, data regarding the pulse is output to the additional normalization section 72. The additional normalization section 72 is electrically connected to the additional comparison section 62. When the additional normalization section 72 has normalized current values of the pulse, data regarding the normalized current values is output to the additional comparison section 62.

The detection section 41, the additional normalization section 72 and the additional comparison section 62 may for example preferably employ a computation device such as a conventional known computer. The detection section 41 may be provided with a sixth storage section (for example known memory) stored with data regarding nucleotide pulse continuation duration. The normalization section 71 may be combined with the additional normalization section 72, or the normalization section 71 and the additional normalization section 72 may be configured by separate devices. Moreover, the comparison section 61 may be combined with the additional comparison section 62, or the comparison section 61 and the additional comparison section 62 may be configured by separate devices.

Explanation follows regarding an example of the device 300 with reference to FIG. 7. Operation of the electrode pair 11 to the comparison section 61 is similar to that of the device 200 described above.

When the comparison section 61 only identifies a single type of nucleotide, the comparison section 61 determines that the polynucleotide to which the present invention is being applied is configured by the same nucleotide. The comparison section 61 moreover determines that the nucleotide sequence of the polynucleotide is configured by the identified single type of nucleotide.

However, when the comparison section 61 has identified plural types of nucleotide, the comparison section 61 determines that the polynucleotide to which the present invention is being applied is configured by different nucleotides. In such cases, the comparison section 61 instructs the detection section 41 to detect tunnel current pulses.

The detection section 41 receives instruction from the comparison section 61 and detects tunnel current pulses. For example, the detection section 41 instructs the current measuring section 31 to output data regarding current values of the measured tunnel current to the detection section 41. The current measuring section 31 outputs current value data to the detection section 41 based on instruction from the detection section 41. The detection section 41 detects pulses of the tunnel current from the input current value data. Specifically, the detection section 41 detects tunnel current pulses caused by the polynucleotide under analysis by utilizing 2 conditions of (1) the pulse of the nucleotide continuing for a duration n times or more the modal value of the nucleotide pulse continuation duration, and (2) a step shaped signal is exhibited. The detection section 41 moreover outputs data regarding the detected pulses to the additional normalization section 72.

The additional normalization section 72 normalizes the current values by dividing the input pulse current values by the modal value of the standard nucleotide. Next, the normalization section 71 outputs data regarding the normalized current values to the additional comparison section 62.

The additional comparison section 62 determines the order of the nucleotides configuring the polynucleotide based on the normalized current value data. For example, the additional comparison section 62 divides the pulses into the number of nucleotides configuring the polynucleotide. Next, the reference value in which the normalized pulse current values of the divided segments are included for the longest duration is established. The additional comparison section 62 identifies that the nucleotide of that segment is the reference nucleotide associated with the established reference value.

Moreover, when a reference value in which the normalized pulse current values of one section are contained cannot be established based on the threshold value of the duration normalized pulse current values are included in the reference value, the additional comparison section 62 determines that the nucleotide of this segment is unknown.

Note that the number of nucleotides configuring the polynucleotide and the threshold value may be configured based on input by the user through the input section.

Figure 8A:
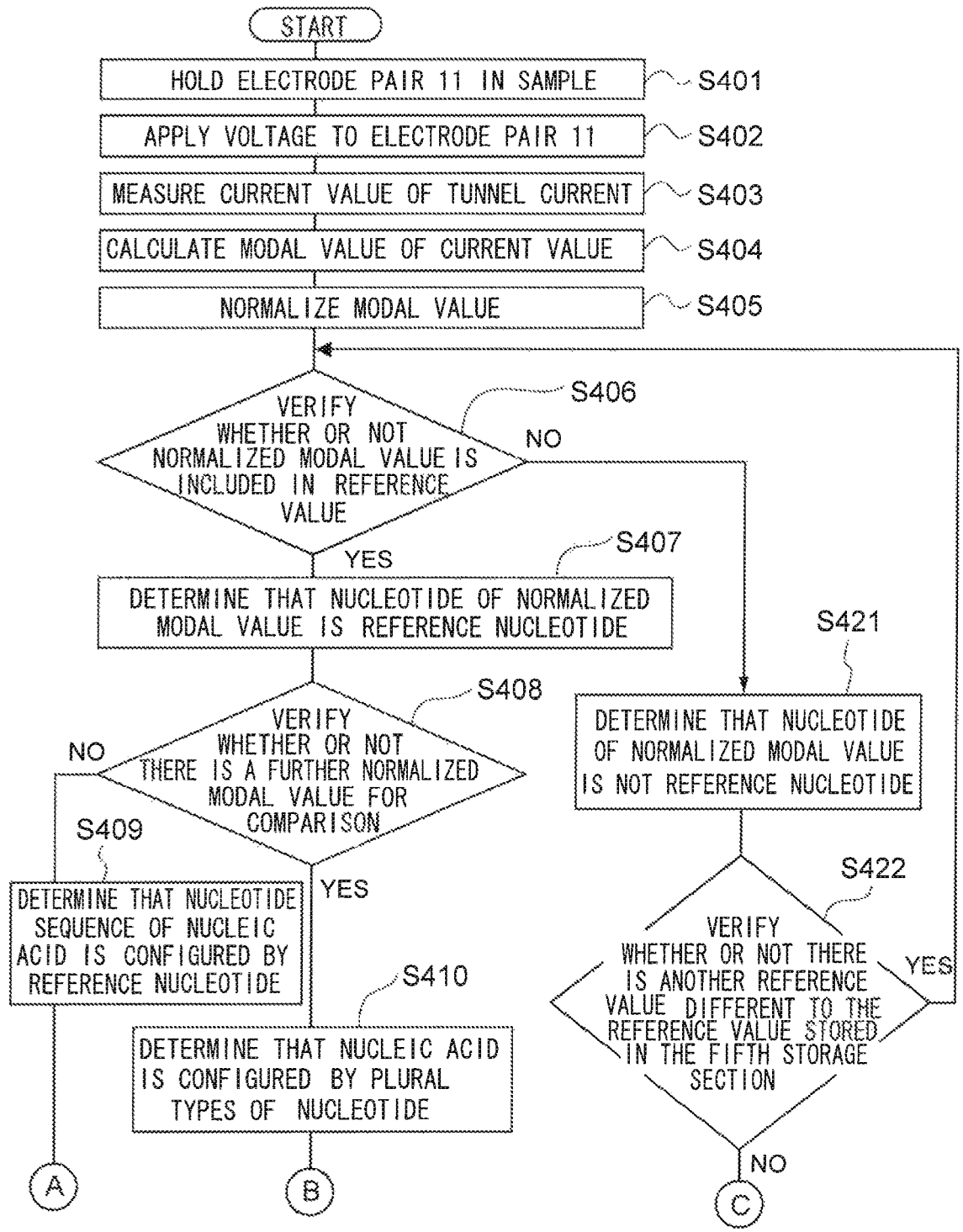
FIG. 8A is a flow chart illustrating an example of a flow of processing according to yet another device of the present invention.
Figure 8B:
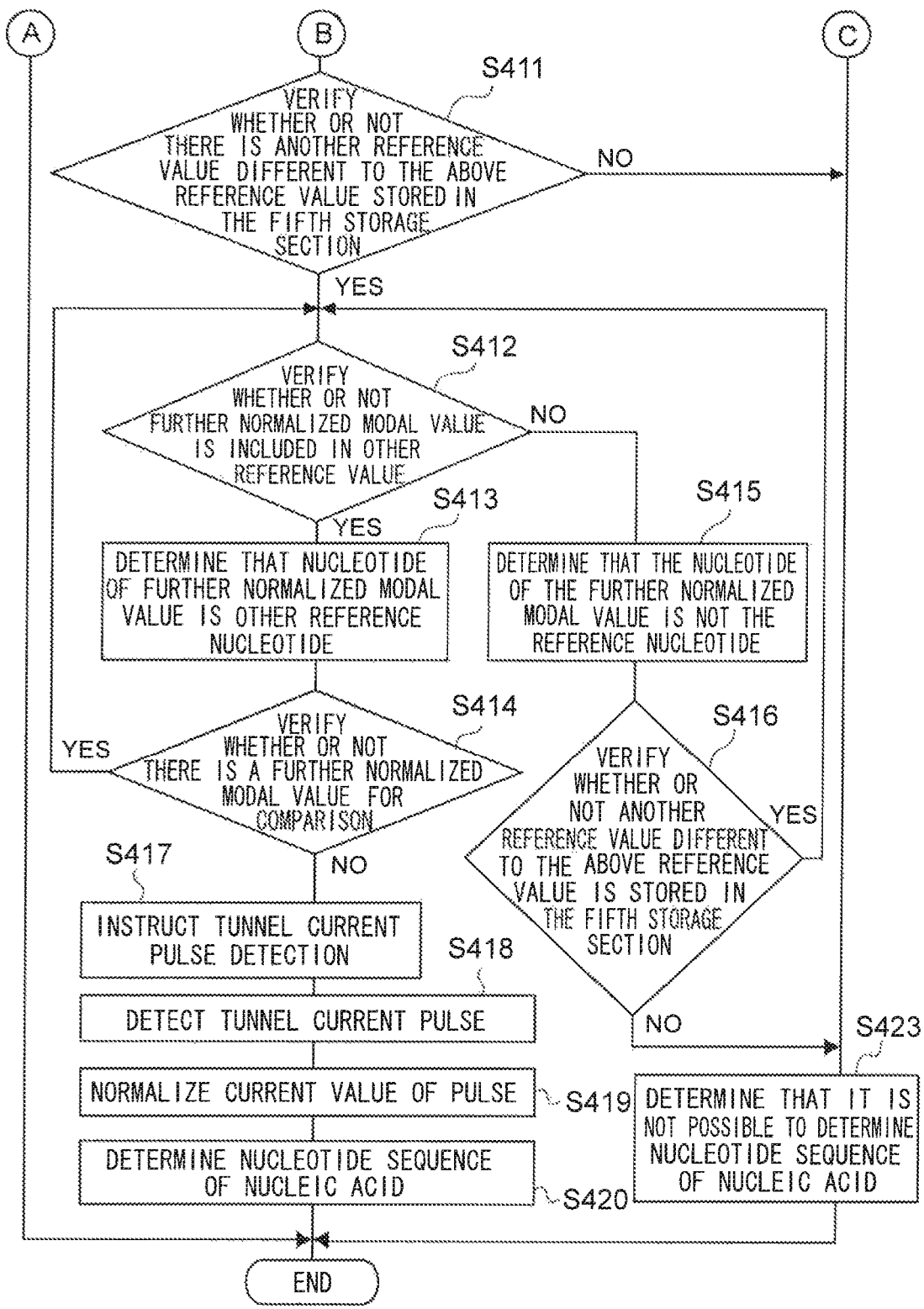
FIG. 8B is a flow chart illustrating an example of a flow of processing according to yet another device of the present invention.

Explanation follows regarding an example of flow of a polynucleotide nucleotide sequence determination operation of the device 300 with reference to the flow chart illustrated in FIG. 8A and FIG. 8B.

At S401, the device 300 holds the electrode pair 11 in a sample.

At S402, the voltage application section 21 applies a voltage to the electrode pair 11.

At S403, the current measuring section 31 measures the current value of the tunnel current generated in the processing of S402.

At S404, the calculation section 51 calculates the modal value of the current value measured in the processing of S403.

At S405, the normalization section 71 normalizes the modal value calculated in the processing of S404.

At S406, the comparison section 61 compares the modal value normalized in the processing of S405 against the reference value, and verifies whether or not the normalized modal value is included in the reference value.

At S406, when verified by the comparison section 61 that the modal value is included in the reference value (when YES) processing transitions to S407. However, when verified by the comparison section 61 that the modal value is not included in the reference value (when NO), processing transitions to S421.

At S407, the comparison section 61 determines that the nucleotide of the normalized modal value is the reference nucleotide associated with this reference value.

At S408, the comparison section 61 verifies whether or not further normalized modal values for comparison are present. When at S408 the comparison section 61 verifies that there are no further normalized modal values for comparison (when NO), processing transitions to S409. However, when at S408 the comparison section 61 verifies that there is a further normalized modal value for comparison (when YES), processing transitions to S410.

At S409, the comparison section 61 determines that the polynucleotide to which the present invention is being applied is configured by a single type of nucleotide, and determines that the nucleotide sequence of the polynucleotide is configured by the reference nucleotide identified in the processing of S407. Processing is then ended.

At S410, the comparison section 61 determines that the polynucleotide to which the present invention is being applied is configured by plural types of nucleotide.

At S411, the comparison section 61 verifies whether or not another different reference value to the above reference value is stored in the fifth storage section. When at S411 the comparison section 61 verifies that there is another reference values stored in the fifth storage section (when YES), processing transitions to S412. However, when at S411 the comparison section 61 verifies that there are no other reference values stored in the fifth storage section (namely, when the modal value is not included in any of the reference values stored in the fifth storage section), processing transitions to S423.

At S412, the comparison section 61 compares the additional normalized modal value verified to exist in the processing of S411 against the other reference value, and verifies whether or not the further normalized modal value is included in the other reference value. When at S412 the comparison section 61 verifies that the further normalized modal value is included in the reference value (when YES), processing transitions to S413. However, when at S412 the comparison section 61 verifies that the modal value is not included in the reference value (when NO), processing transitions to S415.

At S413, the comparison section 61 determines that the nucleotide of the further normalized modal value is the other reference nucleotide associated with the other reference value.

At S414, the comparison section 61 verifies whether or not there is a further normalized modal value for comparison. When at S414 the comparison section 61 verifies that there are no further normalized modal values for comparison (when NO), processing transitions to S417. However, when at S414 the comparison section 61 verifies that there is a further normalized modal value for comparison (when YES), processing returns to S412.

At S415, the comparison section 61 determines that the nucleotide of the further normalized modal value is not the other reference nucleotide associated with the other reference value, and processing transitions to S416.

At S416, the comparison section 61 verifies whether or not another reference value different to the above reference value is stored in the fifth storage section. When at S416 the comparison section 61 verifies that there is another different reference value to the above reference value stored in the fifth storage section (when YES), processing returns to S412 above. Here, similarly to in the processing in S412, the comparison section 61 compares the modal value against the other reference value and verifies whether or not the modal value is included in the other reference value. However, when at S412 the comparison section 61 verifies that no other reference values are stored in the fifth storage section (namely when the modal value is not included in any of the reference values stored in the fifth storage section), processing transitions to S423.

At S417, as a result of the processing of S414 the comparison section 61 instructs the detection section 41 to detect tunnel current pulses.

At S418, the detection section 41 detects tunnel current pulses as a result of the processing of S417.

At S419, the additional normalization section 72 normalizes current values of the pulses detected by the processing of S418.

At S420, the additional comparison section 62 compares the current values normalized by the processing of S419 against the reference values, and determines the order of the nucleotides configuring the polynucleotide (determines the nucleotide sequence of the polynucleotide). Processing is then ended.

At S421, the comparison section 61 determines that the nucleotide of the normalized modal value is not the other reference nucleotide associated with the reference value, and processing transitions to S422.

At S422, the comparison section 61 verifies whether or not there is another reference value different to the above reference value stored in the fifth storage section. When at S422 the comparison section 61 verifies that there is another reference value stored in the fifth storage section (when YES), processing returns to S406. Here, similarly to in the processing at S406, the comparison section 61 compares the modal value against the other reference value and verifies whether or not the modal value is included in the other reference value. However when at S406 the comparison section 61 verifies that there are no other reference values stored in the fifth storage section (namely when the modal value is not included in any of the reference values stored in the fifth storage section), processing transitions to S423.

At S423, the comparison section 61 determines that the nucleotide of the normalized modal value is not any of the reference nucleotides associated with the reference values stored in the fifth storage section, and determines that it is not possible to determine the nucleotide sequence of the polynucleotide. Processing is then ended.

Since the device 300 of the present exemplary embodiment is provided with the additional members described above, it is possible to determine the nucleotide sequence of a polynucleotide configured by a single type of nucleotide, and it is also possible to determine the nucleotide sequence of a polynucleotide configured by plural types of nucleotide.

Note that the present invention includes the following aspects.

In the nucleotide identification method of the present invention, preferably the modal value is calculated by generating a histogram expressing a relationship between the maximum current value of each pulse and a number of pulses corresponding to this maximum current value, fitting the generated histogram to a specific function, and deriving a peak value of the fitted Gauss function. The function is preferably a Gauss function.

In the nucleotide identification device of the present invention, preferably the inter-electrode distance is a length of 0.5 times to 2 times the molecular diameter of the nucleotide.

Preferably the polynucleotide nucleotide sequence determination method of the present invention further includes: a process of detecting pulses of a tunnel current; a process of normalizing the current values of the pulses by dividing the current values by the modal value of the standard nucleotide; and a process of comparing the normalized current values against the reference value.

Preferably the polynucleotide nucleotide sequence determination device of the present invention further includes: a detection means that detects pulses of a tunnel current; a normalization means that normalizes the current values by dividing the current values of the pulses by the modal value of the standard nucleotide; and comparison means that compares the normalized current values against the reference value. In such a device, preferably the inter-electrode distance is a length of 0.5 times to 2 times the molecular diameter of the nucleotide.

The present invention is not limited to the exemplary embodiments described above, and various modifications are possible within the scope expressed by the claims. More detailed explanation follows regarding the present invention in the Examples below. Note that the present invention is not limited by the Examples below.

EXAMPLES

Example 1

Figure 9:
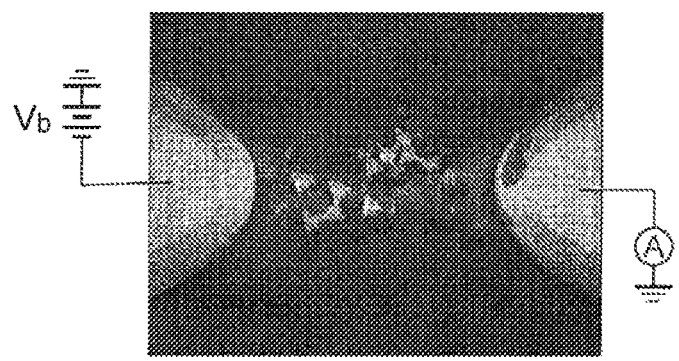
FIG. 9 is a schematic diagram to explain measurement of tunnel current flowing in a single nucleotide molecule trapped between a gold nanoelectrode pair.

As illustrated in FIG. 9 and FIG. 10, in the following Example explanation is given regarding statistical identification of deoxythymidine 5'-monophosphate (dTMP), guanosine 5'-monophosphate (GMP), adenosine 5'-monophosphate (AMP), and cytidine 5'-monophosphate (CMP) based on tunnel current measurements. A method for resolving issues with electron transport through a single molecule for performing such identification is based on trapping a nucleotide dissolved in Milli-Q water between an electrode pair of gold nanoelectrodes, illustrated in FIG. 9, and observing temporary changes in tunnel current (I) arising between the two electrodes (see M. Tsutsui, M. Taniguchi, T. Kawai, Nano Lett. 9, 1659 (2009), and M. Tsutsui, M. Taniguchi, T. Kawai, Appl. Phys. Lett. 93, 163115 (2008)).

Note that in FIG. 9 is a schematic diagram to explain measurement of tunnel current flowing in a single nucleotide molecule that is trapped between the electrodes of the gold nanoelectrodes when a DC bias ($V_b$) is applied underwater. FIG. 10 illustrates molecular structure of each nucleotide employed in the present example.

Nanoelectrode Pair Fabrication

Figure 11:
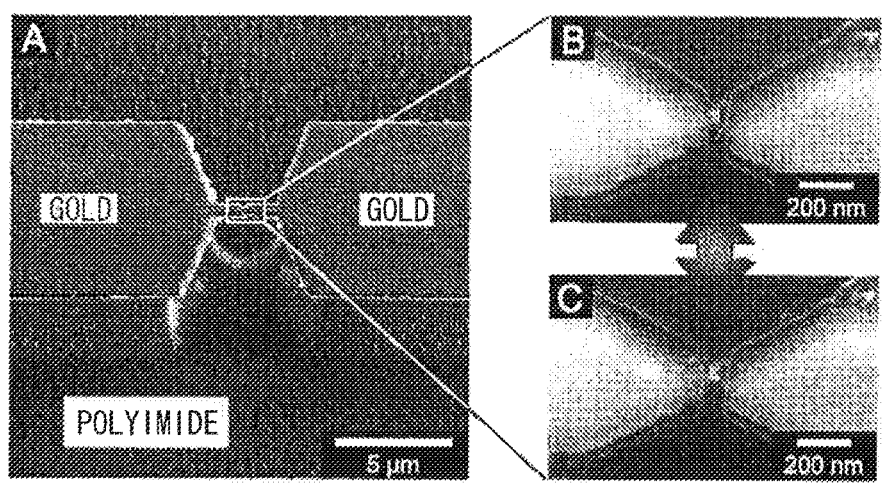
FIG. 11 shows scanning electron micrographs of a nano-electrode pair capable of being structured mechanically.

The gold nanoelectrode pair is fabricated, and fabricated nanoelectrode pair is immersed in Milli-Q water in which a nucleotide has been dissolved, and tunnel current arising between the electrodes of the nanoelectrode pair is measured. FIG. 11 illustrates a scanning electron micrograph of the fabricated nanoelectrode pair. A of FIG. 11 illustrates a nanoscale gold junction fabricated on a polyimide-coated flexible metal substrate. This gold junction is unsupported. B and C of FIG. 11 are enlarged illustrations of the narrowest constriction of the nanoscale junction. Such a nanoelectrode pair is fabricated as follows.

A principle requirement for measuring conductance of a single nucleotide molecule is forming an electrode pair with an inter-electrode distance comparable to the length of the nucleotide (about 1 nm). Such an electrode pair is formed employing a nano-mechanically-controllable break junction (MCBJ) method.

Specifically, first standard electron beam lithography and lift-off technology is used to pattern form nanoscale gold junctions on a polyimide (Catalogue Number: Pyre-M1, manufactured by Industrial Summit Technology) coated flexible metal substrate employing an electron beam lithography device (JEOL Ltd., catalogue number: JSM6500F). Next, polyimide beneath the junctions is removed by etching based on a reactive ion etching process employing a reactive ion etching device (Samco Inc., catalogue number: 10NR). A nanoscale gold bridge structure with a 3-point bent structure is then fabricated by bending the substrate. Such bending of the substrate is performed by employing a piezoelectric actuator (catalogue number: APA150M, made by CEDRAT).

The bridge is then pulled, and the nanoelectrode pair are formed by breaking a portion of the bridge. Specifically, a data acquisition board (made by National Instruments Corporation, catalogue number: NI PCIe-6321) is employed to apply a DC bias voltage (Vb) of 0.1V to the bridge employing series resistance of 10 kΩ at a programmed junction stretching speed, pulling the bridge, and breaking the bridge by a resistance feedback method. Next, the bridge is pulled further and the size of the gap (inter-electrode distance) occurring due to the break is set to the length of the target nucleotide molecule (about 1 nm).

The nanoelectrode pair is obtained by the above sequence.

Measurement of the tunnel current arising between the nanoelectrode pair

The thus fabricated nanoelectrode pair is immersed in Milli-Q water in which a nucleotide has been dissolved, and tunnel current (I) arising when the nucleotide is trapped between the nanoelectrode pair is measured.

The tunnel current (I) passing between the nanoelectrode pair at formed with an inter-electrode distance length of 1 nm is amplified employing a homemade logarithmic amplifier. Employing such a logarithmic amplifier enables current at the picoampere level to be read at >1 kHz. Next, a signal of the amplified current is recorded on a computer at a sampling rate of 2 kHz employing a DAQ card with 24-bit resolution (National Instruments, Catalogue Number: NI USB-9234).

The current (I) is measured continuously for 50 minutes for each of the nanoelectrode pair fabricated as described above. A new sample is changed over every time a sample is measured.

Firstly, employing GMP as the nucleotide, the tunnel current (I) is measured over 3000 seconds (50 minutes) with a bias voltage of 0.75V applied between a nanoelectrode pair adjusted to an inter-electrode distance of 1 nm. The measured tunnel current is plotted against time (seconds). A of FIG. 12 illustrates a portion of "a curve (I–t curve) expressing a relationship between tunnel current and time (seconds)" that is obtained by such plotting. The signals marked with asterisks in A of FIG. 12 are shown enlarged in B of FIG. 12. In B of FIG. 12, $I_p$ defines the maximum value of the height of a pulse pattern signal, and $t_d$ defines the maximum value of the width of the pulse pattern signal.

In A of FIG. 12 it can be seen that a number of pulse pattern signals of various heights appear irregularly over time. A small offset of about 80 pA and a noise level of about ±10 pA are caused by the ionic properties of polarized GMP in the solution. The I–t curve is notable for the presence of plural pulses with different sized "pulse maximum current values $(I_p)$".

As illustrated in B of FIG. 12, it is clear from enlarging the current pulses that the pulses have different widths to each other. Moreover, as can be seen from B of FIG. 12 the tunnel current rises sharply from the base level, and also drops back sharply to the base level. This sharp rise in the tunnel current may be taken to indicate that a single molecule of GMP is trapped between the nanoelectrode pair, and the sharp drop in current may be taken to indicate that the trapped GMP has moved away.

It should moreover be noted that, as illustrated in B of FIG. 12, the current becomes unstable as a GMP molecule becomes trapped between the nanoelectrode pair. It is thought that this is probably caused by atomic motion of migratory nucleotide molecules between the nanoelectrode pair (M. Zwolak, M. Di Ventra, Nano Lett. 5, 421 (2005), J. Lagerqvist, M. Zwolak, M. Di Ventra, Byophys. J. 93, 2384 (2007)). Under the present experiment conditions, it is expected that large fluctuations in tunnel current would be caused when the GMP molecule is not strongly bonded to the metal electrodes through a given chemical bond, since the distance between the electrodes and the GMP molecule change even with very slight changes to the conformation of the GMP molecule. Increasing the inter-electrode distance further weakens the electron bonding between the electrode and the GMP molecule, with an accompanying drop in tunnel current. Conversely, reducing the inter-electrode distance further strengthens the electron bonding between the electrode and the GMP molecule, with an accompanying increase in tunnel current.

Figure 13:
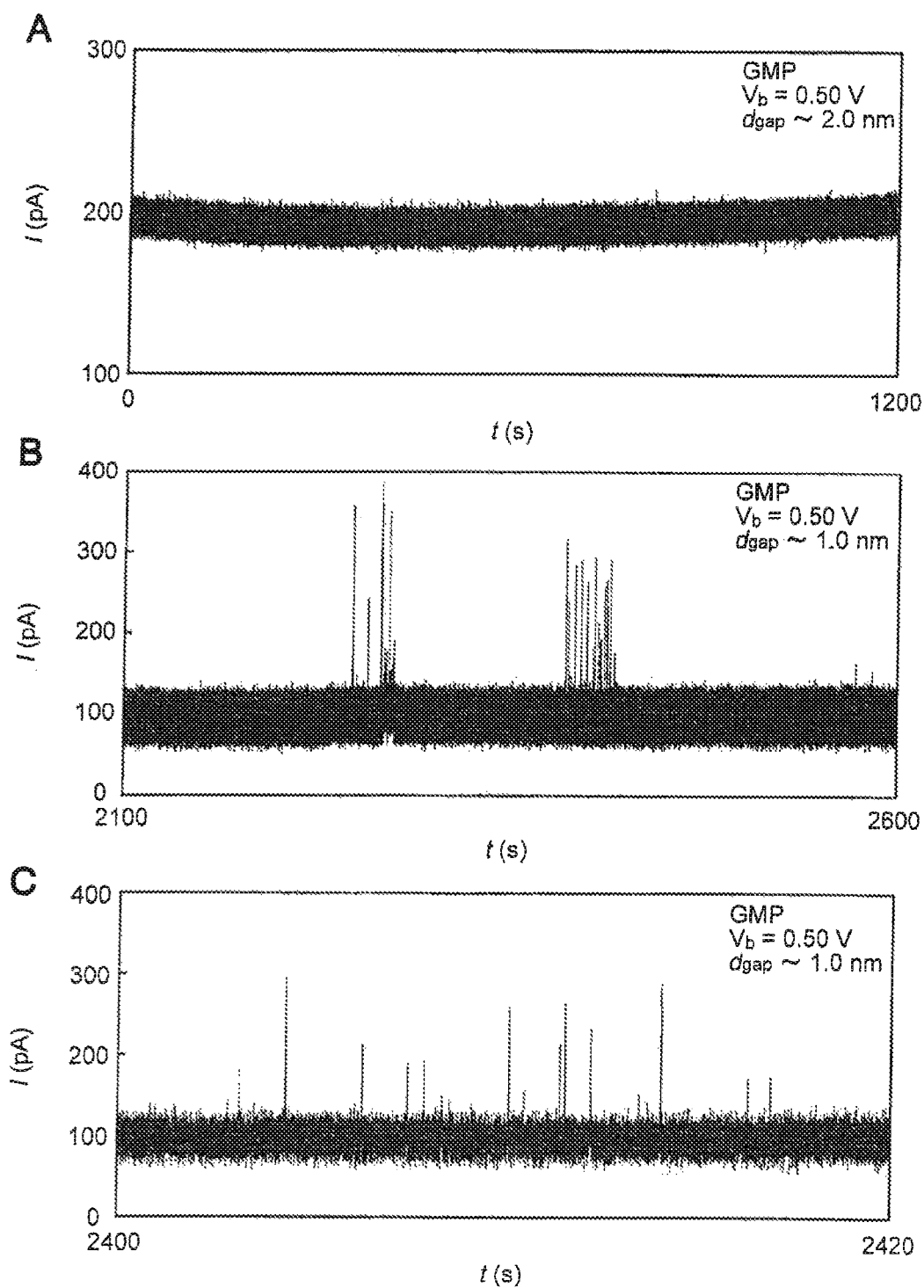
FIG. 13 is a diagram illustrating I–t curves obtained for various inter-electrode distance ($d_{gap}$) conditions.

Tunnel current is measured employing GMP as the nucleotide and employing an inter-electrode distance that is greater than the molecular diameter of the nucleotide (about 1 nm for GMP) for the nanoelectrode pair. FIG. 13 illustrates an I–t curve obtained for various inter-electrode distance $(d_{gap})$ conditions.

A of FIG. 13 illustrates an example of an I–t curve measured with the $d_{gap}$ adjusted to about 2.0 nm. As illustrated in A of FIG. 13, when the inter-electrode distance of the nanoelectrode pair is longer than the molecular diameter of the nucleotide (about 1 nm for GMP), the distinctive signals that can be observed in B and C of FIG. 13 are lost, and a featureless curve appears in which tunnel current pulses are not exhibited.

However, B of FIG. 13 illustrates a distinctive pulse pattern signal expressing a single nucleotide molecule trapped between the electrodes that is observed when the $d_{gap}$ is set to close to the molecular diameter of the nucleotide (about 1 nm). The pulse pattern signals show a trend of appearing in a number of clusters at relatively long time intervals (50 to 1000 seconds). This indicates adsorption of the nucleotide onto the surface of the gold electrodes. The affinity of nucleotides to gold has been researched at length (K. A. Brown, S. Park, K. Hamad-Schifferli, J. Phys. Chem. C 112, 7517 (2008)). Electrons are able to start passing through the potential barrier via the nucleotide when the nucleotide is adsorbed in the vicinity of the region of the gap between the electrode pair. Pulses of tunnel current arise until there is thermal dissociation of the bond between the gold and the nucleotide. After separation, signal does not arise until the next molecule approaches the inter-electrode gap between the nanoelectrode pair.

C of FIG. 13 illustrates one of the peak clusters illustrated in B of FIG. 13 in more detail. Tunnel current pulses of various heights appear irregularly over time.

Tunnel current is further measured employing a solvent in which a nucleotide is not dissolved. The I–t curves are obtained as a result without the features illustrated in A and B of FIG. 12.

Figure 14:
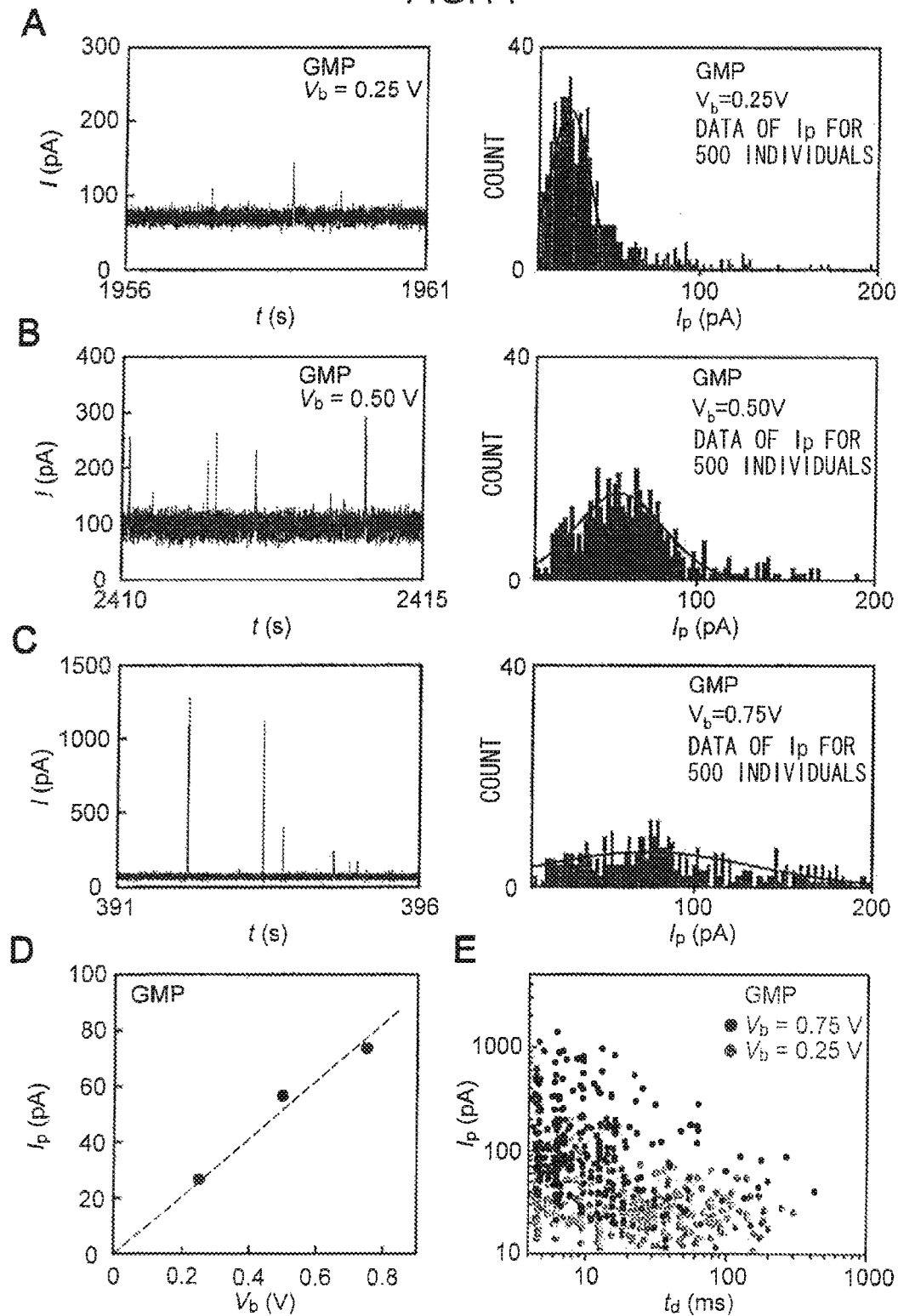
FIG. 14 is a diagram illustrating measurement results of the maximum current values of GMP when a bias voltage ($V_b$) is 0.25V to 0.75V.

Next, the electron transport mechanism of a single nucleotide molecule is examined by investigating the dependency on the bias voltage of the $I_p$. Tunnel current is measured over time, increasing the bias voltage $(V_b)$ from 0.25V to 0.75V. The results are illustrated on the left hand side of A to C of FIG. 14. The left hand side panels in A to C of FIG. 14 show portions of I–t curves representing tunnel current pulses respectively obtained when the $V_b$ is at 0.25V, 0.50V, and 0.75V. As illustrated in the left hand side panels of A to C of FIG. 14, pulse pattern signals with an $I_p$ are detected under each of the measured conditions of $V_b$, with these signals resembling the signals illustrated in FIG. 12.

Distinctive characteristics of the $I_p$–$V_b$ are investigated by performing statistical analysis of tunnel current pulses. Histograms are generated from data obtained of the $I_p$ for 500 individuals. The generated $I_p$ histograms are illustrated in the right hand side panels of A to C of FIG. 14. It is clear from examination of these $I_p$ histograms that the $I_p$ is distributed over a wide range exceeding single digits.

This is related to the fact that there are various conformations of the migratory GMP molecule in the gap between the electrodes, and there are various different types of contact lengths between the electrodes and the molecule. However, as illustrated in the panels on the right hand side of A to C of FIG. 14, adequately defined single peak profiles emerge in the $I_p$ distribution. The peak in the right hand side panel of A of FIG. 14 is at 27 pA, the peak in the right hand side panel of B is at 57 pA, and the peak in the right hand side panel of C is at 74 pA. The structure of these single peaks indicates the preferable conformations of the GMP molecule present in the space in an electric field of the nanoscale gap between the electrode pair. This is thought to be due in part to the fact that as suggested by molecular simulation, a nucleotide is arranged along a curve of the electrostatic potential induced by $V_b$ (M. Zwolak, M. Di Ventra, Rev. Mod. Phys. 80, 141 (2008)).

The single $I_p$ peak is related to the conductance of a single GMP molecule of a specific conformation, and is considered to be statistically meaningful in the present tests. As illustrated by the solid lines in the right hand side panels of A to C of FIG. 14, a Gaussian function is fitted to the histogram, and a single $I_p$ peak extracted. The respective extracted $I_p$ peaks are then plotted as a function of $V_b$ as illustrated in D of FIG. 14. When thus plotted, it is clearly shown that there is a linear increase of the $I_p$ accompanying increasing $V_b$. Based on this dependency between $I_p$ and $V_b$, inferences are made regarding a mechanism in which electron transport in a nucleotide is possible. Firstly, it is supposed that a barrier that cannot be ignored is present at the interface between the electrodes and the molecule and obstructs charge injection. It is understood from a rough estimation of a molecular frontier orbital level using DFT calculation (Gaussian03, revisionC. 02; M. J. Frisch et al., Gaussian, Inc., Pittsburgh Pa., 2003) employing B3LYP functional and a 6-31G** basis set that the energy of the barrier that obstructs charge injection at a point of contact between gold and guanine is about 2.6 eV. Note that the Fermi level of the electrodes is assumed to match an intermediate point of the gap between the HOMO and the LUMO of the molecule. This assumption should only be valid regarding gold-GMP-gold system where molecules interact weakly with the electrodes.

Accordingly, even when $V_b$ is 0.75V, an electron has to overcome a barrier of energy exceeding 2 eV in the bond between gold and guanine. A coherent tunnel effect may naturally be suspected in such an environment (A. Troisi, M. A. Ratner, Small 2, 172 (2006)). According to a Simmons model, when the kinetic energy ($eV_b$) of an electron that has been accelerated by an electric field is small enough that it cannot be ignored in comparison to a tunnel effect barrier, tunnel current changes linearly together with the bias voltage ($V_b$) (e is the charge of an electron) (J. G. Simmons, J. Appl. Phys. 34, 1793 (1963), W. Wang, T. Lee, M. A. Reed, Phys. Rev. B 68, 035416 (2003)). The linear characteristics between $I_p$ and $V_b$ suggest a coherent tunnel effect via GMP at a conductance of 1 molecule of about 0.1 nS, with this obtaining a match with first principles calculations.

Electrostatic force induced by a transverse field is expected to influence the duration for which a nucleotide is trapped in the nanoscale gap between the electrode pair (M. Tsutsui, M. Taniguchi, T. Kawai, Nano Lett. 9, 165 9 (2009)). However, as illustrated in the $I_p$-$t_d$ scatter diagram of E of FIG. 14, $V_b$ is clearly shown not to be dependent on $t_d$ Accordingly, although a transverse field makes a large contribution to selecting a possible conformation of a molecule and electrically detecting a single nucleotide by imparting an adequately defined $I_p$, it is not foreseen that a transverse field could be employed to control movement duration.

Evaluation of the remaining nucleotides (namely AMP, dTMP and CMP) is attempted towards DNA sequencing.

Figure 15:
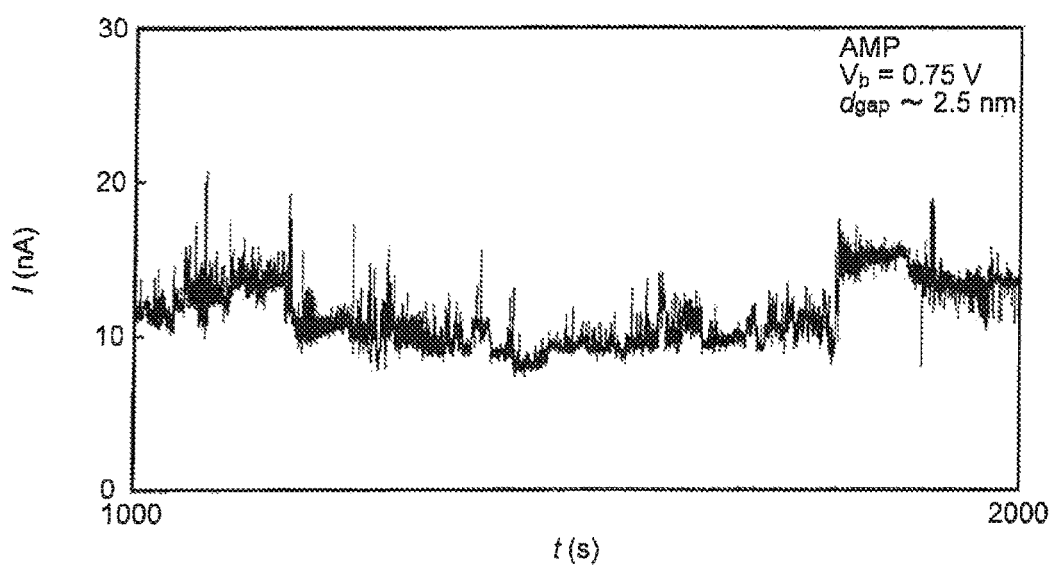
FIG. 15 is a diagram illustrating an abnormal I–t curve for adenosine monophosphate (AMP) obtained when the inter-electrode distance ($d_{gap}$) is relatively long (about 2.5 nm).

An I-t curve is generated for AMP in a case in which the inter-electrode distance ($d_{gap}$) is relatively long (about 2.5 nm). The generated I-t curve is illustrated in FIG. 15. Note that the vertical axis is nA. The I-t curve has a characteristic large offset of about 10 nA and a unidirectional up-down current fluctuation. AMP accordingly shows complex characteristics, and the I-t curve for AMP has a characteristic of a high current base level (>500 pA) and a lot of noise, as illustrated in FIG. 15. Such characteristics of the I-t curve are even observed when the inter-electrode distance is set longer than 2 nm. Moreover, when the inter-electrode distance is further enlarged to over 5 nm for AMP, the tunnel current decreases smoothly together with the increase in the $d_{gap}$.

Adenine has been demonstrated to bond non-specifically to gold to a relatively high degree (J. Kundu, O. Neumann, B. G. Janesko, D. Zhang, S. Lal, A. Barhoumi, G. E. Scuseria, N. J. Halas, J. Phys. Chem. ASAP article, K. A. Brown, S. Park, K. Hamad-Schifferli, J. Phys. Chem. C 112, 7517 (2008)). Due to this distinctive affinity of adenine, it is difficult to prevent unintended excessive adsorption of AMP onto gold, thereby impeding the electrical detection of a single nucleotide molecule through $I_p$ measurement.

Moreover, characteristic tunnel current (I) pulses were successfully observed for the other 2 nucleotides (dTMP and CMP). A of FIG. 16 illustrates I-t curves obtained for dTMP and CMP when $V_b$ is 0.75V (note that results for GMP are also illustrated). As illustrated in B of FIG. 16, the corresponding $I_p$ histograms for dTMP, CMP and GMP have a single peak, suggesting an effective result of a lateral field to suppress warping in molecular structure. The solid line in B of FIG. 16 illustrates fitting of a Gaussian function to the histogram. The peaks (modal values) of dTMP, CMP and GMP are respectively at 96 pA, 30 pA and 42 pA.

Accordingly, GMP, CMP and dTMP can be identified based on the values of the horizontal axis (tunnel current) of such $I_p$ peaks. The sequence of electrical conductivities of single molecules can moreover be determined to be GMP>CMP>dTMP based on these $I_p$ peaks. As a result, the difference in the gap between the HOMO and LUMO of nucleotides of DNA can be qualitatively interpreted to reflect that guanine>cytosine to thymine (M. Zwolak, M. Di Ventra, Nano Lett. 5, 421 (2005), M. Taniguchi, T. Kawai, Physica E 33, 1 (2006)), thus providing backing to the assertion by the inventors regarding electron transport based on tunnel effect through a single nucleotide.

Tunnel current (I) pulses are moreover observed respectively for the nucleotides configuring DNA (dCMP, dGMP, dAMP and dTMP) and the nucleotides configuring RNA (CMP, GMP, AMP and UMP) employing an inter-electrode distance of 0.8 nm and a voltage of 0.4V. Conductance histograms are then generated employing 1000 individual samples, and fitting is performed employing Gaussian functions. The results for the nucleotides configuring DNA are illustrated in A of FIG. 17, and the results for the nucleotides configuring RNA are illustrated in B of FIG. 17. The solid lines illustrated in A and B of FIG. 17 show the fitting of Gaussian functions to the histogram.

As can be seen from A and B of FIG. 17, the conductance histograms of each of the nucleotides have a single peak. The peaks (modal values) for dCMP, dGMP, dAMP and dTMP are respectively at 60 pS, 87 pS, 67 pS and 39 pS. The peaks (modal values) for CMP, GMP, AMP and UMP are respectively at 64 pS, 123 pS, 92 pS and 50 pS.

Identification of a single nucleotide molecule is an important issue in DNA sequencing through tunnel current detection. As illustrated in C of FIG. 16 and in FIG. 17, the $I_p$ peaks (or the conductance peaks) of the nucleotides differ between each nucleotide. When the histograms are overlaid on each other, it is clearly proven that the $I_p$ distributions (conductance distributions) significantly overlap with each other. This makes it clear that single shot measurement is unquestionably insufficient in establishing nucleotide types. Moreover, it is suggested that it is of great importance that tunnel current statistical averages be collected over the duration for which a DNA nucleotide sequence is being read in order to collect data at high speed whilst the DNA nucleotide sequence is moving through a nanoscale gap between an electrode pair (J. Lagerqvist, M. Zwolak, M. Di Ventra, Byophys. J. 9 3, 2384 (2007)). Namely, it could be said that it is necessary to compare statistical average values (modal values) of the tunnel current in order to establish the sequence of DNA at a 1 base level.

Accordingly, ultimately technology based on single molecules requires accurate control of DNA dynamics in the vicinity of a nanoelectrode pair, however promising tools enabling manipulation of molecule movement at the single molecule level are already being developed (U. F. Keyser, B. N. Koeleman, S. V. Dorp, D. Krapf, R. M. M. Smeets, S. G. Lemay, N. H. Dekker, C. Dekker, Nat. Phys. 2, 473 (2006), H. Peng, X. S. Ling, Nanotechnol. 20, 185101 (2009)).

Note that all of the experiments described above in the present Example are performed at room temperature, employing a solution of 5 µM of nucleotide in Milli-Q water under a flow of argon gas. All nucleotides are purchased from the Tokyo Chemical Industry Co., Ltd.

Example 2

Figure 20:
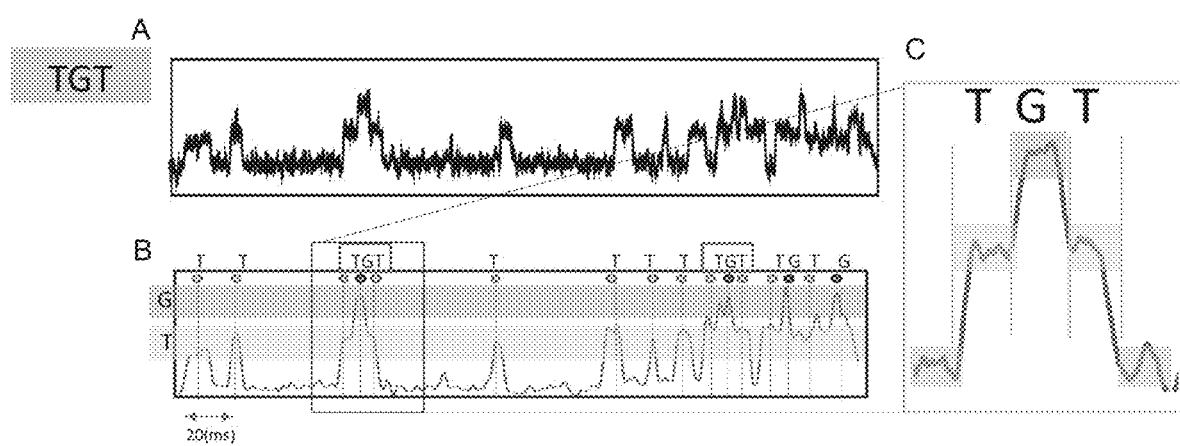
FIG. 20 is a diagram illustrating an enlarged portion of FIG. 18.
Figure 21:
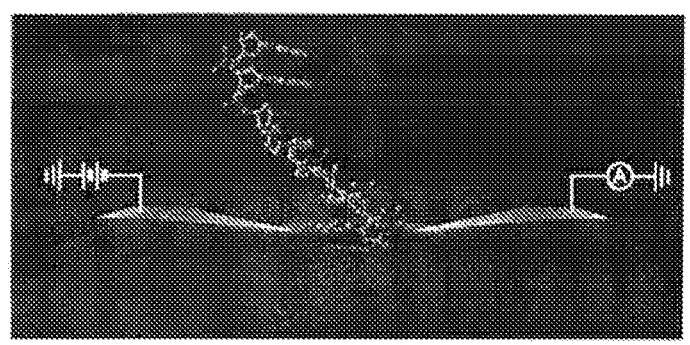
FIG. 21 is a schematic diagram to explain a DNA sequencing method based on ion current.

Explanation follows regarding statistical determination of the nucleotide sequence of DNA (DNA configured by a GTG nucleotide sequence (referred to below as "GTG"), DNA configured by a TGT nucleotide sequence (referred to below as "TGT"), and DNA configured by a GGG nucleotide sequence (referred to below as "GGG")) based on tunnel current measurement, as illustrated in FIG. 18 to FIG. 20.

The nanoelectrode pair employed in Example 1 is immersed in Milli-Q water in which a DNA of one of the 3 types listed above has been dissolved. Then, similarly to the method used in Example 1, tunnel current arising between the electrodes of the nanoelectrode pair is measured, and conductance is calculated from the current values. Note that the voltage applied between the nanoelectrode pair is 0.4V. The calculated conductance is divided by the modal value (87 pS) of deoxyguanosine monophosphate (dGMP), described above, illustrated in A of FIG. 17. The results of this experiment are illustrated in FIG. 18. A, B and C of FIG. 18 show respective results for when GTG, TGT and GGG are employed.

1. Determination of Nucleotide Type

A "relative modal value of dGMP" is derived as 1 by dividing the modal value of dGMP (87 pS) illustrated in A of FIG. 17 by the modal value of dGMP (87 pS). Next, the full width at half maximum of the Gaussian function fitted to the dGMP histogram illustrated in A of FIG. 17 is derived as 44 pS. This full width at half maximum is divided by the modal value of dGMP. A "full width at half maximum centered on the relative modal value of dGMP" of 44 pS is accordingly obtained. This "full width at half maximum centered on the relative modal value of dGMP" and a "full width at half maximum centered on the relative modal value of dGTP" exhibit the same value. Accordingly, the "full width at half maximum centered on the relative modal value of dGMP" can be taken to be an indicator for dGTP. In the following, the "full width at half maximum centered on the relative modal value of dGMP" is referred to as a "range indicating dGTP".

Similarly, the "relative modal value of dGMP" is derived as 0.45 by dividing the modal value of dTMP (39 pS) illustrated in A of FIG. 17 by the modal value of dGMP (87 pS). Next, the full width at half maximum of the Gaussian function fitted to the dTMP histogram illustrated in A of FIG. 17 is derived as 22 pS. A "full width at half maximum centered on the relative modal value of dTMP" of 22 pS is accordingly obtained. This "full width at half maximum centered on the relative modal value of dTMP" and a "full width at half maximum centered on the relative modal value of dTTP" exhibit the same value. The "full width at half maximum centered on the relative modal value of dTMP" can accordingly be taken to be an indicator for dTTP. In the following, the "full width at half maximum centered on the relative modal value of dTMP" is referred to as a "range indicating dTTP".

In A to C of FIG. 18, the shaded regions "G" indicate the range indicating dGTP. Moreover, in A and B of FIG. 18, the shaded regions "T" indicate the range indicating dTTP.

In A of FIG. 18, the graph on the left hand side is a histogram of the conductance of all the measured tunnel currents. The graph on the right hand side is a graph illustrating a relationship between conductance divided by the modal value of dGMP (614 pS) and time (seconds). In the left hand side graph, the vertical axis shows relative conductance, and the horizontal axis shows a count of the measured conductance. In the right hand side graph, the vertical axis shows relative conductance, and the horizontal axis shows time (ms).

3 peaks can be confirmed as appearing in the histogram illustrated by the left hand side graph. The lowermost peak (the peak with the smallest modal value) of the histogram is taken as a base line (noise) conductance.

Next, fitting of Gaussian functions is performed, set so as to be centered on each peak, and a value (conductance modal value) is derived for each peak. As a result, the value of the lowest peak (I0) is 52 pS, the value of the middle peak (I1) is 271 pS, and the value of the uppermost peak (I2) is 666 pS.

Next, the relative modal value of the uppermost peak is derived as 1 by dividing the result of I0 subtracted from I2 (614) by the result of I0 subtracted from I2 (614) (namely the relative modal value of the uppermost peak=(I2−I0)/(I2−I0)). The relative modal value of the middle peak is derived as 0.35 by dividing the result of I0 subtracted from I1 (219) by the result of I0 subtracted from I2 (614) (namely the relative modal value of the middle peak=(I1−I0)/(I2−I0)).

The relative modal value of the uppermost peak is confirmed as being included in the range indicating dGTP, and this relative modal value is determined to be the modal value of "deoxyguanosine triphosphate (G)". Similarly, the relative modal value of the middle peak is confirmed as being included in the range indicating dTTP, and this relative modal value is determined to be the modal value of "deoxythymidine triphosphate (T)".

At B of FIG. 18, the left hand side graph is a histogram of conductance for all measured tunnel currents. The right hand side graph is a graph illustrating a relationship between tunnel current divided by the modal value of GMP (123 pS) and time (seconds). Similarly to A of FIG. 18, the histogram illustrated by the left hand side graph is divided into 3 regions based on the peaks. The modal value (I3) of conductance (base line conductance) for the region including the lowermost peak (20 pS), the modal value (I4) of conductance for the region including the middle peak (53 pS), and the modal value (I5) of conductance for the region included in the highest peak (143 pS) are derived.

Next, the relative modal value for the uppermost peak is derived as 1 by dividing the result of I3 subtracted from I5 (123) by the result of I3 subtracted from I5 (123) (namely the relative modal value of the uppermost peak=I5−I3/I5−I3). The relative modal value for the middle peak is derived as 0.27 by dividing the result of I3 subtracted from I4 (33) by the result of I3 subtracted from I5 (123) (namely the relative modal value of the uppermost peak=(I4−I3)/(I5−I3)).

The relative modal value of the uppermost peak is confirmed as being included in the range indicating dGTP, and this relative modal value is determined to be the modal value of "G". Similarly, the relative modal value of the middle peak is confirmed as being included in the range indicating dTTP, and this relative modal value is determined to be the modal value of "T".

In C of FIG. 18, the left hand side graph is a histogram of conductance for all measured tunnel currents. The right hand side graph is a graph illustrating a relationship between tunnel current divided by the modal value of dGMP (230 pS) and time (seconds). Similarly to in A of FIG. 18, the histogram illustrated by the left hand side graph is divided into 2 regions based on the peaks. The modal value (I6) of conductance (base line conductance) for the region including the lowermost peak (83 pS) and the modal value (I7) of conductance in the region including the uppermost peak (313 pS) are derived.

Next, the relative modal value for the uppermost peak (1) is derived by dividing the result of I6 subtracted from 17 (230) by the result of I6 subtracted from I7 (230) (namely the relative modal value of the uppermost peak=(I7−I6)/(I7−I6)). The relative modal value of the uppermost peak is confirmed as being included in the range indicating dGTP, and this relative modal value is determined to be the modal value of "G".

By referring to the left hand side graph and the right hand side graph of A of FIG. 18, the relative conductance on the right hand side graph can be categorized into a range indicating dGTP and a range indicating dTTP. Similarly to B of FIG. 18, the relative conductance on the right hand side graph can be categorized into a range indicating tGTP and a range indicating dTTP. Namely, it can be seen from A and B of FIG. 18 that the nucleotides of the DNA employed are configured by G and T.

By referring to the left hand side graph and the right hand side graph of C of FIG. 18, nearly all of the relative conductance of the right hand side graph can be categorized into a range indicating dGTP. Namely, it can be seen from C of FIG. 18 that the nucleotides of the DNA employed are configured by G only. From this result, it can be determined that the nucleotide sequence of the DNA is configured by G.

A portion of the right hand side graph of A of FIG. 18 is shown enlarged in FIG. 19. A portion of the right hand side graph of B of FIG. 18 is shown enlarged in FIG. 20.

A of FIG. 19 shows an enlarged portion of the right hand side graph of A of FIG. 18. B of FIG. 19 shows a curve of A of FIG. 19 that has been smoothed by performing adjacent averaging. In B of FIG. 19, the range indicating dGTP is illustrated by heavy shading, and the range indicating dTTP is illustrated by light shading. C of FIG. 19 is an enlarged drawing of a portion of B of FIG. 19.

A of FIG. 20 shows an enlarged portion of the right hand side graph of B of FIG. 18. B of FIG. 20 shows a curve of A of FIG. 20 that has been smoothed by performing adjacent averaging. In B of FIG. 20, the range indicating dGTP is illustrated by heavy shading, and the range indicating dTTP is illustrated by light shading. C of FIG. 20 is an enlarged drawing of a portion of B of FIG. 20.

As illustrated in B of FIG. 19 and B of FIG. 20, the nucleotide indicated by the "relative conductance" included in the range indicating dGTP is determined to be dGTP. Moreover, as illustrated in B of FIG. 19 and B of FIG. 20, the nucleotide is determined to be dTTP from the "relative conductance" being included in the range indicating dTTP.

2. Nucleotide Sequence Determination

Next, in an Example 2, a td histogram is generated based on the graph illustrating a relationship between Ip–Td illustrated in B of FIG. 12. td indicates the duration for which a single nucleotide remains between the nanoelectrode pair. The modal value of td is derived as about 1 ms by fitting a Gaussian function to the td histogram. It is accordingly clear that a single nucleotide remains between the nanoelectrode pair for about 1 ms in the test system employed with Example 2.

Accordingly, since the DNA that is configured by 3 nucleotides employed in Example 2 remains between the nanoelectrode pair for about 3 ms or more, the time-current signal pulse indicating the target DNA illustrated in FIG. 18 and FIG. 14 continues for about 3 ms or more (Condition 1).

Moreover, the time-current signal pulse of the DNA configured by 3 nucleotides exhibits 3 step shaped signals (Condition 2).

Based on Condition 1 and Condition 2, out of the signal illustrated in B of FIG. 19, a pulse is extracted that continues for 3 ms or more and has a step shape. The result is illustrated in C of FIG. 19.

As illustrated in C of FIG. 19, the G first division of the pulse has a profile wherein the normalized current value rises from the base level and passes the reference value for T to exhibit the reference value for G. In the first division, the reference value in which the normalized current value is included for the longest duration is the reference value for G. The nucleotide of the first division can accordingly be identified as G.

The second T division of the pulse has a profile wherein the normalized current value drops from the reference value for G, and after exhibiting the reference value for T, once more rises to exhibit the reference value for G. In the second division, the reference value in which the normalized current value is included for the longest duration is the reference value for T. The nucleotide of the second division can accordingly be identified as T.

The third G division of the pulse has a profile wherein, after exhibiting the reference value for G for a fixed duration, the normalized current value passes the reference value for T and drops to the base level. In the third division, the reference value in which the normalized current value is included for the longest duration is the reference value for G. The nucleotide of the third division can accordingly be identified as G.

By following this sequence, the nucleotide sequence of the DNA that gave rise to this pulse can be determined to be GTG.

Similarly, based on Condition 1 and Condition 2, out of the signal illustrated in B of FIG. 20, a pulse is extracted that continues for 3 ms or more and has a step shape. The result is illustrated in C of FIG. 20.

As illustrated in FIG. C of FIG. 20, in the T first division of the pulse has a profile wherein the normalized current value rises from the base level and exhibits the reference value for T. In the first division, the reference value in which the normalized current value is included for the longest duration is the reference value for T. The nucleotide of the first division can accordingly be identified as T.

The second G division of the pulse has a profile wherein the normalized current value rises from the reference value for T, and after exhibiting the reference value for G, drops back to exhibit the reference value for T. In the second division, the reference value in which the normalized current value is included for the longest duration is the reference value for G. The nucleotide of the second division can accordingly be identified as G.

The third T division of the pulse has a profile wherein the normalized current value drops to the base level after exhibiting the reference value for T for a fixed duration. In the third division, the reference value in which the normalized current value is included for the longest duration is the reference value for T. The nucleotide of the third division can accordingly be identified as T.

By following this sequence, the nucleotide sequence of the DNA that gave rise to this pulse can be determined to be TGT.

INDUSTRIAL APPLICABILITY

The present invention enables a single molecule to be identified by analyzing the single molecule using current measurements. The present invention is a foundation stone for next generation sequencers being pursued by the National Institutes for Health (NIH), and may be applied to next generation sequencers in which DNA amplification by PCR and chemical modification of DNA is not required. The present invention may also be applied to high sensitivity sensors for detecting a biomolecule such as an influenza virus or an allergen using one molecule thereof.

Explanation of the Reference Numerals 100 device
200 device
300 device
10 electrode pair
11 electrode pair
20 voltage application section (application means that applies a voltage between the electrodes)
21 voltage application section (application means that applies a voltage between the electrodes)
30 current measuring section (measurement means that measures current values of a tunnel current arising between the electrodes)
31 current measuring section (measurement means that measures current values of a tunnel current arising between the electrodes)
40 detection section (detection means that detects pulses of a tunnel current)
41 detection section (detection means that detects pulses of a tunnel current)
50 calculation section (calculation means that calculates a modal value of the maximum current value of each pulse)
51 calculation section (calculation means that calculates a modal value of the measured current values)
60 comparison section (comparison means that compares the calculated modal value against a reference value)
61 comparison section (comparison means that compares the normalized modal value against a reference value)
62 comparison section (comparison means that compares the normalized modal value against a reference value)
71 normalization section (normalizing means that normalizes the modal value of the current values)
72 normalization section (normalizing means that normalizes the current values.

What is claimed is:

1. A system for sequencing a nucleic acid molecule that comprises a plurality of nucleic acid subunits, comprising:
    a solid substrate comprising a plurality of electrodes that at least partially define a gap, wherein said gap is in a break junction of said solid substrate and configured to have a distance that is less than a molecular diameter of a nucleic acid subunit of said plurality of nucleic acid subunits, wherein said distance is adjustable, and wherein said plurality of electrodes is configured to detect current through said gap when at least a subset of said plurality of nucleic acid subunits are disposed in said gap; and
    a computing device operatively coupled to said plurality of electrodes, wherein said computing device is configured to (1) receive signals corresponding to current measured by said plurality of electrodes, (2) process said signals to determine levels associated with said current to identify said plurality of nucleic acid subunits, and (3) determine a sequence of said nucleic acid molecule based at least in part on said plurality of nucleic acid subunits identified in (2).

2. The system of claim 1, wherein said gap is dimensioned such that said current is measured at a picoampere level.

3. The system of claim 1, wherein said plurality of electrodes is configured to detect said current under an applied voltage that is (1) greater than or equal to 0.25 V or (2) less than or equal to 0.75 V.

4. The system of claim 3, wherein said applied voltage is between 0.25 V and 0.75 V.

5. The system of claim 1, wherein said current is tunneling current.

6. The system of claim 1, wherein individual electrodes of said plurality of electrodes comprise a noble metal.

7. The system of claim 1, wherein said computing device is configured to process said signals to determine said levels and pulses associated with said current to identify said plurality of nucleic acid subunits.

8. The system of claim 1, wherein said computing device is configured to process said signals to determine said levels and durations associated with said current to identify said plurality of nucleic acid subunits.

9. The system of claim 1, wherein said computing device is configured to compare said levels of said current to a reference value of a standard nucleotide to identify said plurality of nucleic acid subunits.

10. The system of claim 9, wherein said reference value is a normalized reference value.

11. The system of claim 1, wherein said computing device is configured to calculate a modal value from said levels of said current to identify said plurality of nucleic acid subunits.

12. The system of claim 11, wherein said computing device is configured to calculate said modal value by (i) generating a histogram expressing a relationship between said levels of said current pulses and a number of said current pulses corresponding to said levels, (ii) fitting said histogram to a given function, and (iii) deriving a peak value of said given function.

13. The system of claim 12, wherein said given function is a Gaussian function.

14. The system of claim 12, wherein said computing device is configured to normalize said modal value by dividing said modal value by a modal value of a standard nucleotide.

15. The system of claim 1, wherein said computing device is configured to amplify said current, such that said signals are amplified values of said current.

16. The system of claim 1, wherein said plurality of electrodes is configured to measure said current at a sampling rate greater than about 1 kHz.

17. A system for sequencing a nucleic acid molecule that comprises a plurality of nucleic acid subunits, comprising:
    a solid substrate comprising a plurality of electrodes that at least partially define a gap, wherein said gap is configured to have a distance that is from about 0.5 times to about a molecular diameter of a nucleic acid subunit of said plurality of nucleic acid subunits, wherein said distance is adjustable at least partially mechanically, and wherein said plurality of electrodes is configured to detect current through said gap when at least a subset of said plurality of nucleic acid subunits are disposed in said gap; and
    a computing device operatively coupled to said plurality of electrodes, wherein said computing device is configured to (1) receive signals corresponding to current measured by said plurality of electrodes, (2) process said signals to determine levels associated with said current to identify said plurality of nucleic acid subunits, and (3) determine a sequence of said nucleic acid molecule based at least in part on said plurality of nucleic acid subunits identified in (2).

18. The system of claim 17, wherein said gap is dimensioned such that said current is measured at a picoampere level.

19. The system of claim 17, wherein said plurality of electrodes is configured to detect said current under an applied voltage that is (1) greater than or equal to 0.25 V or (2) less than or equal to 0.75 V.

20. The system of claim 19, wherein said applied voltage is between 0.25 V and 0.75 V.

21. The system of claim 17, wherein said current is tunneling current.

* * * * *